United States Patent
Wang et al.

(10) Patent No.: US 10,526,309 B2
(45) Date of Patent: Jan. 7, 2020

(54) PAN-TAM INHIBITORS AND MER/AXL DUAL INHIBITORS

(71) Applicant: The University of North Carolina at Chapel Hill, Chapel Hill, NC (US)

(72) Inventors: Xiaodong Wang, Chapel Hill, NC (US); Dehui Zhang, Chapel Hill, NC (US); Dmitri Kireev, Chapel Hill, NC (US); Henry Shelton Earp, III, Chapel Hill, NC (US)

(73) Assignee: THE UNIVERSITY OF NORTH CAROLINA AT CHAPEL HILL, Chapel Hill, NC (US)

( * ) Notice: Subject to any disclaimer, the term of this patent is extended or adjusted under 35 U.S.C. 154(b) by 0 days.

(21) Appl. No.: 15/765,168

(22) PCT Filed: Sep. 30, 2016

(86) PCT No.: PCT/US2016/054840
§ 371 (c)(1),
(2) Date: Mar. 30, 2018

(87) PCT Pub. No.: WO2017/059280
PCT Pub. Date: Apr. 6, 2017

(65) Prior Publication Data
US 2018/0297977 A1    Oct. 18, 2018

Related U.S. Application Data

(60) Provisional application No. 62/236,414, filed on Oct. 2, 2015, provisional application No. 62/238,189, filed (Continued)

(51) Int. Cl.
*C07D 401/04*    (2006.01)
*C07D 401/14*    (2006.01)
(Continued)

(52) U.S. Cl.
CPC .......... *C07D 401/04* (2013.01); *A61K 31/506* (2013.01); *A61K 31/5377* (2013.01);
(Continued)

(58) Field of Classification Search
None
See application file for complete search history.

(56) References Cited

U.S. PATENT DOCUMENTS

| 4,689,338 A | 8/1987 | Gerster |
| 4,929,624 A | 5/1990 | Gerster et al. |

(Continued)

FOREIGN PATENT DOCUMENTS

| WO | WO 2005/018551 A2 | 3/2005 |
| WO | WO 2005/018556 A2 | 3/2005 |

(Continued)

OTHER PUBLICATIONS

Heil, F., et al., "Species-specific recognition of single-stranded RNA via toll-like receptor 7 and 8," Science, 303: 1526-1529 (Mar. 5, 2004).
(Continued)

*Primary Examiner* — Karl J Puttlitz
(74) *Attorney, Agent, or Firm* — Alston & Bird LLP

(57) ABSTRACT

This invention is in the area of improved therapeutic combinations for and methods of treating selected cancers using selected pyrimidine compounds having pan-TAM or Mer/Axl dual receptor tyrosine kinase inhibitory activity in combination with immune checkpoint inhibitors. In one aspect, an improved treatment for select cancers is disclosed using selected pyrimidine compounds described herein in combination with an immune checkpoint inhibitor, for example, a cytotoxic T-lymphocyte-associated protein 4
(Continued)

(CTLA4) inhibitor, a programmed cell death protein 1 (PD1) inhibitor, or a programmed death-ligand 1 (PDL-1) inhibitor, or combination thereof.

17 Claims, 2 Drawing Sheets

Related U.S. Application Data on Oct. 7, 2015, provisional application No. 62/238,658, filed on Oct. 7, 2015.

(51) Int. Cl.

| | | |
|---|---|---|
| *C07D 405/14* | (2006.01) | |
| *C07D 413/14* | (2006.01) | |
| *A61K 31/506* | (2006.01) | |
| *C07D 401/12* | (2006.01) | |
| *C07D 239/48* | (2006.01) | |
| *C07D 417/14* | (2006.01) | |
| *A61P 35/00* | (2006.01) | |
| *A61K 31/5377* | (2006.01) | |
| *A61K 45/06* | (2006.01) | |

(52) U.S. Cl.
CPC ............ *A61K 45/06* (2013.01); *A61P 35/00* (2018.01); *C07D 239/48* (2013.01); *C07D 401/12* (2013.01); *C07D 401/14* (2013.01); *C07D 405/14* (2013.01); *C07D 413/14* (2013.01); *C07D 417/14* (2013.01)

(56) References Cited

U.S. PATENT DOCUMENTS

| | | |
|---|---|---|
| 5,266,575 A | 11/1993 | Gerster et al. |
| 5,268,376 A | 12/1993 | Gester |
| 5,346,905 A | 9/1994 | Gerster |
| 5,352,784 A | 10/1994 | Nikolaides et al. |
| 5,389,640 A | 2/1995 | Gerster et al. |
| 5,446,153 A | 8/1995 | Lindstrom et al. |
| 5,482,936 A | 1/1996 | Lindstrom |
| 5,756,747 A | 5/1998 | Gerster |
| 6,028,076 A | 2/2000 | Hirota et al. |
| 6,039,969 A | 3/2000 | Tomai et al. |
| 6,069,149 A | 5/2000 | Nanba et al. |
| 6,110,929 A | 8/2000 | Gerster et al. |
| 6,113,918 A | 9/2000 | Johnson et al. |
| 6,194,388 B1 | 2/2001 | Krieg et al. |
| 6,194,425 B1 | 2/2001 | Gerster et al. |
| 6,200,592 B1 | 3/2001 | Tomai et al. |
| 6,207,646 B1 | 3/2001 | Krieg et al. |
| 6,239,116 B1 | 5/2001 | Krieg et al. |
| 6,303,347 B1 | 10/2001 | Johnson et al. |
| 6,329,381 B1 | 12/2001 | Kurimoto et al. |
| 6,331,539 B1 | 12/2001 | Crooks et al. |
| 6,339,068 B1 | 1/2002 | Krieg et al. |
| 6,376,501 B1 | 4/2002 | Isobe et al. |
| 6,376,669 B1 | 4/2002 | Rice et al. |
| 6,387,938 B1 | 5/2002 | Mizuguchi et al. |
| 6,406,705 B1 | 6/2002 | Davis et al. |
| 6,426,334 B1 | 7/2002 | Agrawal et al. |
| 6,451,810 B1 | 9/2002 | Coleman et al. |
| 6,476,000 B1 | 11/2002 | Agrawal |
| 6,518,265 B1 | 2/2003 | Kato et al. |
| 6,525,028 B1 | 2/2003 | Johnson et al. |
| 6,525,064 B1 | 2/2003 | Dellaria et al. |
| 6,541,485 B1 | 4/2003 | Crooks et al. |
| 6,545,016 B1 | 4/2003 | Dellaria et al. |
| 6,545,017 B1 | 4/2003 | Dellaria et al. |
| 6,573,273 B1 | 6/2003 | Crooks et al. |
| 6,649,172 B2 | 11/2003 | Johnson |
| 6,656,938 B2 | 12/2003 | Crooks et al. |
| 6,660,735 B2 | 12/2003 | Crooks et al. |
| 6,660,747 B2 | 12/2003 | Crooks et al. |
| 6,664,260 B2 | 12/2003 | Charles et al. |
| 6,664,264 B2 | 12/2003 | Dellaria et al. |
| 6,664,265 B2 | 12/2003 | Crooks et al. |
| 6,667,312 B2 | 12/2003 | Bonk et al. |
| 6,670,372 B2 | 12/2003 | Charles et al. |
| 6,677,347 B2 | 1/2004 | Crooks et al. |
| 6,677,348 B2 | 1/2004 | Heppner et al. |
| 6,677,349 B1 | 1/2004 | Griesgraber |
| 6,680,299 B2 | 1/2004 | Or et al. |
| 6,680,322 B2 | 1/2004 | Castelhano et al. |
| 6,680,324 B2 | 1/2004 | Castelhano et al. |
| 6,683,088 B2 | 1/2004 | Crooks et al. |
| 6,756,382 B2 | 6/2004 | Coleman et al. |
| 6,797,718 B2 | 9/2004 | Dellaria et al. |
| 6,800,276 B2 | 10/2004 | Kim et al. |
| 6,818,650 B2 | 11/2004 | Griesgraber |
| 7,709,214 B2 | 5/2010 | Freeman et al. |
| 2003/0199461 A1 | 10/2003 | Averett et al. |
| 2004/0091491 A1 | 5/2004 | Kedl et al. |
| 2004/0176367 A1 | 9/2004 | Griesgraber et al. |
| 2005/0136065 A1 | 6/2005 | Valiante, Jr. |
| 2006/0100229 A1 | 5/2006 | Hays et al. |

FOREIGN PATENT DOCUMENTS

| | | |
|---|---|---|
| WO | WO 2005/020999 A1 | 3/2005 |
| WO | WO 2005/032484 A2 | 4/2005 |
| WO | WO 2005/066169 A2 | 7/2005 |
| WO | WO 2005/066170 A1 | 7/2005 |
| WO | WO 2005/066172 A1 | 7/2005 |
| WO | WO 2005/076783 A2 | 8/2005 |
| WO | WO 2005/079195 A2 | 9/2005 |
| WO | WO 2005/094531 A2 | 10/2005 |
| WO | WO 2005/123079 A2 | 12/2005 |
| WO | WO 2005/123080 A2 | 12/2005 |
| WO | WO 2006/009826 A1 | 1/2006 |
| WO | WO 2006/009832 A1 | 1/2006 |
| WO | WO 2006/026760 A2 | 3/2006 |
| WO | WO 2006/028451 A1 | 3/2006 |
| WO | WO 2006/028545 A2 | 3/2006 |
| WO | WO 2006/028962 A2 | 3/2006 |
| WO | WO 2006/029115 A2 | 3/2006 |
| WO | WO 2006/038923 A2 | 4/2006 |
| WO | WO 2006/065280 A2 | 6/2006 |
| WO | WO 2006/074003 A2 | 7/2006 |
| WO | WO 2006/083440 A2 | 8/2006 |
| WO | WO 2006/086449 A2 | 8/2006 |
| WO | WO 2006/086633 A2 | 8/2006 |
| WO | WO 2006/086634 A2 | 8/2006 |
| WO | WO 2006/091394 A2 | 8/2006 |
| WO | WO 2006/091567 A2 | 8/2006 |
| WO | WO 2006/091568 A2 | 8/2006 |
| WO | WO 2006/091647 A2 | 8/2006 |
| WO | WO 2006/093514 A2 | 9/2006 |
| WO | WO 2006/098852 A2 | 9/2006 |
| WO | WO 2009/131687 A2 | 10/2009 |
| WO | WO 2010/038081 A2 | 4/2010 |
| WO | WO 2012/028332 A1 | 3/2012 |
| WO | 2013177168 * | 11/2013 |
| WO | WO 2013/177168 A1 | 11/2013 |
| WO | WO 2015/117164 A1 | 8/2015 |
| WO | 2015157127 * | 10/2015 |

OTHER PUBLICATIONS

Pardoll, D., "The blockade of immune checkpoints in cancer immunotherapy," Nature Reviews Cancer, 12:252-264 (2012).
PCT International Search Report and Written Opinion of the International Searching Authority for application PCT/US2016/054840 dated Jan. 26, 2017.

* cited by examiner

PAN-TAM INHIBITORS AND MER/AXL DUAL INHIBITORS

RELATED APPLICATION DATA

This application is a § 371 National Stage entry of PCT International Application No. PCT/US2016/054840, filed Sep. 30, 2016, which claims the benefit of U.S. Provisional Patent Application Ser. No. 62/236,414, filed Oct. 2, 2015; U.S. Provisional Patent Application Ser. No. 62/238,189, filed Oct. 7, 2015; and U.S. Provisional Patent Application Ser. No. 62/238,658; filed Oct. 7, 2015. The disclosures of each of which are incorporated herein by reference in their entirety.

STATEMENT OF GOVERNMENT SUPPORT

This invention was made with government support under grant number HHSN261200800001E awarded by National Institute of Health. The government has certain rights in this invention.

FIELD OF THE INVENTION

The present invention is directed to selected pyrimidine compounds having pan-TAM or Mer/Axl dual receptor tyrosine kinase inhibitory activity and their use as anti-cancer agents, anti-infective agents, immunostimulatory and immunomodulatory agents, and as adjunctive agents in combination with chemotherapeutic, radiation or other standard of care for neoplasms.

BACKGROUND OF THE INVENTION

The TYRO3, AXL (also known as UFO) and MERTK (TAM) family of receptor tyrosine kinases (RTKs) was one of the latest to evolve and one of the last to be identified, partly because they are not strong oncogenic drivers. TAM RTKs are ectopically expressed or overexpressed in a wide variety of human cancers in which they provide tumor cells with a survival advantage. TAM RTKs also play a critical role at the interface of the innate and adaptive immune response. The TAM RTK expressed in individual tumors or in different tumor types are not necessarily redundant; each may connect to downstream survival or motility signaling in slightly different ways.

TAM (Tyro3-Axl-Mer) RTK activation mechanisms are unique, as maximal stimulation involves both an extracellular lipid moiety and a bridging protein ligand. The ligands are γ-carboxylated proteins that bind to the receptor with their carboxy-terminal domain and to the lipid phosphatidylserine (PtdSer) with their amino terminus. The first such ligand, growth arrest-specific protein 6 (GAS6), was purified from conditioned media from normal lung and endothelial cell lines, and binds to all three TAM RTKs. A second γ-carboxylated protein, vitamin K-dependent protein S (PROS1), binds only to MERTK and TYRO3. In the body, PtdSer is abundant but only available to activate TAM receptors when externalized on apoptotic cell membranes, aggregating platelets, exosomes and invading virus envelopes.

TAM receptor and ligand overexpression have been shown in a wide range of solid and hematological tumors, and correlate with poor prognosis in a variety of tumor types and their signals and promote survival, chemoresistance, motility and invasion. In addition, their role in diminishing the innate immune response makes their inhibition a novel mechanism for reversing the immunosuppressive tumor microenvironment.

Regarding MerTK, the best-studied TAM RTK function is the role of MERTK in efferocytosis—the process by which apoptotic material is cleared by both monocyte-derived and epithelial cells. In macrophages, MERTK activation leads to engulfment of apoptotic material and suppression of the inflammatory cytokine response. During apoptotic cell ingestion, MERTK suppresses the M1 macrophage pro-inflammatory cytokine response (involving interleukin-12 (IL-12), IL-6 and tumor necrosis factor (TNF)), partly by diminishing nuclear factor-KB (NF-κB) signaling, and also enhances M2 macrophage anti-inflammatory cytokine production. MERTK signaling also alters macrophage gene expression, which suppresses inflammatory cytokine production and polarizes the macrophage towards a wound-healing, anti-inflammatory M2 phenotype. Thus, MERTK functions in macrophages to promote the rapid clearance of self antigens, to repair injured tissue and to suppress inflammation. When MERTK is eliminated or inhibited, apoptotic cells languish, which allows the proliferation of non-tolerant B cells, enhanced CD4+ T helper cells and the release of inflammatory cytokines. In tumor-associated macrophages, MERTK inhibition might therefore lead to enhanced anti-tumor immunity.

The tumor-associated macrophage and its less well-studied counterpart, the monocytoid myeloid-derived suppressor cell (MDSC), are derived from monocyte lineage cells that express little or no MERTK. However, in tissues, differentiated subsets induce the expression of MERTK. One major MERTK-expressing macrophage subtype, M2c, is differentiated in response to macrophage colony-stimulating factor (M-CSF; also known as CSF1). In the tumor microenvironment, continued MERTK activation by dying cells suppresses macrophage NF-κB signaling and the downstream induction of inflammatory cytokines (for example, IL-12 and IFNγ), and MERTK-mediated increases in IL-10 and GAS6 ensue. Inhibition of MerTK can alter the tumor microenvironment to a pro-inflammatory, tumor suppressive environment reducing the immunosuppressive nature of MDSCs.

Additionally, activated T cells induce the expression of PROS1 and externalize limited PtdSer patches on T cell membranes. This T cell-based ligand complex directly contacts innate immune cells, activating MERTK and turning down inflammatory cytokine production. Inhibition could lead to an immune-modulating effect promoting an M1 innate immune response, fueling a Th1 T cell response. The latter would supplement immune checkpoint (anti-CTLA4 or PD1) and tumor vaccine strategies.

Regarding Axl, dendritic cells, which are more dependent on AXL than on MERTK, provide feedback that helps to terminate inflammatory Toll-like receptor (TLR) signaling. In these antigen-presenting cells (APCs), TLR signaling results in activation of STAT1, which in turn induces AXL mRNA. AXL functions together with the type I interferon (IFN) receptor to increase suppressor of cytokine signaling 1 (SOCS1) and SOCS3 expression, which helps to terminate inflammatory TLR signaling. Axl inhibition could aid in restoring inflammatory TLR signaling.

Most patients with solid tumors die of metastatic disease rather than from the primary tumor. AXL in particular has been implicated in metastasis in multiple tumor types. First, AXL has a role in normal directed motility in the nervous system during the migration of gonadotropin-releasing hormone (GNRH)+ neurons to the hypothalamus. Second, in patient samples and cell lines, AXL expression correlates with migration and metastasis. Third, metastasis often requires epithelial-to-mesenchymal transition (EMT), which is facilitated by AXL. Canonical EMT-inducing gene products TWIST, SNAIL (also known as SNAI1) and SLUG (also known as SNAI2) are induced by AXL overexpression or through GAS6 stimulation. TWIST and SNAIL can also stimulate AXL expression, reinforcing EMT. Axl inhibition has been shown to reduce metastatic proliferation.

AXL also plays a well-established role in resistance to targeted therapeutics and examples of acquired resistance are currently limited to AXL. AXL is upregulated in imatinib-resistant CML and gastrointestinal stromal tumor (GIST) cell lines and tumor samples, and siRNA-mediated knockdown of AXL restored imatinib sensitivity to resistant cell lines. Similarly, AXL is induced in lapatinib-resistant HER2 (also known as ERBB2)-positive breast cancer cell lines, and AXL inhibition restored lapatinib sensitivity. AXL has been associated with acquired resistance to epidermal growth factor receptor (EGFR) TKIs and therapeutic antibodies in triple-negative breast cancer and head and neck cancer cell lines, as well as with resistance to inhibitors targeting other kinases, including fibroblast growth factor receptor (FGFR), anaplastic lymphoma kinase (ALK) and insulin-like growth factor 1 receptor (IGF1R). AXL is upregulated in NSCLC cell lines and xenografts that are resistant to EGFR TKIs and antibody drugs (cetuximab and erlotinib), and it is induced in 20% of matched tumor samples taken from patients with NSCLC after development of resistance to erlotinib (an EGFR TKI). The broad range of cancers studied, implicate AXL in drug resistance and suggest that AXL inhibition may have widely applicable utility and could re-sensitize tumors to targeted therapies.

Regarding MerTK and Axl dual inhibitors, the normal roles of MERTK and AXL in preventing or terminating innate immune-mediated inflammation and natural killer (NK) cell responses are subverted in the tumor microenvironment. MERTK and AXL decrease NK cell antitumor activity, which paradoxically allows increased metastases.

In addition, in solid tumors overexpression of AXL and MerTK promote chemoresistance. Therefore, targeting AXL allowed for increased potency of small molecule MerTK inhibitors, both on its ability to decrease the activation of MERTK and downstream effectors, as well its ability to decrease proliferation and colony formation. The cooperative relationship between MERTK and AXL, and coordinated regulation of expression has been demonstrated. Specifically, inhibition of either receptor increases expression of the other receptor. Additionally, MERTK and AXL are capable of physical interaction, suggesting that heterodimerization between MERTK and AXL may be a relevant mechanism of dual receptor activation. Targeting these two receptors concurrently provided synergistic decreases in oncogenic signaling, cell proliferation and colony formation.

Dual inhibition of MERTK and AXL may be a rational combination strategy that may have clinical utility against NSCLC and other solid tumors.

Regarding Pan TAM family inhibitors, much less is known about Tyro3 because it has been understudied. Using a 3-D spheroid assay to study the effect on motility, migration and invasion using a range of solid tumor cell lines, Pan TAM inhibition was very effective at inhibiting invasion and migration in the collagen culture.

SUMMARY OF THE INVENTION

The present invention is directed to selected pyrimidine compounds. The compounds may function as pan-TAM or Mer/Axl dual receptor tyrosine kinase inhibitors. Such compounds include compounds of Formula I or II:

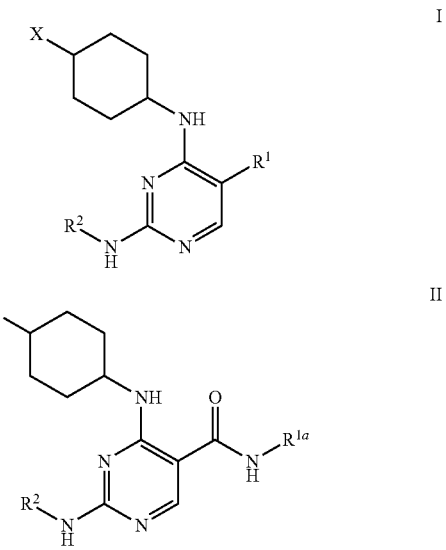

wherein:

X is —OH, —NH$_2$, —CH$_2$OH or —CH$_2$NH$_2$;

R$^1$ is substituted or unsubstituted aryl, substituted or unsubstituted heteroaryl, or substituted or unsubstituted cycloalkenyl, or substituted or unsubstituted heterocycloalkenyl;

R$^{1a}$ is substituted or unsubstituted alkyl, substituted or unsubstituted cycloalkyl, substituted or unsubstituted aryl, substituted or unsubstituted heteroaryl, substituted or unsubstituted alkylaryl, substituted or unsubstituted alkylheteroaryl, or substituted or unsubstituted alkylcycloalkyl;

R$^2$ is

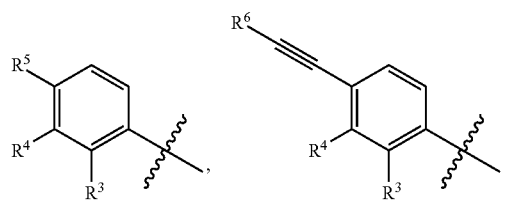

or substituted or unsubstituted heteroaryl;

R$^3$ and R$^4$ are each independently H, halo, lower alkyl or lower alkoxyl;

R$^5$ is H, halo, lower alkyl, lower alkoxyl, CN or SO$_2$Me; and

R$^6$ is substituted or unsubstituted heteroaryl, or a pharmaceutically acceptable salt thereof.

Such compounds also include compounds of Formula III or IV:

III

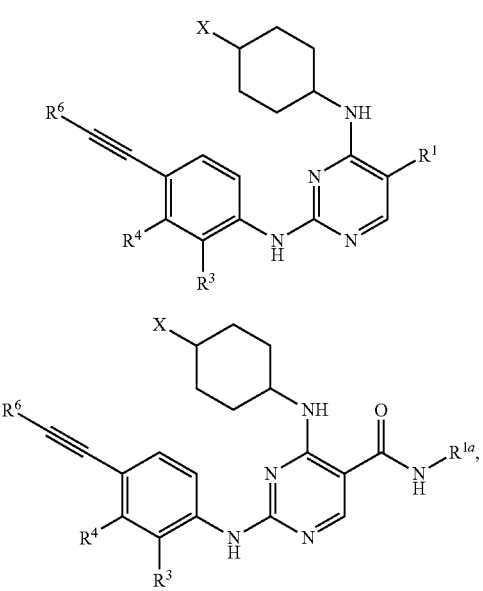

IV or a pharmaceutically acceptable salt thereof.

Such compounds may also include compounds of Formula V, VI, VII or VIII:

V

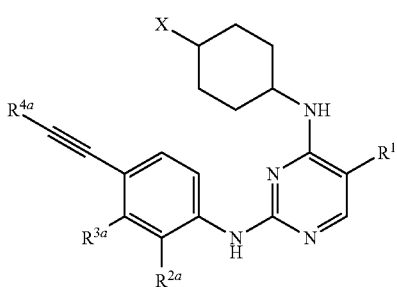

wherein:
X is —OH, —NH$_2$, —CH$_2$OH or —CH$_2$NH$_2$;
R$^1$ is H, substituted or unsubstituted aryl, substituted or unsubstituted heteroaryl, substituted or unsubstituted cycloalkenyl, or substituted or unsubstituted heterocycloalkenyl;
R$^{2a}$ and R$^{3a}$ are each independently H, halo, lower alkyl or lower alkoxyl; and
R$^{4a}$ is substituted or unsubstituted heteroaryl,

VI

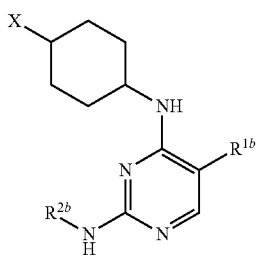

wherein:
X is —OH, —NH$_2$, —CH$_2$OH or —CH$_2$NH$_2$;
R$^{1b}$ is substituted or unsubstituted aryl, substituted or unsubstituted heteroaryl, or substituted or unsubstituted cycloalkenyl; and
R$^{2b}$ is

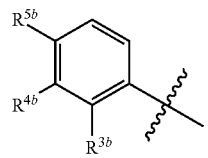

or substituted or unsubstituted heteroaryl;
R$^{3b}$, R$^{4b}$ is each independently —H, halo, lower alkyl or lower alkoxyl; and
R$^{5b}$ is —H, halo, lower alkyl, lower alkoxyl, —CN or —SO$_2$Me,

VII

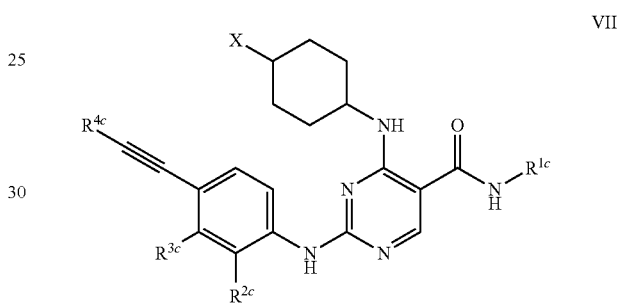

wherein:
X is —OH, —NH$_2$, —CH$_2$OH or —CH$_2$NH$_2$;
R$^{1c}$ is substituted or unsubstituted alkyl, substituted or unsubstituted cycloalkyl, substituted or unsubstituted aryl, substituted or unsubstituted heteroaryl, substituted or unsubstituted alkylaryl, substituted or unsubstituted alkylheteroaryl, or substituted or unsubstituted alkylcycloalkyl;
R$^{2c}$ and —R$^{3c}$ are each independently —H, halo, lower alkyl or lower alkoxyl; and
R$^{4c}$ is substituted or unsubstituted heteroaryl, or

VIII

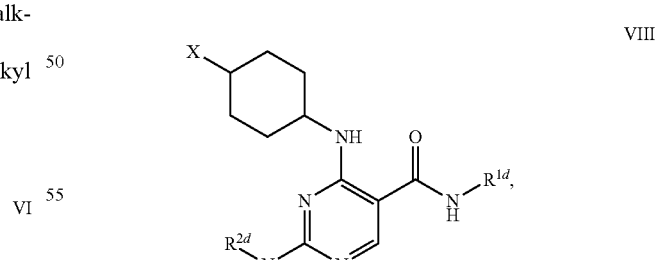

wherein:
X is —OH, —NH$_2$, —CH$_2$OH or —CH$_2$NH$_2$;
R$^{1d}$ is substituted or unsubstituted alkyl, substituted or unsubstituted cycloalkyl, substituted or unsubstituted aryl, substituted or unsubstituted heteroaryl, substituted or unsubstituted alkylaryl, substituted or unsubstituted alkylheteroaryl, or substituted or unsubstituted alkylcycloalkyl; and $R^{2d}$ is

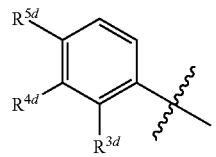

or substituted or unsubstituted heteroaryl;

$R^{3d}$ and $R^{4d}$ are each independently —H, halo, lower alkyl or lower alkoxyl; and $R^{5d}$ is —H, halo, lower alkyl, lower alkoxyl, —CN or —SO$_2$Me, or a pharmaceutically acceptable salt thereof.

Such compounds also include the specifically embodied compounds described herein or pharmaceutically acceptable salts thereof.

The present invention is further directed to use of the compounds described herein. The present invention includes a method of treating a cancer in a host which involves administering a compound of Formula I, II, III, IV, V, VI, VII, or VIII in a combination or alternation schedule with an immune checkpoint inhibitor.

In one embodiment, the immune checkpoint inhibitor is selected from a cytotoxic T-lymphocyte-associated protein 4 (CTLA4) inhibitor, a programmed cell death protein 1 (PD1) inhibitor, a programmed death-ligand 1 (PDL-1) inhibitor, or a combination thereof, and wherein for example the inhibitor can be an antibody such as ipilimumab, nivolumab or pembrolizumab. In one embodiment, a compound of Formula I, II, III, IV, V, VI, VII, or VIII and the immune checkpoint inhibitor combination is administered in further combination or alternation with ionizing radiation. In one embodiment, a compound of Formula I, II, III, IV, V, VI, VII, or VIII and the immune checkpoint inhibitor combination is administered in further combination or alternation with a Toll-like receptor (TLR) agonist, for example, but not limited to, monophosphoryl lipid A (MPL), *Mycobacterium bovis* (*Bacillus*-Calmette Guérin, BCG), CpG, ISCOMatrix, imiquimod (Aldera), Poly IC:LC, OK-432, and/or resiquimod. In one embodiment, a compound of Formula I, II, III, IV, V, VI, VII, or VIII and the immune checkpoint inhibitor combination is administered in further combination or alternation with both ionizing radiation and a TLR agonist.

The present invention also includes a method of treating a cancer in a host which involves administering an effective amount of Formula I, II, III, IV, V, VI, VII, or VIII in a combination or alternation schedule with a Toll-like receptor (TLR) agonist and/or radiation.

In another embodiment, a method of treating a cancer in a host is provided that includes administering to the host a therapeutically effective combination of a compound of Formula I, II, III, IV, V, VI, VII, or VIII and an immune checkpoint inhibitor, wherein the dose administered for either the compound Formula I, II, III, IV, V, VI, VII, or VIII or the immune checkpoint inhibitor, or both, is a subtherapeutic dose for the disorder being treated. In one embodiment, a compound of Formula I, II, III, IV, V, VI, VII, or VIII and immune checkpoint inhibitor combination is administered in further combination or alternation with ionizing radiation. In one embodiment, a compound of Formula I, II, III, IV, V, VI, VII, or VIII and immune checkpoint inhibitor combination is administered in further combination or alternation with a Toll-like receptor (TLR) agonist. In one embodiment, a compound of Formula I, II, III, IV, V, VI, VII, or VIII and immune checkpoint inhibitor combination is administered in further combination or alternation with both ionizing radiation and a TLR agonist.

In another embodiment, a method of treating a cancer in a host is provided that includes administering to the host a therapeutically effective combination of a compound of Formula I, II, III, IV, V, VI, VII, or VIII, or a pharmaceutically acceptable salt thereof, and an immune checkpoint inhibitor, a TLR agonist and/or ionizing radiation, In yet another embodiment, method of treating a cancer in a host is provided that includes administering to the host a therapeutically effective combination of, or a pharmaceutically acceptable salt thereof, and an immune checkpoint inhibitor, wherein the cancer is not responsive to immune checkpoint inhibitor monotherapy. In one embodiment, a compound of Formula I, II, III, IV, V, VI, VII, or VIII and immune checkpoint inhibitor combination is administered in further combination or alternation with ionizing radiation. In one embodiment, a compound of Formula I, II, III, IV, V, VI, VII, or VIII and immune checkpoint inhibitor combination is administered in further combination or alternation with a Toll-like receptor (TLR) agonist.

In yet a further embodiment, a method for treating specific cancers comprising administering to a host in need thereof a compound of Formula I, II, III, IV, V, VI, VII, or VIII in combination or alternation with an inhibitor that prevents the downregulation of the immune system (immune checkpoint inhibitor), wherein the administration of the combination results in an additive inhibitory effect in the cancer compared to the use of either a compound of Formula I, II, III, IV, V, VI, VII, or VIII alone or the immune checkpoint inhibitor alone. In one embodiment, a compound of Formula I, II, III, IV, V, VI, VII, or VIII and immune checkpoint inhibitor combination is administered in further combination or alternation with ionizing radiation. In one embodiment, a compound of Formula I, II, III, IV, V, VI, VII, or VIII and immune checkpoint inhibitor combination is administered in further combination or alternation with a Toll-like receptor (TLR) agonist. In one embodiment, a compound of Formula I, II, III, IV, V, VI, VII, or VIII and immune checkpoint inhibitor combination is administered in further combination or alternation with both ionizing radiation and a TLR agonist.

A compound of Formula I, II, III, IV, V, VI, VII, or VIII as described herein in combination with an immune checkpoint inhibitor may prevent the downregulation of the immune system and inhibit the proliferation and growth of certain cancers, including cancers that otherwise may not be responsive to immune downregulation inhibitor monotherapy. This may be achieved using a dose of a compound of Formula I, II, III, IV, V, VI, VII, or VIII that alone does not significantly inhibit the proliferation or growth of the cancer. That is, this result may be achieved with a subtherapeutic dose of the pan-TAM or MerTK/Axl inhibitor for the disorder being treated.

In one aspect of the present invention, a method for treating a specific cancer by administering to a host in need thereof a compound of Formula I, II, III, IV, V, VI, VII, or VIII in combination or alternation with a cytotoxic T-lymphocyte-associated 4 (CTLA4) immune checkpoint inhibitor, for example, an anti-CTLA-4 antibody, wherein the administration of the combination results in an additive inhibitory effect in the cancer compared to the use of either a compound of Formula I, II, III, IV, V, VI, VII, or VIII alone or the CTLA4 immune checkpoint inhibitor alone. In embodiments of the invention, the host is suffering from a cancer selected from colon cancer, prostate cancer, lung cancer, for example non-small cell lung carcinoma, melanoma, or breast cancer. In one embodiment, the host is suffering from a cancer that otherwise is not responsive to immune checkpoint inhibitor monotherapy, for example, but not limited to, certain colon cancers.

In further aspects of the invention, and without wanting to be bound by any specific theory, it is believed that the combination or alternation of ionizing radiation directed to a tumor further increases its immunicity due to the mechanism by which ionizing radiation kills the tumor cell. In this way, the use of ionizing radiation either before, during, or after administration of a compound of Formula I, II, III, IV, V, VI, VII, or VIII and immune checkpoint inhibitor combination therapy may increase the immunogenicity of the tumor allowing for a more robust anti-immunogenic effect in combination with a compound of Formula I, II, III, IV, V, VI, VII, or VIII/immune checkpoint inhibitor combination. In one aspect of the invention, as contemplated herein a compound of Formula I, II, III, IV, V, VI, VII, or VIII and immune checkpoint inhibitor combination is administered in further combination or alternation with ionizing radiation. In embodiments as contemplated herein, a compound of Formula I, II, III, IV, V, VI, VII, or VIII, immune checkpoint inhibitor, ionizing radiation combination is administered in further combination or alternation with a Toll-like receptor (TLR) agonist.

In further aspects of the invention, and without wanting to be bound by any specific theory, it is believed that the use of a TLR receptor agonist further increases the immunological affect directed towards the cancer cell, providing for a more robust anti-immunogenic effect in combination with a compound of Formula I, II, III, IV, V, VI, VII, or VIII. In embodiments, a compound of Formula I, II, III, IV, V, VI, VII, or VIII described herein is administered in combination or alternation with a TRL agonist. In certain embodiment, a compound of Formula I or Formula II and TRL agonist is administered in combination or alternation with an immune checkpoint inhibitor and/or ionizing radiation.

As contemplated herein, a compound of Formula I, II, III, IV, V, VI, VII, or VIII and immune checkpoint inhibitor can be administered in temporal combination or temporal alternation. For example, the two agents can be administered together or independently, for example by different routes such as, but not limited to, oral administration, intravenous administration, and injection. As described further below, a compound of Formula I, II, III, IV, V, VI, VII, or VIII and immune checkpoint inhibitor are administered such that the effect of the two agents overlap in vivo to create the advantageous effect. Likewise, the two active agents can be administered in temporal alternation instead of temporal combination (regardless of physical form of administration) as long as the effect of the two agents overlap in vivo to create the advantageous effect. Likewise, a compound of Formula I, II, III, IV, V, VI, VII, or VIII, immune checkpoint inhibitor, TLR agonist and/or ionizing radiation can be administered in temporal combination or temporal alternation.

As part of the invention, one or more of the compound of Formula I, II, III, IV, V, VI, VII, or VIII, in combination with an immune checkpoint inhibitor, can be used as adjunctive antineoplastic therapy for its immunostimulatory effect as a means to increase the efficacy of the antineoplastic standard of care therapies, such as chemotherapeutic compounds or ionizing radiation.

DETAILED DESCRIPTION

Figure 1A:
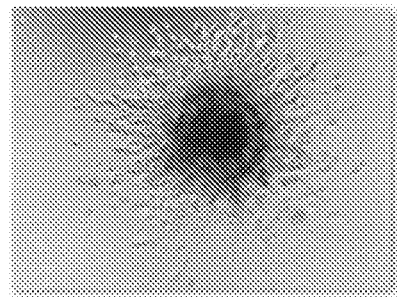
FIGS. 1A, 1B, 1C, and 1D show the growth of representative MDA-MB-231 spheroids after 24 hours in collagen culture after treatment with UNC1653. See Example 6.

Compounds are described using standard nomenclature. Unless defined otherwise, all technical and scientific terms used herein have the same meaning as is commonly understood by one of skill in the art to which this invention belongs.

The compounds in any of the Formulas described herein include enantiomers, mixtures of enantiomers, diastereomers, tautomers, racemates and other isomers, such as rotamers, as if each is specifically described.

The terms "a" and "an" do not denote a limitation of quantity, but rather denote the presence of at least one of the referenced item. The term "or" means "and/or". Recitation of ranges of values are merely intended to serve as a shorthand method of referring individually to each separate value falling within the range, unless otherwise indicated herein, and each separate value is incorporated into the specification as if it were individually recited herein. The endpoints of all ranges are included within the range and independently combinable. All methods described herein can be performed in a suitable order unless otherwise indicated herein or otherwise clearly contradicted by context. The use of examples, or exemplary language (e.g., "such as"), is intended merely to better illustrate the invention and does not pose a limitation on the scope of the invention unless otherwise claimed.

In one embodiment, the present invention includes compounds of Formula I, II, III, IV, V or VI, and the use of compounds with at least one desired isotopic substitution of an atom, at an amount above the natural abundance of the isotope, i.e., enriched. Isotopes are atoms having the same atomic number but different mass numbers, i.e., the same number of protons but a different number of neutrons.

Examples of isotopes that can be incorporated into compounds of the invention include isotopes of hydrogen, carbon, nitrogen, oxygen, phosphorous, fluorine, and chlorine, such as $^2H$, $^3H$, $^{11}C$, $^{13}c$, $^{14}C$, $^{15}N$, $^{18}F$ $^{31}P$, $^{32}P$, $^{35}S$, $^{36}Cl$, $^{125}I$ respectively. The invention includes various isotopically labeled compounds as defined herein, for example those into which radioactive isotopes, such as $^3H$, $^{13}C$, and $^{14}C$, are present. Such isotopically labelled compounds are useful in metabolic studies (with HC), reaction kinetic studies (with, for example $^2H$ or $^3H$), detection or imaging techniques, such as positron emission tomography (PET) or single-photon emission computed tomography (SPECT) including drug or substrate tissue distribution assays, or in radioactive treatment of patients. In particular, an $^{18}$F labeled compound may be particularly desirable for PET or SPECT studies. Isotopically labeled compounds of this invention and prodrugs thereof can generally be prepared by carrying out the procedures disclosed in the schemes or in the examples and preparations described below by substituting a readily available isotopically labeled reagent for a non-isotopically labeled reagent.

By way of general example and without limitation, isotopes of hydrogen, for example, deuterium ($^2$H) and tritium ($^3$H) may be used anywhere in described structures. Alternatively or in addition, isotopes of carbon, e.g., $^{13}$C and $^{14}$C, may be used. A typical isotopic substitution is deuterium for hydrogen at one or more locations on the molecule to improve the performance of the drug, for example, the pharmacodynamics, pharmacokinetics, biodistribution, half-life, stability, AUC, Tmax, Cmax, etc. For example, the deuterium can be bound to carbon in a location of bond breakage during metabolism (an α-deuterium kinetic isotope effect) or next to or near the site of bond breakage (a β-deuterium kinetic isotope effect).

Isotopic substitutions, for example deuterium substitutions, can be partial or complete. Partial deuterium substitution means that at least one hydrogen is substituted with deuterium. In certain embodiments, the isotope is 90, 95 or 99% or more enriched in an isotope at any location of interest. In one embodiment, deuterium is 90, 95 or 99% enriched at a desired location. Unless otherwise stated, the enrichment at any point is above natural abundance and enough to alter a detectable property of the drug in a human.

In one embodiment, the substitution of a hydrogen atom for a deuterium atom occurs within an R group when at least one of the variables within the R group is hydrogen (e.g., $^2$H or D) or alkyl (e.g., CD3). For example, when any of R groups are, or contain for example through substitution, methyl or ethyl, the alkyl residue is typically deuterated, e.g., CD$_3$, CH$_2$CD$_3$ or CD$_2$CD$_3$. In certain other embodiments, when any of the above mentioned R groups are hydrogen, the hydrogen may be isotopically enriched as deuterium (i.e., $^2$H).

A dash ("-") that is not between two letters or symbols is used to indicate a point of attachment for a substituent. For example, —(C=O)NH$_2$ is attached through carbon of the keto (C=O) group.

"Alkyl" as used herein alone or as part of another group, refers to a straight or branched chain hydrocarbon containing from 1 to 10 carbon atoms. In one embodiment, the alkyl contains from 1 to about 10 carbon atoms, more generally from 1 to about 6 carbon atoms or from 1 to about 4 carbon atoms. In certain embodiments, the alkyl is $C_1$-$C_3$ or $C_1$-$C_8$ The specified ranges as used herein indicate an alkyl group having each member of the range described as an independent species. For example, the term $C_1$-$C_3$ alkyl as used herein indicates a straight or branched alkyl group having from 1, 2, or 3 carbon atoms and is intended to mean that each of these is described as an independent species. For example, the term $C_1$-$C_3$alkyl as used herein indicates a straight or branched alkyl group having from 1, 2, or 3 carbon atoms and is intended to mean that each of these is described as an independent species. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, n-decyl, and the like. "Lower alkyl" as used herein, is a subset of alkyl, in some embodiments typically, and refers to a straight or branched chain hydrocarbon group containing from 1 to 4 carbon atoms. Representative examples of lower alkyl include, but are not limited to, methyl, ethyl, n-propyl, iso-propyl, n-butyl, iso-butyl, tert-butyl, and the like. The term "alkyl" or "loweralkyl" is intended to include both substituted and unsubstituted alkyl or loweralkyl unless otherwise indicated and these groups may be substituted with groups selected from halo (e.g., haloalkyl), alkyl, haloalkyl, hydroxyalkyl, alkenyl, alkynyl, cycloalkyl (including spiroalkyl, e.g., —C(CH$_2$)$_{2-4}$ spiroalkyl), cycloalkylalkyl, aryl, arylalkyl, heterocyclo, heterocycloalkyl, alkylheterocycloalkyl, heteroaryl, alkylheteroaryl, hydroxyl, alkoxy (thereby creating a polyalkoxy such as polyethylene glycol), alkenyloxy, alkynyloxy, haloalkoxy, cycloalkoxy, cycloalkylalkyloxy, aryloxy, arylalkyloxy, heterocyclooxy, heterocyclolalkyloxy, mercapto, alkyl-S(O),n, haloalkyl-S(O)$_m$, alkenyl-S(O)$_m$, alkynyl-S(O)$_m$, cycloalkyl-S(O)$_m$, cycloalkylalkyl-S(O)$_m$, aryl-S(O)$_m$, arylalkyl-S(O)$_m$, heterocyclo-S(O)$_m$, heterocycloalkyl-S(O)$_m$, amino, carboxy, alkylamino, —(CH$_2$)$_m$, —NH(CH$_2$)$_m$CH$_3$, —(CH$_2$)$_m$—NH(CH$_2$)$_m$OH, alkenylamino, alkynylamino, haloalkylamino, cycloalkylamino, cycloalkylalkylamino, arylamino, arylalkylamino, heterocycloamino, heterocycloalkylamino, disubstituted-amino, acylamino, acyloxy, ester, amide, sulfonamide, urea, alkoxyacylamino, aminoacyloxy, nitro or cyano where m=0, 1, 2 or 3. In one embodiment, alkyl or loweralkyl can be substituted with groups selected from a polar group, —(CH$_2$)$_m$—N(R$^{50}$)$_2$, —(CH$_2$)$_m$—NH(CH$_2$)$_m$R$^{50}$, —(CH$_2$)$_m$NH(CH$_2$)$_{2-3}$N(R$^{50}$)$_2$, —S(O)$_{20}$R$^{50}$, —CONHNHR$^{50}$, aminosulfonyl-C(CH$_2$)$_2$R$^{50}$ wherein each R$^{50}$ is independently selected from hydrogen, alkyl, alkenyl, alkynyl, aryl, arylalkyl, cycloalkyl, cycloalkylalkyl, heterocyclo, heterocycloalkyl, heteroaryl, or heteroarylalkyl.

"Alkenyl" as used herein alone or as part of another group, refers to a straight or branched chain hydrocarbon containing from 1 to 10 carbon atoms (or in loweralkenyl 1 to 4 carbon atoms) which include 1 to 4 double bonds in the normal chain. Representative examples of alkenyl include, but are not limited to, vinyl, 2-propenyl, 3-butenyl, 2-butenyl, 4-pentenyl, 3-pentenyl, 2-hexenyl, 3-hexenyl, 2,4-heptadiene, and the like. The term "alkenyl" or "loweralkenyl" is intended to include both substituted and unsubstituted alkenyl or loweralkenyl unless otherwise indicated and these groups may be substituted with groups as described in connection with alkyl and loweralkyl above.

"Alkynyl" as used herein alone or as part of another group, refers to a straight or branched chain hydrocarbon containing from 1 to 10 carbon atoms (or in loweralkynyl 1 to 4 carbon atoms) which include 1 triple bond in the normal chain. Representative examples of alkynyl include, but are not limited to, 2-propynyl, 3-butynyl, 2-butynyl, 4-pentynyl, 3-pentynyl, and the like. The term "alkynyl" or "loweralkynyl" is intended to include both substituted and unsubstituted alkynyl or loweralkynyl unless otherwise indicated and these groups may be substituted with the same groups as set forth in connection with alkyl and loweralkyl above.

"Cycloalkyl" as used herein alone or as part of another group, refers to a saturated or partially unsaturated cyclic hydrocarbon group containing from 3, 4 or 5 to 6, 7 or 8 carbons (which carbons may be replaced in a heterocyclic group as discussed below). Representative examples of cycloalkyl include, cyclopropyl, cyclobutyl, cyclopentyl, cyclohexyl, cycloheptyl, and cyclooctyl. These rings may be optionally substituted with additional substituents as described herein such as halo or loweralkyl. The term "cycloalkyl" is generic and intended to include heterocyclic groups as discussed below unless specified otherwise. In one embodiment, as used herein, the term "cycloalkyl" refers to a saturated or unsaturated hydrocarbon mono- or multi-ring, e.g., fused, bridged, or Spiro rings system having 3 to 15 carbon atoms (e.g., $C_3$-$C_{10}$). Examples of cycloalkyl include, but are not limited to, cyclopropyl, cyclobutyl, cyclopentyl, cyclohexyl, cycloheptyl, cyclooctyl, and adamantyl. In another embodiment, the term "cycloalkyl" refers to a saturated or partially unsaturated, monocyclic, fused bicyclic or bridged polycyclic ring assembly containing from 3 to 12 ring atoms, or the number of atoms indicated. Cycloalkyl can include any number of carbons, such as $C_{3-6}$, $C_{4-6}$, $C_{5-6}$, $C_{3-8}$, $C_{4-8}$, $C_{5-8}$, and $C_{6-8}$. Saturated monocyclic cycloalkyl rings include, for example, cyclopropyl, cyclobutyl, cyclopentyl, cyclohexyl, and cyclooctyl. Saturated bicyclic and polycyclic cycloalkyl rings include, for example, norbornane, [2.2.2]bicyclooctane, decahydronaphthalene and adamantane. Cycloalkyl groups can also be partially unsaturated, having one or more double bonds in the ring. Representative cycloalkyl groups that are partially unsaturated include, but are not limited to, cyclobutene, cyclopentene, cyclohexene, cyclohexadiene (1,3- and 1,4-isomers), cycloheptene, cycloheptadiene, cyclooctene, cyclooctadiene (1,3-, 1,4- and 1,5-isomers), norbornene, and norbornadiene. These groups may be substituted with groups as described in connection with alkyl and loweralkyl above.

"Heterocyclic group" or "heterocyclo" as used herein alone or as part of another group, refers to an aliphatic (e.g., fully or partially saturated heterocyclo) or aromatic (e.g., heteroaryl) monocyclic- or a bicyclic-ring system. In some embodiments, monocyclic ring systems are exemplified by any 7 membered ring containing 1, 2, 3, or 4 heteroatoms independently selected from oxygen, nitrogen and sulfur. Monocyclic ring systems are exemplified by any 5 or 6 membered ring containing 1, 2, 3, or 4 heteroatoms independently selected from oxygen, nitrogen and sulfur. The 5 membered ring has from 0-2 double bonds and the 6 membered ring has from 0-3 double bonds. Representative examples of monocyclic ring systems include, but are not limited to, azetidine, azepine, aziridine, diazepine, 1,3-dioxolane, dioxane, dithiane, furan, imidazole, imidazoline, imidazolidine, isothiazole, isothiazoline, isothiazolidine, isoxazole, isoxazoline, isoxazolidine, morpholine, oxadiazole, oxadiazoline, oxadiazolidine, oxazole, oxazoline, oxazolidine, piperazine, piperidine, pyran, pyrazine, pyrazole, pyrazoline, pyrazolidine, pyridine, pyrimidine, pyridazine, pyrrole, pyrroline, pyrrolidine, tetrahydrofuran, tetrahydrothiophene, tetrazine, tetrazole, thiadiazole, thiadiazoline, thiadiazolidine, thiazole, thiazoline, thiazolidine, thiophene, thiomorpholine, thiomorpholine sulfone, thiopyran, triazine, triazole, trithiane, and the like. Bicyclic ring systems are exemplified by any of the above monocyclic ring systems fused to an aryl group as defined herein, a cycloalkyl group as defined herein, or another monocyclic ring system as defined herein. Representative examples of bicyclic ring systems include but are not limited to, for example, benzimidazole, benzothiazole, benzothiadiazole, benzothiophene, benzoxadiazole, benzoxazole, benzofuran, benzopyran, benzothiopyran, benzodioxine, 1,3-benzodioxole, cinnoline, indazole, indole, indoline, indolizine, naphthyridine, isobenzofuran, isobenzothiophene, isoindole, isoindoline, isoquinoline, phthalazine, purine, pyranopyridine, quinoline, quinolizine, quinoxaline, quinazoline, tetrahydroisoquinoline, tetrahydroquinoline, thiopyranopyridine, and the like. These rings include quaternized derivatives thereof and may be optionally substituted with groups selected from halo, alkyl, haloalkyl, alkenyl, alkynyl, cycloalkyl, cycloalkylalkyl, aryl, arylalkyl, heterocyclo, heterocycloalkyl, hydroxyl, alkoxy, alkenyloxy, alkynyloxy, haloalkoxy, cycloalkoxy, cycloalkylalkyloxy, aryloxy, arylalkyloxy, heterocyclooxy, heterocyclolalkyloxy, mercapto, alkyl-S(O)$_m$, haloalkyl-S(O)$_m$, alkenyl-S(O)$_m$, alkynyl-S(O)$_m$, cycloalkyl-S(O)$_m$, cycloalkylalkyl-S(O)$_m$, aryl-S(O)$_m$, arylalkyl-S(O)$_m$, heterocyclo-S(O)$_m$, heterocycloalkyl-S(O)$_m$, amino, alkylamino, —(CH$_2$)$_m$—NH(CH$_2$)$_m$CH$_3$, —(CH$_2$)$_m$—NH(CH$_2$)$_m$OH alkenylamino, alkynylamino, haloalkylamino, cycloalkylamino, cycloalkylalkylamino, arylamino, arylalkylamino, heterocycloamino, heterocycloalkylamino, disubstituted-amino, acylamino, acyloxy, ester, amide, sulfonamide, urea, alkoxyacylamino, aminoacyloxy, nitro or cyano where m=0, 1, 2 or 3. In some embodiments, the heterocyclo groups can be substituted with groups as described in connection with alkyl and loweralkyl above. In another embodiment, the term "heterocyclo" refers to a saturated or unsaturated nonaromatic 3-8 membered monocyclic, 7-12 membered bicyclic (fused, bridged, or Spiro rings), or 11-14 membered tricyclic ring system (fused, bridged, or spiro rings) having one or more heteroatoms (such as O, N, or S), unless specified otherwise. Examples of heterocyclo groups include, but are not limited to, piperidinyl, piperazinyl, pyrrolidinyl, dioxanyl, tetrahydrofuranyl, isoindolinyl, indolinyl, imidazolidinyl, pyrazolidinyl, oxazolidinyl, isoxazolidinyl, triazolidinyl, tetrahydrofuranyl, oxiranyl, azetidinyl, oxetanyl, thietanyl, 1,2,3,6-tetrahydropyridinyl, tetrahydropyranyl, dihydropyranyl, pyranyl, morpholinyl, 1,4-diazepanyl, 1,4-oxazepanyl, 2-oxa-5-azabicyclo[2.2.1]heptanyl, 2,5-diazabicyclo[2.2.1] heptanyl, 2-oxa-6-azaspiro[3.3]heptanyl, 2,6-diazaspiro [3.3]heptanyl, 1,4-dioxa-8-azaspiro[4.5]decanyl and the like. These groups may be substituted with groups as described in connection with alkyl and loweralkyl above.

"Aryl" as used herein alone or as part of another group, refers to a monocyclic carbocyclic ring system or a bicyclic carbocyclic fused ring system having one or more aromatic rings. Representative examples of aryl include, azulenyl, indanyl, indenyl, naphthyl, phenyl, tetrahydronaphthyl, and the like. The term "aryl" is intended to include both substituted and unsubstituted aryl unless otherwise indicated and these groups may be substituted with the same groups as set forth in connection with alkyl and loweralkyl above.

"Arylalkyl" as used herein alone or as part of another group, refers to an aryl group, as defined herein, appended to the parent molecular moiety through an alkyl group, as defined herein. Representative examples of arylalkyl include, but are not limited to, benzyl, 2-phenylethyl, 3-phenylpropyl, 2-naphth-2-ylethyl, and the like.

"Heteroaryl" as used herein is as described in connection with heterocyclo above.

"Alkoxy" as used herein alone or as part of another group, refers to an alkyl or loweralkyl group, as defined herein (and thus including substituted versions such as polyalkoxy), appended to the parent molecular moiety through an oxy group, —O—. Representative examples of alkoxy include, but are not limited to, methoxy, ethoxy, propoxy, 2-propoxy, butoxy, tert-butoxy, pentyloxy, hexyloxy and the like.

"Halo" as used herein refers to any suitable halogen, including —F, —Cl, —Br, and —I.

"Mercapto" as used herein refers to an —SH group.

"Azido" as used herein refers to an —N$_3$ group.

"Cyano" as used herein refers to a —CN group.

"Formyl" as used herein refers to a —C(O)H group.

"Carboxylic acid" as used herein refers to a —C(O)OH group.

"Hydroxyl" as used herein refers to an —OH group.

"Nitro" as used herein refers to an —NO$_2$ group.

"Acyl" as used herein alone or as part of another group refers to a —C(O)R radical, where R is any suitable substituent such as aryl, alkyl, alkenyl, alkynyl, cycloalkyl or other suitable substituent as described herein.

"Alkylthio" as used herein alone or as part of another group, refers to an alkyl group, as defined herein, appended to the parent molecular moiety through a thio moiety, as defined herein. Representative examples of alkylthio include, but are not limited, methylthio, ethylthio, tert-butylthio, hexylthio, and the like.

"Amino" as used herein means the radical —NH$_2$.

"Alkylamino" as used herein alone or as part of another group means the radical —NHR, where R is an alkyl group.

"Arylalkylamino" as used herein alone or as part of another group means the radical —NHR, where R is an arylalkyl group.

"Disubstituted-amino" as used herein alone or as part of another group means the radical —NR$_a$R$_b$, where R$_a$ and R$_b$ are independently selected from the groups hydrogen, alkyl, haloalkyl, alkenyl, alkynyl, cycloalkyl, cycloalkylalkyl, aryl, arylalkyl, heterocyclo, heterocycloalkyl.

"Acylamino" as used herein alone or as part of another group means the radical —NR$_a$R$_b$, where R$_a$ is an acyl group as defined herein and R$_b$ is selected from the groups hydrogen, alkyl, haloalkyl, alkenyl, alkynyl, cycloalkyl, cycloalkylalkyl, aryl, arylalkyl, heterocyclo, heterocycloalkyl.

"Acyloxy" as used herein alone or as part of another group means the radical —OR, where R is an acyl group as defined herein.

"Ester" as used herein alone or as part of another group refers to a —C(O)OR radical, where R is any suitable substituent such as alkyl, cycloalkyl, alkenyl, alkynyl or aryl.

"Amide" as used herein alone or as part of another group refers to a —C(O)NR$_a$R$_b$ radical, where R$_a$ and R$_b$ are any suitable substituent such as alkyl, cycloalkyl, alkenyl, alkynyl or aryl. In some embodiments, R$_a$ and R$_b$ together with the nitrogen to which they are bonded form a heterocyclic ring.

"Sulfoxyl" as used herein refers to a compound of the formula —S(O)R, where R is any suitable substituent such as alkyl, cycloalkyl, alkenyl, alkynyl or aryl.

"Sulfonyl" as used herein refers to a compound of the formula —S(O)(O)R, where R is any suitable substituent such as amino, alkyl, cycloalkyl, alkenyl, alkynyl or aryl.

"Sulfonate" as used herein refers to a compound of the formula —S(O)(O)OR, where R is any suitable substituent such as alkyl, cycloalkyl, alkenyl, alkynyl or aryl.

"Sulfonic acid" as used herein refers to a compound of the formula —S(O)(O)OH.

"Sulfonamide" as used herein alone or as part of another group refers to a S(O)$_2$NR$_a$R$_b$ radical, where R$_a$ and R$_b$ are any suitable substituent such as H, alkyl, cycloalkyl, alkenyl, alkynyl or aryl. In some embodiments, R$_a$ and R$_b$ are any suitable substituent such as hydrogen, alkyl, alkenyl, alkynyl, aryl, arylalkyl, cycloalkyl, cycloalkylalkyl, heterocyclo, heterocycloalkyl, heteroaryl, or heteroarylalkyl and each R$_a$ and R$_b$ can be optionally substituted one, two or three times. In some embodiments, R$_a$ and R$_b$ together with the nitrogen to which they are bonded form a heterocyclic ring that can be optionally substituted one, two or three times.

"Urea" as used herein alone or as part of another group refers to an —N(R$_c$)C(O)NR$_a$R$_b$ radical, where R$_a$, R$_b$ and R$_c$ are any suitable substituent such as H, alkyl, cycloalkyl, alkenyl, alkynyl or aryl. In some embodiments, R$_a$ and R$_b$ together with the nitrogen to which they are bonded form a heterocyclic ring.

"Alkoxyacylamino" as used herein alone or as part of another group refers to an N(R$_a$)C(O)OR$_b$ radical, where R$_a$, R$_b$ are any suitable substituent such as H, alkyl, cycloalkyl, alkenyl, alkynyl or aryl.

"Aminoacyloxy" as used herein alone or as part of another group refers to an —OC(O)NR$_a$R$_b$ radical, where R$_a$ and R$_b$ are any suitable substituent such as H, alkyl, cycloalkyl, alkenyl, alkynyl or aryl. In some embodiments, R$_a$ and R$_b$ together with the nitrogen to which they are bonded form a heterocyclic ring.

"Optionally substituted" as used herein refers to the optionally substitution of a chemical moiety. These moieties can be substituted with groups selected from, but not limited to, halo (e.g., haloalkyl), alkyl, haloalkyl, hydroxyalkyl, alkenyl, alkynyl, cycloalkyl (including spiroalkyl, e.g., —C(CH$_2$)$_{2-4}$-spiroalkyl), cycloalkylalkyl, aryl, arylalkyl, aryl substituted heteroaryl, heterocyclo, heterocycloalkyl, alkylheterocycloalkyl, heteroaryl, heteroarylalkyl, hydroxyl, alkoxy (thereby creating a polyalkoxy such as polyethylene glycol), alkenyloxy, alkynyloxy, haloalkoxy, cycloalkoxy, cycloalkylalkyloxy, aryloxy, arylalkyloxy, heterocyclooxy, heterocyclolalkyloxy, mercapto, alkyl-S(O)$_m$, haloalkyl-S(O)$_m$, alkenyl S(O)$_m$, alkynyl-S(O)$_m$, cycloalkyl-S(O)$_m$, cycloalkylalkyl-S(O)$_m$, aryl-S(O)$_m$, arylalkyl-S(O)$_m$, heterocyclo-S(O)$_m$, heterocycloalkyl-S(O)$_m$, amino, carboxy, alkylamino, —(CH$_2$)$_m$—NH(CH$_2$)$_m$CH$_3$, —(CH$_2$)$_m$—NH(CH$_2$)$_m$OH, alkenylamino, alkynylamino, haloalkylamino, cycloalkylamino, cycloalkylalkylamino, arylamino, arylalkylamino, heterocycloamino, heterocycloalkylamino, disubstituted-amino, acylamino, acyloxy, ester, amide, sulfonamide, urea, alkoxyacylamino, aminoacyloxy, nitro, polar group or cyano where m=0, 1, 2 or 3. In one embodiment, alkyl or loweralkyl can be substituted with groups selected from a polar group, —(CH$_2$)$_m$—N(R$^{50}$)$_2$, —(CH$_2$)$_m$—NH(CH$_2$)$_m$R$^{50}$, —(CH$_2$)$_m$NH(CH$_2$)$_{2-3}$N(R$^{50}$)$_2$, —S(O)$_{20}$R$^{50}$, —CONHNHR$^{50}$, aminosulfonyl —C(CH$_2$)$_2$R$^{50}$ wherein each R$^{50}$ is independently selected from hydrogen, alkyl, alkenyl, alkynyl, aryl, arylalkyl, cycloalkyl, cycloalkylalkyl, heterocyclo, heterocycloalkyl, heteroaryl, or heteroarylalkyl.

"Polar group" as used herein refers to a group wherein the nuclei of the atoms covalently bound to each other to form the group do not share the electrons of the covalent bond(s) joining them equally; that is the electron cloud is denser about one atom than another. This results in one end of the covalent bond(s) being relatively negative and the other end relatively positive; i.e., there is a negative pole and a positive pole. Examples of polar groups include, without limitations, halo, hydroxy, alkoxy, carboxy, nitro, cyano, amino (primary, secondary and tertiary), amido, ureido, sulfonamido, sulfinyl, sulfhydryl, silyl, S-sulfonamido, N-sulfonamido, C-carboxy, O-carboxy, C-amido, N-amido, sulfonyl, N-tert-butoxycarbonyl (or "t-BOC") groups, phosphono, morpholino, piperazinyl, tetrazolo, and the like. See, e.g., U.S. Pat. No. 6,878,733, as well as alcohol, thiol, polyethylene glycol, polyol (including sugar, aminosugar, uronic acid), sulfonamide, carboxamide, hydrazide, N-hydroxycarboxamide, urea, metal chelates (including macrocyclic ligand or crown ether metal chelates). The polar group can be an ionic group.

"Ionic group" as used herein includes anionic and cationic groups, and includes groups (sometimes referred to as "ionogenic" groups) that are uncharged in one form but can be easily converted to ionic groups (for example, by protonation or deprotonation in aqueous solution). Examples include but are not limited to carboxylate, sulfonate, phosphate, amine, N-oxide, and ammonium (including quaternized heterocyclic amines such as imidazolium and pyridinium) groups. See, e.g., U.S. Pat. Nos. 6,478,863; 6,800,276; and 6,896,246. Additional examples include uronic acids, carboxylic acid, sulfonic acid, amine, and moieties such as guanidinium, phosphoric acid, phosphonic acid, phosphatidyl choline, phosphonium, borate, sulfate, etc.

"Deuterium" as used herein alone or as part of another group, refers to $^2$H, which has one proton and one neutron in the nucleus. It is a safe, non-radioactive isotope of hydrogen. Any hydrogen in a group or substituent described above may be replaced with deuterium to provide a "deuterated" compound, in some embodiments to modify and/or improve metabolic stability, resulting in better safety, tolerability and/or efficacy.

"Treat" as used herein refers to any type of treatment that imparts a benefit to a patient afflicted with a disease, including improvement in the condition of the patient (e.g., in one or more symptoms), delay in the progression of the disease, delay in onset of the disease, etc.

"Pharmaceutically acceptable" as used herein means that the compound or composition is suitable for administration to a subject to achieve the treatments described herein, without unduly deleterious side effects in light of the severity of the disease and necessity of the treatment.

A "dosage form" means a unit of administration of an active agent. Examples of dosage forms include tablets, capsules, injections, suspensions, liquids, emulsions, implants, particles, spheres, creams, ointments, suppositories, inhalable forms, transdermal forms, buccal, sublingual, topical, gel, mucosal, and the like.

"Pharmaceutical compositions" are compositions comprising at least one active agent, such as a compound or salt of Formula I, II, III, IV, V, VI, VII or VIII and at least one other substance, such as a carrier. "Pharmaceutical combinations" are combinations of at least two active agents which may be combined in a single dosage form or provided together in separate dosage forms with instructions that the active agents are to be used together to treat any disorder described herein.

"Pharmaceutically acceptable salts" includes derivatives of the disclosed compounds in which the parent compound is modified by making inorganic and organic, non-toxic, acid or base addition salts thereof. The salts of the present compounds can be synthesized from a parent compound that contains a basic or acidic moiety by conventional chemical methods. Generally, such salts can be prepared by reacting free acid forms of these compounds with a stoichiometric amount of the appropriate base (such as Na, Ca, Mg, or K hydroxide, carbonate, bicarbonate, or the like), or by reacting free base forms of these compounds with a stoichiometric amount of the appropriate acid. Such reactions are typically carried out in water or in an organic solvent, or in a mixture of the two. Generally, non-aqueous media like ether, ethyl acetate, ethanol, isopropanol, or acetonitrile are typical, where practicable. Salts of the present compounds further include solvates of the compounds and of the compound salts.

Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts and the quaternary ammonium salts of the parent compound formed, for example, from non-toxic inorganic or organic acids. For example, conventional non-toxic acid salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, mesylic, esylic, besylic, sulfanilic, 2-acetoxybenzoic, fumaric, toluenesulfonic, methanesulfonic, ethane disulfonic, oxalic, isethionic, HOOC—$(CH_2)_n$—COOH where n is 0-4, and the like. Lists of additional suitable salts may be found, e.g., in *Remington's Pharmaceutical Sciences*, 17th ed., Mack Publishing Company, Easton, Pa., p. 1418 (1985).

The term "carrier" applied to pharmaceutical compositions/combinations of the invention refers to a diluent, excipient, or vehicle with which an active compound is provided.

A "pharmaceutically acceptable excipient" means an excipient that is useful in preparing a pharmaceutical composition/combination that is generally safe, non-toxic and neither biologically nor otherwise inappropriate for administration to a host, and includes, in one embodiment, an excipient that is acceptable for veterinary use as well as human pharmaceutical use. A "pharmaceutically acceptable excipient" as used in the present application includes both one and more than one such excipient.

Compounds of the present invention may optionally be administered in conjunction with other compounds. The other compounds may optionally be administered concurrently. As used herein, the word "concurrently" means sufficiently close in time to produce a combined effect (that is, concurrently may be simultaneously, or it may be two or more events occurring within a short time period before or after each other).

"Immune checkpoint" as used herein refers to a molecule on the cell surface of a CD4 and CD8 T cell that down-modulates or inhibits an anti-tumor immune response. Immune checkpoint molecules include, but are not limited to, Programmed Death 1 (PD1), Cytotoxic T-Lymphocyte Antigen 4 (CTLA-4), PDL-1 (B7H1), PDL-2 (B7-DC), B7H3, B7H4, OX-40, CD137, CD40, CD27, LAG3, TIM3, ICOS, or BTLA, which directly inhibit immune cells. Immunotherapeutic agents which can act as immune checkpoint inhibitors useful in the methods of the present invention include, but are not limited to, anti-PD1; anti-CTLA-4; anti-PDL-1; anti-B7-H1; anti-PDL-2; anti-B7-H3; anti-B7-H4; anti-CD137; anti-CD40; anti-CD27; anti-LAG3; anti-TIM3; anti-ICOS, and anti-BTLA.

The term "subtherapeutic dose" as used herein refers to a dose that is below the effective monotherapy dosage levels for the disorder being treated in the host being treated. In one nonlimiting embodiment, the subtherapeutic dose of the compound of Formula I, II, III, IV, V, VI, VII, or VIII does not substantially affect the growth of the cancer or tumor being treated when administered alone. In an alternative nonlimiting embodiment, the subtherapeutic dose of an immune checkpoint inhibitor does not substantially affect the growth of the cancer or tumor being treated when administered alone.

As used herein the term "ionizing radiation" refers to radiation of sufficient energy that, when absorbed by cells and tissues, can induce formation of reactive oxygen species and DNA damage. Ionizing radiation can include X-rays, gamma rays, and particle bombardment (e.g., neutron beam, electron beam, protons, mesons, and others). Radiation is generally measured in units of absorbed dose, such as the rad or gray (Gy), or in units of dose equivalence, such as rem or sievert (Sv).

"Subjects" as used herein are generally human subjects and include, but are not limited to, "patients" or "hosts." The subjects may be male or female and may be of any race or ethnicity, including, but not limited to, Caucasian, African-American, African, Asian, Hispanic, Indian, etc. The subjects may be of any age, including newborn, neonate, infant, child, juvenile, adolescent, adult, and geriatric. Subjects may also include animal subjects, particularly mammalian subjects such as canines, felines, bovines, caprines, equines, ovines, porcines, rodents (e.g. rats and mice), lagomorphs, primates (including non-human primates), etc., for prevention and treatment purposes as well as veterinary medicine and/or pharmaceutical screening and/or drug development purposes.

1. Active Compounds.

The present invention provides active compounds of Formula I, II, III, IV, V, VI, VII and VIII.

Compounds of Formula I or II:

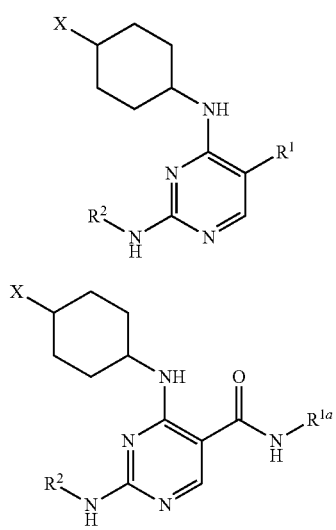

wherein:

X is —OH, —NH$_2$, —CH$_2$OH or —CH$_2$NH$_2$;

R$^1$ is substituted or unsubstituted aryl, substituted or unsubstituted heteroaryl, or substituted or unsubstituted cycloalkenyl, or substituted or unsubstituted heterocycloalkenyl;

R$^{1a}$ is substituted or unsubstituted alkyl, substituted or unsubstituted cycloalkyl, substituted or unsubstituted aryl, substituted or unsubstituted heteroaryl, substituted or unsubstituted alkylaryl, substituted or unsubstituted alkylheteroaryl, or substituted or unsubstituted alkylcycloalkyl;

R$^2$ is

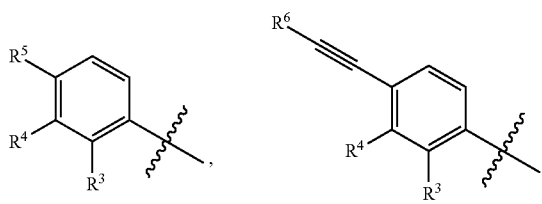

or substituted or unsubstituted heteroaryl;

R$^3$ and R$^4$ are each independently H, halo, lower alkyl or lower alkoxyl;

R$^5$ is H, halo, lower alkyl, lower alkoxyl, CN or SO$_2$Me; and

R$^6$ is substituted or unsubstituted heteroaryl, or a pharmaceutically acceptable salt thereof.

Compounds of Formula III or IV:

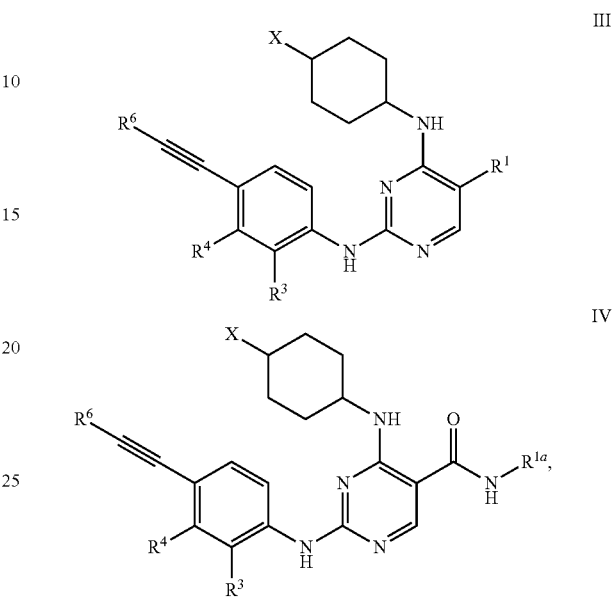

or a pharmaceutically acceptable salt thereof.

Compounds of Formula V, VI, VII or VIII:

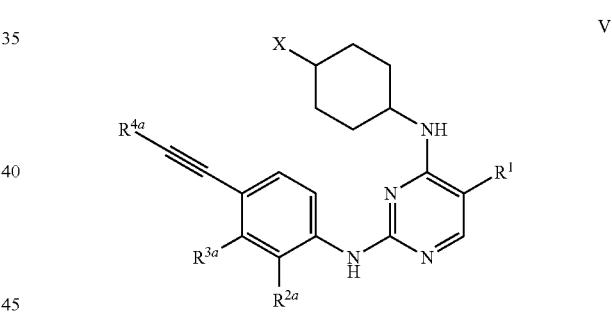

wherein:

X is —OH, —NH$_2$, —CH$_2$OH or —CH$_2$NH$_2$;

R$^1$ is H, substituted or unsubstituted aryl, substituted or unsubstituted heteroaryl, substituted or unsubstituted cycloalkenyl, or substituted or unsubstituted heterocycloalkenyl;

R$^{2a}$ and R$^{1a}$ are each independently H, halo, lower alkyl or lower alkoxyl; and R$^{4a}$ is substituted or unsubstituted heteroaryl,

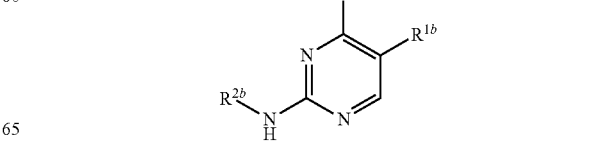

wherein:

X is —OH, —NH$_2$, —CH$_2$OH or —CH$_2$NH$_2$;

R$^{1b}$ is substituted or unsubstituted aryl, substituted or unsubstituted heteroaryl, or substituted or unsubstituted cycloalkenyl; and R$^{2b}$ is

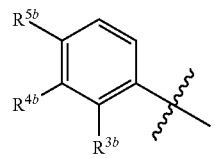

or substituted or unsubstituted heteroaryl;

R$^{3b}$, R$^{4b}$ is each independently —H, halo, lower alkyl or lower alkoxyl; and R$^{5b}$ is —H, halo, lower alkyl, lower alkoxyl, —CN or —SO$_2$Me,

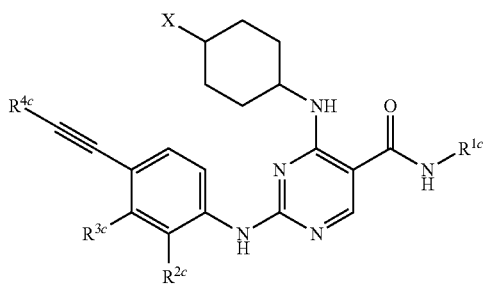

VII wherein:

X is —OH, —NH$_2$, —CH$_2$OH or —CH$_2$NH$_2$;

R$^{1c}$ is substituted or unsubstituted alkyl, substituted or unsubstituted cycloalkyl, substituted or unsubstituted aryl, substituted or unsubstituted heteroaryl, substituted or unsubstituted alkylaryl, substituted or unsubstituted alkylheteroaryl, or substituted or unsubstituted alkylcycloalkyl;

R$^{2c}$ and —R$^{3c}$ are each independently —H, halo, lower alkyl or lower alkoxyl; and R$^{4c}$ is substituted or unsubstituted heteroaryl, or

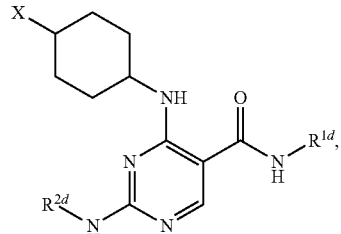

VIII wherein:

X is —OH, —NH$_2$, —CH$_2$OH or —CH$_2$NH$_2$;

R$^{1d}$ is substituted or unsubstituted alkyl, substituted or unsubstituted cycloalkyl, substituted or unsubstituted aryl, substituted or unsubstituted heteroaryl, substituted or unsubstituted alkylaryl, substituted or unsubstituted alkylheteroaryl, or substituted or unsubstituted alkylcycloalkyl; and R$^{2d}$ is

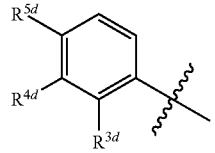

or substituted or unsubstituted heteroaryl;

R$^{3d}$ and R$^{4d}$ are each independently —H, halo, lower alkyl or lower alkoxyl; and R$^{5d}$ is —H, halo, lower alkyl, lower alkoxyl, —CN or —SO$_2$Me, or a pharmaceutically acceptable salt thereof.

More particular examples of compounds of the present invention include but are not limited to those set forth in Tables 1-5 below and the following:

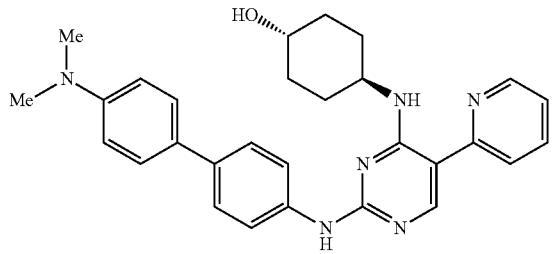

UNC4436A

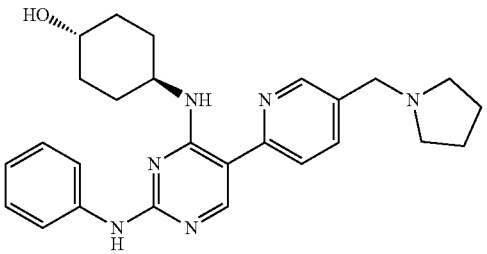

UNC4198A

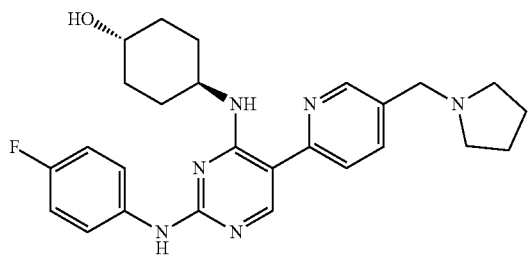

UNC4241A

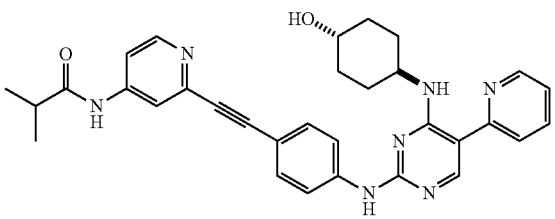

UNC4042A

-continued

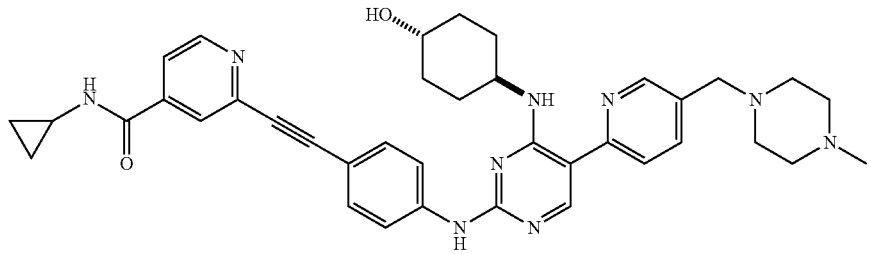
UNC3319A

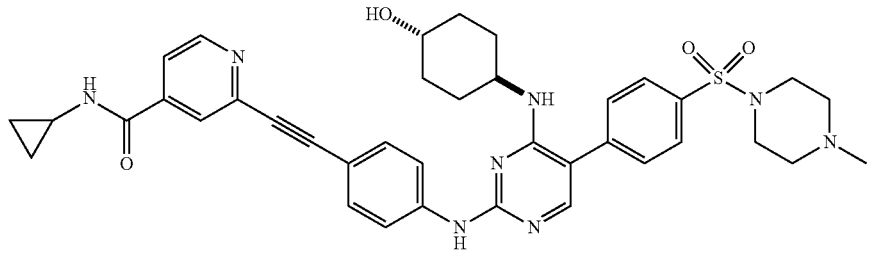
UNC3397A

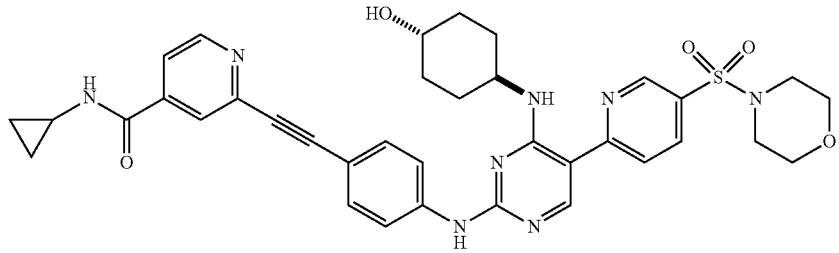
UNC3399A

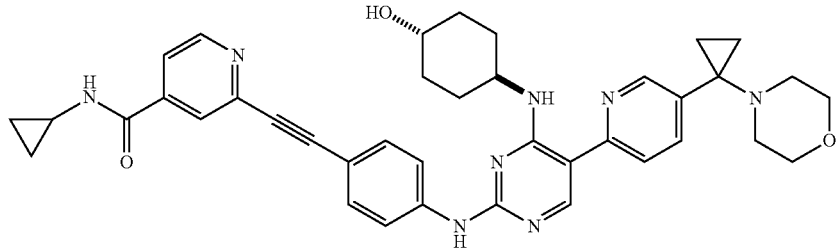
UNC3632A

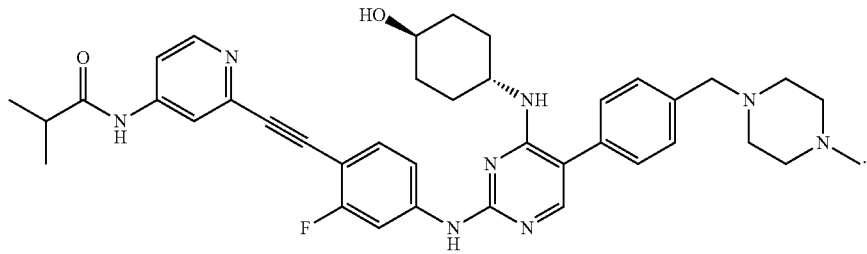
UNC4045A

The compounds described herein include enantiomers, mixtures of enantiomers, diastereomers, tautomers, racemates and other isomers, such as rotamers, as if each is specifically described. In some embodiments, the compounds include a cis-stereoisomer thereof.

The active compounds disclosed herein can, as noted above, be provided in the form of their pharmaceutically acceptable salts. Pharmaceutically acceptable salts are salts that retain the desired biological activity of the parent compound and do not impart undesired toxicological effects. Examples of such salts are (a) acid addition salts formed with inorganic acids, for example hydrochloric acid, hydrobromic acid, sulfuric acid, phosphoric acid, nitric acid and the like; and salts formed with organic acids such as, for example, acetic acid, oxalic acid, tartaric acid, succinic acid, maleic acid, fumaric acid, gluconic acid, citric acid, malic acid, ascorbic acid, benzoic acid, tannic acid, palmitic acid, alginic acid, polyglutamic acid, naphthalenesulfonic acid, methanesulfonic acid, p-toluenesulfonic acid, naphthalene-disulfonic acid, polygalacturonic acid, and the like; (b) salts formed from elemental anions such as chlorine, bromine, and iodine, and (c) salts derived from bases, such as ammonium salts, alkali metal salts such as those of sodium and potassium, alkaline earth metal salts such as those of calcium and magnesium, and salts with organic bases such as dicyclohexylamine and N-methyl-D-glucamine.

Active compounds as described herein can be prepared in accordance with known procedures, or variations thereof that will be apparent to those skilled in the art.

Active compounds may be provided as pharmaceutically acceptable prodrugs, which are, within the scope of sound medical judgment, suitable for use in contact with the tissues of humans and lower animals without undue toxicity, irritation, allergic response and the like, commensurate with a reasonable risk/benefit ratio, and effective for their intended use, as well as the zwitterionic forms, where possible, of the compounds of the invention.

The term "prodrug" refers to compounds that are transformed, sometimes rapidly in vivo to yield the parent compound of the above formulae, for example, by hydrolysis intracellularly or extracellularly, for example, in blood. A thorough discussion is provided in T. Higuchi and V. Stella, Prodrugs as Novel delivery Systems, Vol. 14 of the A.C.S. Symposium Series and in Edward B. Roche, ed., Bioreversible Carriers in Drug Design, American Pharmaceutical Association and Pergamon Press, 1987, both of which are incorporated by reference herein. See also U.S. Pat. No. 6,680,299. Examples include a prodrug that is metabolized in vivo by a subject to an active drug having an activity of a compound as described herein, wherein the prodrug is an ester of an alcohol or carboxylic acid group, if such a group is present in the compound; an acetal or ketal of an alcohol group, if such a group is present in the compound; an N-Mannich base or an imine of an amine group, if such a group is present in the compound; or a Schiff base, oxime, acetal, enol ester, oxazolidine, or thiazolidine of a carbonyl group, if such a group is present in the compound, such as described in U.S. Pat. Nos. 6,680,324 and 6,680,322.

The pan-TAM kinase and MerTK/AXL inhibitors for use in the present invention as contemplated herein can, as noted above, be provided in the form of a pharmaceutically acceptable salt. Pharmaceutically acceptable salts are salts that retain the desired biological activity of the parent compound and do not impart an undesired toxicological effect. Nonlimiting examples of such salts are (a) acid addition salts formed with inorganic acids, for example hydrochloric acid, hydrobromic acid, sulfuric acid, phosphoric acid, nitric acid and the like; and salts formed with organic acids such as, for example, acetic acid, oxalic acid, tartaric acid, succinic acid, maleic acid, fumaric acid, gluconic acid, citric acid, malic acid, ascorbic acid, benzoic acid, tannic acid, palmitic acid, alginic acid, polyglutamic acid, naphthalenesulfonic acid, methanesulfonic acid, p-toluenesulfonic acid, naphthalenedisulfonic acid, polygalacturonic acid, and the like; (b) salts formed from elemental anions such as chlorine, bromine, and iodine, and (c) salts derived from bases, such as ammonium salts, alkali metal salts such as those of sodium and potassium, alkaline earth metal salts such as those of calcium and magnesium, and salts with organic bases such as dicyclohexylamine and N-methyl-D-glucamine.

Immune Checkpoint Inhibitors

An immune checkpoint molecule is one that is capable of inhibiting or downmodulating an immune response to a tumor or cancer. An inhibitor of an immune checkpoint molecule is a small molecule (pharmaceutical) or large molecule (biologic) capable of turning off the down regulation of the immune system to the tumor or cancer. Examples of immune checkpoint inhibitors useful for administration in combination with the pan-TAM kinase and/or MerTK/AXL inhibitors described herein include inhibitors of CTLA4, PD1, PDL-1, B7H1, B7H3, B7H4, OX-40, CD137, CD40, CD27, LAG3, TIM3, ICOS, or BTLA, including antibodies to these proteins.

In one embodiment, the immune checkpoint inhibitor is a CTLA4 inhibitor. Cytotoxic T-lymphocyte antigen 4 (CTLA4, also known as CD152) is a member of the immunoglobulin superfamily that is expressed exclusively on T-cells. CTLA4 acts to inhibit T-cell activation and is reported to inhibit helper T-cell activity and enhance regulatory T-cell immunosuppressive activity. Some anti-CTLA4 antibodies have been approved for the treatment of melanoma, prostate cancer, small cell lung cancer, non-small cell lung cancer (Pardoll, D. "The blockade of immune checkpoints in cancer immunotherapy." 2012, Nature Reviews Cancer 12:252-264), and others have shown efficacy in clinical trials.

Non-limiting examples of anti-CTLA4 antibodies which can be used herein include ipilimumab (Yervoy®, MDX-010, Bristol-Myers Squibb) and tremelimumab (CP-675206, Pfizer).

In one embodiment, the immune checkpoint inhibitor is a PD-1 inhibitor. Programmed cell death protein 1 (PD1, also known as CD279) is a cell surface membrane protein of the immunoglobulin superfamily. The major role of PD1 is to limit the activity of T cells in peripheral tissues during inflammation in response to infection, as well as to limit autoimmunity. PD1 expression is induced in activated T cells and binding of PD1 to one of its endogenous ligands acts to inhibit T-cell activation by inhibiting stimulatory kinases. PD1 is highly expressed on $T_{reg}$ cells and may increase their proliferation in the presence of ligand (Pardoll, D. "The blockade of immune checkpoints in cancer immunotherapy." 2012, Nature Reviews Cancer 12:252-264).

Non-limiting examples of anti-PD1 antibodies contemplated for use herein include, but are not limited to, pembrolizumab (Keytruda®, MK-3475, formerly lambrolizumab, Merck), nivolumab (Opdivo®, BMS-936558, Bristol-Myers Squibb), AMP-224 (Merck), pidilizumab (CT-011, Curetech), and MEDI0680/AMP-514 (Astrazeneca/MedImmune).

Other immune checkpoint inhibitors that may be used including, for example, immune checkpoint inhibitors targeting PDL-1 (B7H1), PDL-2 (B7-DC), B7H3, B7H4, OX-40, CD137, CD40, CD27, LAG3, TIM3, ICOS, or BTLA (Pardoll, 2012, Nature Reviews Cancer 12:252-264).

In one embodiment, the immune checkpoint inhibitor is selected from the group consisting of a PDL-1 inhibitor, B7H1 inhibitor, B7H3 inhibitor, B7H4 inhibitor, OX-40 inhibitor, CD137 inhibitor, CD40 inhibitor, CD27 inhibitor, LAG3 inhibitor, TIM3 inhibitor, ICOS inhibitor, or BTLA inhibitor.

In one embodiment, the immune checkpoint inhibitor is a PDL-1 inhibitor. PDL-1 is expressed on cancer cells and causes the immune response shut down. Non-limiting examples of PDL-1 inhibitors that are useful in the present invention include MPDL3280A (Roche/Genentech), MEDI4736 (AstraZeneca/MedImmune), BMS-936559 (Bristol-Myers Squibb), and avelumab (MSB0010718; Merck/Pfizer). MPDL3280A (Roche/Genentech) has entered clinical trials for bladder cancer, non-small cell lung cancer, melanoma, kidney cancer, lymphoma, and solid tumors. MEDI4736 (AstraZeneca/MedImmune) is in clinical trials for a number of cancers, including brain, cervical, colorectal, head and neck, kidney, lung, and ovarian cancers.

In one embodiment, the immune checkpoint inhibitor is a 4-1BB inhibitor. 4-1BB, also known as CD137, is a costimulator for activated T cells. Non-limiting examples of 4-1BB inhibitors contemplated herein include urelumab (BMS-663513, Bristol-Myers Squibb) and PF-05082566 (PF-2566, Pfizer).

In one embodiment, the immune checkpoint inhibitor is a LAG-3 inhibitor. Non-limiting examples of LAG-3 inhibitors contemplated for use herein include BMS-986016 and IMP321. A LAG-3 antibody (BMS-986016, Bristol-Myers Squibb) is being tested in patients with hematological and solid cancers. IMP321 (Prima BioMed) is a soluble version of the LAG3 molecule.

In one embodiment, the immune checkpoint inhibitor is a CD27 inhibitor. The CD27 costimulatory molecule plays an important role in the activation, survival, and differentiation of T cells. One non-limiting example of an CD27 inhibitor contemplated for use herein is varlilumab (CDX-1127, Celldex) and is being tested in B cell cancers, T cell cancers, and solid tumors, including melanoma, kidney cancer, prostate cancer, ovarian cancer, colorectal cancer, and lung cancer.

In one embodiment, the immune checkpoint inhibitor is a CD40 inhibitor. CD40 is an activating protein on the surface of B cells and activates dendritic cells to promote CD8+ T cell activation and proliferation. One non-limiting example of a CD40 inhibitor contemplated for use herein includes CP-870,893 (Pfizer) and is being tested for pancreatic cancer.

In one embodiment, the immune checkpoint inhibitor is a B7-H3 inhibitor. One non-limiting example of a B7-H3 inhibitor contemplated for use herein is MGA271. MGA271 (Macrogenics) entered clinical trials for multiple cancers.

Toll-Like Receptor (TLR) Agonists

Toll-like receptors (TLRs) play a vital role in activating immune responses. TLRs recognize conserved pathogen-associated molecular patterns (PAMPs) expressed in a wide array of microbes, as well as endogenous damage-associated molecular patterns (DAMPs) released from stressed or dying cells. There has been a major effort in recent years, with significant success, to discover new drug compounds that act by stimulating certain key aspects of the immune system, as well as by suppressing certain other aspects (see, e.g., U.S. Pat. Nos. 6,039,969 and 6,200,592). These compounds appear to act through basic immune system mechanisms known as Toll-like receptors (TLRs) and are referred to herein as "TLR agonists."

Many TLR agonists are small organic molecule imidazoquinoline amine derivatives (see, e.g., U.S. Pat. No. 4,689,338), but a number of other compound classes are known as well (see, e.g., U.S. Pat. Nos. 5,446,153; 6,194,425; and 6,110,929; and International Publication Number WO 2005/079195) and more are still being discovered. Other IRMs have higher molecular weights, such as oligonucleotides, including CpGs (see, e.g., U.S. Pat. No. 6,194,388).

TLR agonists are known in the art and include small organic molecules (e.g., molecular weight under about 1000 Daltons, preferably under about 500 Daltons, as opposed to large biological molecules such as proteins, peptides, and the like) such as those disclosed in, for example, U.S. Pat. Nos. 4,689,338; 4,929,624; 5,266,575; 5,268,376; 5,346,905; 5,352,784; 5,389,640; 5,446,153; 5,482,936; 5,756,747; 6,110,929; 6,194,425; 6,331,539; 6,376,669; 6,451,810; 6,525,064; 6,541,485; 6,545,016; 6,545,017; 6,573,273; 6,656,938; 6,660,735; 6,660,747; 6,664,260; 6,664,264; 6,664,265; 6,667,312; 6,670,372; 6,677,347; 6,677,348; 6,677,349; 6,683,088; 6,756,382; 6,797,718; 6,818,650; and 7,7091,214; U.S. Patent Publication Nos. 2004/0091491, 2004/0176367, and 2006/0100229; and International Publication Nos. WO 2005/18551, WO 2005/18556, WO 2005/20999, WO 2005/032484, WO 2005/048933, WO 2005/048945, WO 2005/051317, WO 2005/051324, WO 2005/066169, WO 2005/066170, WO 2005/066172, WO 2005/076783, WO 2005/079195, WO 2005/094531, WO 2005/123079, WO 2005/123080, WO 2006/009826, WO 2006/009832, WO 2006/026760, WO 2006/028451, WO 2006/028545, WO 2006/028962, WO 2006/029115, WO 2006/038923, WO 2006/065280, WO 2006/074003, WO 2006/083440, WO 2006/086449, WO 2006/091394, WO 2006/086633, WO 2006/086634, WO 2006/091567, WO 2006/091568, WO 2006/091647, WO 2006/093514, and WO 2006/098852. Additional examples of small molecule IRMs include certain purine derivatives (such as those described in U.S. Pat. Nos. 6,376,501, and 6,028,076), certain imidazoquinoline amide derivatives (such as those described in U.S. Pat. No. 6,069,149), certain imidazopyridine derivatives (such as those described in U.S. Pat. No. 6,518,265), certain benzimidazole derivatives (such as those described in U.S. Pat. No. 6,387,938), certain derivatives of a 4-aminopyrimidine fused to a five membered nitrogen containing heterocyclic ring (such as adenine derivatives described in U.S. Pat. Nos. 6,376,501; 6,028,076 and 6,329,381; and in WO 02/08905), and certain 3-β-D-ribofuranosylthiazolo[4,5-d]pyrimidine derivatives (such as those described in U.S. Publication No. 2003/0199461), and certain small molecule immuno-potentiator compounds such as those described, for example, in U.S. Patent Publication No. 2005/0136065.

Other TLR agonists include large biological molecules such as oligonucleotide sequences. Some TLR agonist oligonucleotide sequences contain cytosine-guanine dinucleotides (CpG) and are described, for example, in U.S. Pat. Nos. 6,194,388; 6,207,646; 6,239,116; 6,339,068; and 6,406,705. Some CpG-containing oligonucleotides can include synthetic immunomodulatory structural motifs such as those described, for example, in U.S. Pat. Nos. 6,426,334 and 6,476,000. Other TLR agonist nucleotide sequences lack CpG sequences and are described, for example, in International Patent Publication No. WO 00/75304. Still other TLR agonist nucleotide sequences include guanosine- and uridine-rich single-stranded RNA (ssRNA) such as those described, for example, in Heil et ah, Science, vol. 303, pp. 1526-1529, Mar. 5, 2004.

Other TLR agonists include biological molecules such as aminoalkyl glucosaminide phosphates (AGPs) and are described, for example, in U.S. Pat. Nos. 6,113,918; 6,303,347; 6,525,028; and 6,649,172.

Further TLR agonists useful in the present invention may include those described herein below.

TLR2/1 agonists and TLR2/6 agonists: TLR2 is typically a heteromeric receptor found in combination with either TLR1 or TLR6. Bacterial lipopeptides are the main agonists for TLR2-containing receptors. These agonists include: mycoplasmal macrophage-activating lipoprotein-2; tri-palmitoyl-cysteinyl-seryl-(lysyl)$_3$-lysine (P3CSK4), dipalmitoyl-CSK4 (P2-CSK4), and monopalmitoyl-CSK4 (PCSK4); the tripalmitoyl-S-glyceryl-cysteine (Pam(3)Cys)-modified lipoproteins, including OspA from the Lyme disease spirochete *Borrelia burgdorferi*; mycobacterial cell wall fractions enriched for lipoarrabinomannan, mycolylarabinogalactan-peptidoglycan complex, or *M. tuberculosis* total lipids.

TLR3 agonists: TLR3 agonists signal through the TRIF pathway to generate cytokines. The administration of viral genomes or partial genomes that generate dsRNA is another means of activating these pathways. In some cases, even endogenous messenger RNA (mRNA) can stimulate TLR3, and bacterial RNA can be especially stimulatory for dendritic cells. It has also been suggested that RNA stimulates dendritic cells through a nucleotide receptor. While viral double stranded RNAs (dsRNAs) can be used to stimulate TLR3, the best tested TLR3 agonist is polyriboinosinic-polyribocytidylic acid or Poly(I:C) which is a synthetic form of dsRNA. Poly(I:C) has antitumor effects in mice at a dose of 100 ug intraperitoneally or intravenously and has been extensively tested in humans with cancer. Poly(I:C) was shown to ameliorate herpes simplex keratoconjunctivitis in mice and to reduce the growth of *Leishmania* in mouse cells. For peptide vaccination, Poly(I:C) was used at a dose of 50 ug subcutaneously. In humans with herpes simplex infection and cancer, Poly(I:C) has been used at a dose of 3-12 mg/kg. Ampligen (poly I:poly C12U) is a mismatched form of dsRNA that has also been tested.

TLR4 agonists: TLR4 can signal cells through both the MyD88 and the TRIF pathways. Its special utility in activating human dendritic cells is art recognized. The classic agonist for TLR4 is bacterial lipopolysaccharide (LPS), which refers to a family of substances containing lipid A and its cogeners. An exemplary form of LPS is *E. coli* B:O111 (Sigma Chemicals). However, in an effort to make a less toxic form of TLR4 agonist, monophosphoryl lipid A (MPL) compounds have been produced and some are active in humans. The synthetic adjuvant, ASO2 (GlaxoSmithKline, United Kingdom), contains MPL as a component.

TLR5 agonists: The principal agonist for TLR5 is bacterial flagellin.

TLR7 agonists: For TLR7 agonists, these include, but are not limited to, single-stranded RNA; imidazoquinoline compounds such as resiquimod and imiquimod; Loxoribine (7-allyl-7,8-dihydro-8-oxo-guanosine) and related compounds; 7-Thia-8-oxoguanosine, 7-deazaguanosine, and related guanosine analogs; ANA975 (Anadys Pharmaceuticals) and related compounds; SM-360320 (Sumimoto); 3M-01 and 3M-03 (3M Pharmaceuticals); and adenosine analogs such as UC-1V150 (Jin et al., Bioorganic Medicinal Chem Lett (2006) 16:4559-4563, compound 4). It has been observed that TLR7 agonists directly activate plasmacytoid dendritic cells to make IFN-alpha, whereas TLR8 agonists directly activate myeloid dendritic cells, monocytes, and monocyte-derived dendritic cells to make proinflammatory cytokines and chemokines, such as TNF, IL-12, and MIP-1. Nevertheless, many compounds are agonists for both TLR7 and TLR8.

TLR8 agonists: As noted above, many of the compounds that activate TLR7 also activate TLR8. 3M-03 activates both TLR7 and TLR8, but 3M-02 is more specific for TLR8. Again, many compounds are agonists for both TLR7 and TLR8. Poly-G containing 10 guanosine nucleosides connected by phosphorothioate linkages (Poly-G10) is also a TLR8 agonist that may be especially useful as a substance that shuts off the immunosuppressive functions of regulator CD4+CD25+ T cells.

TLR9 agonists: Immunostimulatory oligonucleotides or polynucleotides such as CpG-containing oligodeoxynucleotides (CpG ODN) are the prototype agonists for TLR9. More generally, they are called immunostimulatory sequences of oligodeoxynucleotides (ISS-ODN) because many immunostimulatory oligonucleotides (ODNs) do not contain a CpG motif. Typically, the ODN is a synthetic thiophosphorylate-linked compound. However, many types of DNA and RNA can activate TLR9 including bacterial DNA, liposomal vertebrate DNA, insect DNA, *chlamydia* polynucleotides and others.

Another class of TLR9 agonists are nucleotide sequences containing a synthetic cytosine-phosphate-2'-deoxy-7-deazaguanosine dinucleotide (CpR), called immunomodulatory oligonucleotides (IMOs) (Hybridon, Inc.). A dumbbell-like covalently-closed structure is also art recognized (dSLIM-30L1) that is an agonist for TLR9. PolyG oligodeoxynucleotides can also be immunostimulatory. Even double-stranded DNA, such as that released from dying cells, can increase an immune response. Plasmid DNA may be especially immunostimulatory. While this may be due to CpG motifs, it is not clear if this is always due to its agonistic activity for TLR9.

TLR11 agonists: One agonist for TLR11 is the profilin-like molecule from the protozoan parasite *Toxoplasma gondii* (PFTG).

In embodiments contemplated herein, the TLR agonist used as described above can be selected from triacylated lipoproteins, lipoteichoic acid, peptidoglycans, zymosan, Pam3CSK4, diacylated lipopeptides, heat shock proteins, HMBG1, uric acid, fibronectin, ECM proteins, MALP2, RC-529, dsRNA, Poly I:C, *Mycobacterium bovis*, (*Bacillus*-Calmette Guérin, BCG), Poly A:U, LPS, MDFbeta-2, beta-defensin 2, fibronectin EDA, snapin, tenascin C, MPL, flagellin, ssRNA, CpG-A, Poly G10, Poly G3, imiquimod 852A (Aldera), unmethylated CpG DNA, PamCysPamSK4, *Toxoplasma gondii* profiling, Loxoribine, or VSV. In specific embodiments, the TLR agonist is monophosphoryl lipid A (MPL), *Mycobacterium bovis* (*Bacillus*-Calmette Guérin, BCG), CpG, ISCOMatrix, imiquimod (Aldera), Poly IC:LC, OK-432, and/or resiquimod.

2. Pharmaceutical formulations.

The active compounds described above may be formulated for administration in a pharmaceutical carrier in accordance with known techniques. See, e.g., Remington, *The Science And Practice of Pharmacy* (latest edition). In the manufacture of a pharmaceutical formulation according to the invention, the active compound (including the physiologically acceptable salts thereof) is typically admixed with, inter alia, an acceptable carrier. The carrier must, of course, be acceptable in the sense of being compatible with any other ingredients in the formulation and must not be deleterious to the patient. The carrier may be a solid or a liquid, or both, and is preferably formulated with the compound as a unit-dose formulation, for example, a tablet, which may contain from 0.01 or 0.5% to 95% or 99% by weight of the active compound. One or more active compounds may be incorporated in the formulations of the invention, which may be prepared by any of the well known techniques of pharmacy comprising admixing the components, optionally including one or more accessory ingredients.

The formulations of the invention include those suitable for oral, rectal, topical, buccal (e.g., sub-lingual), vaginal, parenteral (e.g., subcutaneous, intramuscular, intradermal, or intravenous), topical (i.e., both skin and mucosal surfaces, including airway surfaces), transdermal administration, and intraventricular injection (injection into a ventricle of the brain, e.g., by an implanted catheter or omman reservoir, such as in the case of morbid obesity) and although the most suitable route in any given case will depend on the nature and severity of the condition being treated and on the nature of the particular active compound which is being used.

Formulations suitable for oral administration may be presented in discrete units, such as capsules, cachets, lozenges, or tablets, each containing a predetermined amount of the active compound; as a powder or granules; as a solution or a suspension in an aqueous or non-aqueous liquid; or as an oil-in-water or water-in-oil emulsion. Such formulations may be prepared by any suitable method of pharmacy which includes the step of bringing into association the active compound and a suitable carrier (which may contain one or more accessory ingredients as noted above). In general, the formulations of the invention are prepared by uniformly and intimately admixing the active compound with a liquid or finely divided solid carrier, or both, and then, if necessary, shaping the resulting mixture. For example, a tablet may be prepared by compressing or molding a powder or granules containing the active compound, optionally with one or more accessory ingredients. Compressed tablets may be prepared by compressing, in a suitable machine, the compound in a free-flowing form, such as a powder or granules optionally mixed with a binder, lubricant, inert diluent, and/or surface active/dispersing agent(s). Molded tablets may be made by molding, in a suitable machine, the powdered compound moistened with an inert liquid binder.

Formulations suitable for buccal (sub-lingual) administration include lozenges comprising the active compound in a flavoured base, usually sucrose and acacia or tragacanth; and pastilles comprising the compound in an inert base such as gelatin and glycerin or sucrose and acacia.

Formulations of the present invention suitable for parenteral administration comprise sterile aqueous and non-aqueous injection solutions of the active compound, which preparations are preferably isotonic with the blood of the intended recipient. These preparations may contain antioxidants, buffers, bacteriostats and solutes which render the formulation isotonic with the blood of the intended recipient. Aqueous and non-aqueous sterile suspensions may include suspending agents and thickening agents. The formulations may be presented in unit\dose or multi-dose containers, for example sealed ampoules and vials, and may be stored in a freeze-dried (lyophilized) condition requiring only the addition of the sterile liquid carrier, for example, saline or water-for-injection immediately prior to use. Extemporaneous injection solutions and suspensions may be prepared from sterile powders, granules and tablets of the kind previously described. For example, in one aspect of the present invention, there is provided an injectable, stable, sterile composition comprising a compound of Formula (I), or a salt thereof, in a unit dosage form in a sealed container. The compound or salt is provided in the form of a lyophilizate which is capable of being reconstituted with a suitable pharmaceutically acceptable carrier to form a liquid composition suitable for injection thereof into a subject. The unit dosage form typically comprises from about 10 mg to about 10 grams of the compound or salt. When the compound or salt is substantially water-insoluble, a sufficient amount of emulsifying agent which is physiologically acceptable may be employed in sufficient quantity to emulsify the compound or salt in an aqueous carrier. One such useful emulsifying agent is phosphatidyl choline.

Formulations suitable for rectal administration are preferably presented as unit dose suppositories. These may be prepared by admixing the active compound with one or more conventional solid carriers, for example, cocoa butter, and then shaping the resulting mixture.

Formulations suitable for topical application to the skin preferably take the form of an ointment, cream, lotion, paste, gel, spray, aerosol, or oil. Carriers which may be used include petroleum jelly, lanoline, polyethylene glycols, alcohols, transdermal enhancers, and combinations of two or more thereof.

Formulations suitable for transdermal administration may be presented as discrete patches adapted to remain in intimate contact with the epidermis of the recipient for a prolonged period of time. Formulations suitable for transdermal administration may also be delivered by iontophoresis (see, for example, Pharmaceutical Research 3 (6):318 (1986)) and typically take the form of an optionally buffered aqueous solution of the active compound. Suitable formulations comprise citrate or bis\tris buffer (pH 6) or ethanol/water and contain from 0.1 to 0.2M active ingredient.

Further, the present invention provides liposomal formulations of the compounds disclosed herein and salts thereof. The technology for forming liposomal suspensions is well known in the art. When the compound or salt thereof is an aqueous-soluble salt, using conventional liposome technology, the same may be incorporated into lipid vesicles. In such an instance, due to the water solubility of the compound or salt, the compound or salt will be substantially entrained within the hydrophilic center or core of the liposomes. The lipid layer employed may be of any conventional composition and may either contain cholesterol or may be cholesterol-free. When the compound or salt of interest is water-insoluble, again employing conventional liposome formation technology, the salt may be substantially entrained within the hydrophobic lipid bilayer which forms the structure of the liposome. In either instance, the liposomes which are produced may be reduced in size, as through the use of standard sonication and homogenization techniques.

Of course, the liposomal formulations containing the compounds disclosed herein or salts thereof, may be lyophilized to produce a lyophilizate which may be reconstituted with a pharmaceutically acceptable carrier, such as water, to regenerate a liposomal suspension.

Other pharmaceutical compositions may be prepared from the water-insoluble compounds disclosed herein, or salts thereof, such as aqueous base emulsions. In such an instance, the composition will contain a sufficient amount of pharmaceutically acceptable emulsifying agent to emulsify the desired amount of the compound or salt thereof. Particularly useful emulsifying agents include phosphatidyl cholines, and lecithin.

In addition to compounds of formula (I) or their salts, the pharmaceutical compositions may contain other additives, such as pH-adjusting additives. In particular, useful pH-adjusting agents include acids, such as hydrochloric acid, bases or buffers, such as sodium lactate, sodium acetate, sodium phosphate, sodium citrate, sodium borate, or sodium gluconate. Further, the compositions may contain microbial preservatives. Useful microbial preservatives include methylparaben, propylparaben, and benzyl alcohol. The microbial preservative is typically employed when the formulation is placed in a vial designed for multidose use. Of course, as indicated, the pharmaceutical compositions of the present invention may be lyophilized using techniques well known in the art.

In one aspect, the invention provides a pharmaceutical composition comprising a pharmaceutically effective amount of a pan-TAM and/or MerTK/AXL inhibitor in combination with an immune checkpoint inhibitor as described herein and a pharmaceutically acceptable carrier. In another embodiment, the pan-TAM and/or MerTK/AXL inhibitor is administered orally and the checkpoint inhibitor is administered via intravenous, intramuscular, subcutaneous, or other route known and suitable for a quickly degradable protein.

The pan-TAM and/or MerTK/AXL inhibitor and immune complex inhibitor provided herein are administered in physical or temporal combination for medical therapy in a therapeutically effective amount. The amount of the compounds administered will typically be determined by a physician, in the light of the relevant circumstances, including the condition to be treated, the chosen route of administration, the compound administered, the age, weight, and response of the individual patient, the severity of the patient's symptoms, and the like.

In one aspect of the present invention as described above, the pan-TAM and/or MerTK/AXL inhibitor can be administered in combination with an immune checkpoint inhibitor, wherein the pan-TAM and/or MerTK/AXL inhibitor dose and/or the immune checkpoint inhibitor dose is a subtherapeutic dose for the disorder being treated.

The pan-TAM and/or MerTK/AXL inhibitor and/or immune checkpoint inhibitor can be administered by any suitable route associated with the particular compound, for example, the compounds may be administered by orally, rectally, buccally (e.g., sub-lingual), vaginally, parenterally (e.g., subcutaneous, intramuscular, intradermal, or intravenous), topically (i.e., both skin and mucosal surfaces, including airway surfaces), transdermally, intraventricular injection (injection into a ventricle of the brain, e.g., by an implanted catheter or Ommaya reservoir, such as in the case of morbid obesity), ocularly (via injection, implantation or by reservoir), and intranasally, although the most suitable route in any given case will depend on the nature and severity of the condition being treated and on the nature of the particular active compound which is being used.

3. Dosage and Routes of Administration.

As noted above, the present invention provides pharmaceutical formulations comprising the active compounds (including the pharmaceutically acceptable salts thereof), in pharmaceutically acceptable carriers for oral, nasal, rectal, topical, buccal, parenteral, intramuscular, intradermal, or intravenous, and transdermal administration.

The therapeutically effective dosage of any specific compound, the use of which is in the scope of present invention, will vary somewhat from compound to compound, and patient to patient, and will depend upon the condition of the patient and the route of delivery. As a general proposition, a dosage from about 0.1 to about 50 mg/kg will have therapeutic efficacy, with all weights being calculated based upon the weight of the active compound, including the cases where a salt is employed. Toxicity concerns at the higher level may restrict intravenous dosages to a lower level such as up to about 10 mg/kg, with all weights being calculated based upon the weight of the active base, including the cases where a salt is employed. A dosage from about 10 mg/kg to about 50 mg/kg may be employed for oral administration. In some embodiments, a dosage from about 0.5 mg/kg to 5 mg/kg may be employed for intramuscular injection. In some embodiments, dosages are 1 µmol/kg to 50 µmol/kg, and more preferably 22 µmol/kg and 33 µmol/kg of the compound for intravenous or oral administration. The duration of the treatment can be once per day for a period of two to three weeks or until the condition is essentially controlled.

The therapeutically effective dosage of any active compound described herein will be determined by the health care practitioner depending on the condition, size and age of the patient as well as the route of delivery. In one non-limited embodiment, a dosage from about 0.1 to about 200 mg/kg of the pan-TAM and/or MerTK/AXL inhibitor and immune checkpoint inhibitor, independently, is herein contemplated, with all weights being calculated based upon the weight of the active compound, including the cases where a salt is employed. In some embodiments, the dosage can be the amount of compound needed to provide a serum concentration of the pan-TAM and/or MerTK/AXL inhibitor and immune checkpoint inhibitor of up to between about 1 and 5, 10, 20, 30, or 40 µM.

In one aspect of the invention, a method is provided to treat a host suffering from a cancer by administering a daily amount of a pan-TAM and/or MerTK/AXL inhibitor in combination with an immune checkpoint inhibitor, wherein the pan-TAM and/or MerTK/AXL inhibitor is administered in a dose between about 0.5 mg and about 200 mg per administration, which may be at least 1, 2, 3, 4, or 5 times a day or perhaps only periodically on certain days, as instructed by the attending physician. In one embodiment, the pan-TAM and/or MerTK/AXL inhibitor dose is at least about 1 mg, about 2 mg, about 3 mg, about 4 mg, about 5 mg, about 10 mg, about 12 mg, about 15 mg, about 20 mg, about 25 mg, about 30 mg, about 35 mg, about 40 mg, about 45 mg, about 50 mg, about 55 mg, about 60 mg, about 65 mg, about 70 mg, about 75 mg, about 80 mg, about 85 mg, about 90 mg, about 95 mg, about 100 mg, about 110 mg, about 125 mg, about 140 mg, about 150, about 175, or about 200 mg. In another embodiment, the pan-TAM and/or MerTK/AXL inhibitor dose is between about 200 mg and 1250 mg. In one embodiment, the MerTK inhibitor dose is about 200 mg, about 225 mg, about 250 mg, about 275 mg, about 300 mg, about 325 mg, about 350 mg, about 375 mg, about 400 mg, about 425 mg, about 450 mg, about 475 mg, about 500 mg, about 525 mg, about 550 mg, about 575 mg, about 600 mg, about 625 mg, about 650 mg, about 675 mg, about 700 mg, about 725 mg, about 750 mg, about 775 mg, about 800 mg, about 825 mg, about 850 mg, about 875 mg, about 900 mg, about 925 mg, about 950 mg, about 975 mg, about 1000 mg or more.

In one embodiment, a compound of Formula I, II, III, IV, V, VI, or VII is combined for therapy temporally or physically with an additional anti-tumor agent, anti-neoplastic agent, anti-cancer agent, immunomodulatory agent, or immunostimulatory agent in addition to the use of the immune checkpoint inhibitor. The dosage administered to the host can be similar to that as administered during monotherapy treatment, or may be lower, for example, between about 0.5 mg and about 150 mg. In one embodiment, the dose is at least about 1 mg, about 2 mg, about 3 mg, about 4 mg, about 5 mg, about 10 mg, about 12 mg, about 15 mg, about 20 mg, about 25 mg, about 30 mg, about 35 mg, about 40 mg, about 45 mg, about 50 mg, about 55 mg, about 60 mg, about 65 mg, about 70 mg, about 75 mg, about 80 mg, about 85 mg, about 90 mg, about 95 mg, about 100 mg, about 110 mg, about 125 mg, about 140 mg, or about 150 mg.

In one embodiment, the invention provides a pharmaceutically acceptable composition for use as a chemotherapeutic comprising a compound of Formula I, II, III, IV, V, VI, VII, or VIII, or a salt, isotopic analog, prodrug, or a combination thereof, and an immune checkpoint inhibitor. In another embodiment, a compound of Formula I, II, III, IV, V, VI, or VII is administered orally and is provided in combination with an immune checkpoint inhibitor administered intravenously. In one embodiment, the immune checkpoint inhibitor, for example an anti-PD1, anti-PD-L1, or anti-CTLA4 antibody, can be administered in a first pharmaceutical composition as an intravenous infusion, and a second pharmaceutical composition comprising one or more therapeutic agents, including a compound of Formula I, II, III, IV, V, VI, VII, or VIII, can be administered concurrently, prior to, or following administration of an immune checkpoint inhibitor, wherein the second pharmaceutical composition can be administered orally, intravenously, or subcutaneously.

The person of ordinary skill will realize that methods of determining effective dosages of the selected immune checkpoint inhibitor, such as an antibody, to administer to a patient in need thereof, either alone or in combination with one or more other agents, may be determined by standard dose-response and toxicity studies that are well known in the art. In one embodiment, an immune checkpoint inhibitor such as an antibody may be administered at about 0.3-10 mg/kg, or the maximum tolerated dose, administered periodically, according to the judgement of the physician. Non-limiting examples of dosage regimens include up to about every week, about every two weeks, three weeks, every six weeks, or about every three months. Alternatively, the immune checkpoint inhibitor antibody may be administered by an escalating dosage regimen including administering a first dosage at about 3 mg/kg, a second dosage at up to about 5 mg/kg, and a third dosage at about 9 mg/kg. Alternatively, the escalating dosage regimen includes administering a first dosage of immune checkpoint inhibitor antibody at up to about 5 mg/kg and a second dosage at up to about 9 mg/kg. Another stepwise escalating dosage regimen may include administering a first dosage of immune checkpoint inhibitor antibody up to about 3 mg/kg, a second dosage of up to about 3 mg/kg, a third dosage of up to about 5 mg/kg, a fourth dosage of up to about 5 mg/kg, and a fifth dosage of up to about 9 mg/kg. In another aspect, a stepwise escalating dosage regimen may include administering a first dosage of up to 5 mg/kg, a second dosage of up to 5 mg/kg, and a third dosage of up to 9 mg/kg.

Non-limiting examples of suitable dosages of an immune checkpoint inhibitor antibody include 3 mg/kg ipilimumab administered intravenously over 90 minutes every three weeks for four doses; 10 mg/kg ipilimumab every three weeks for eight cycles; 10 ipilimumab mg/kg every three weeks for four cycles then every 12 weeks for a total of three years; 2 mg/kg pembrolizumab administered intravenously over 30 minutes every three weeks; 10 mg/kg pembrolizumab every two or every three weeks; 15 mg/kg tremilimumab every three months; between 6-15 mg/kg tremilimumab every three months; 3 mg/kg nivolumab administered intravenously over 60 minutes every two weeks; between 0.3-10 mg/kg nivolumab every two weeks; 0.1, 0.3, 1, 3 or 10 mg/kg nivolumab every two weeks for up to 96 weeks.

Active compounds may be administered as pharmaceutically acceptable prodrugs, which are those prodrugs of the active compounds of the present invention which are, within the scope of sound medical judgment, suitable for use in contact with the tissues of humans and lower animals without undue toxicity, irritation, allergic response and the like, commensurate with a reasonable risk/benefit ratio, and effective for their intended use, as well as the zwitterionic forms, where possible, of the compounds of the invention. The term "prodrug" refers to compounds that are rapidly transformed in vivo to yield the parent compound of the above formulae, for example, by hydrolysis in blood. A thorough discussion is provided in T. Higuchi and V. Stella, Prodrugs as Novel delivery Systems, Vol. 14 of the A.C.S. Symposium Series and in Edward B. Roche, ed., Bioreversible Carriers in Drug Design, American Pharmaceutical Association and Pergamon Press, 1987, both of which are incorporated by reference herein. See also U.S. Pat. No. 6,680,299 Examples include a prodrug that is metabolized in vivo by a subject to an active drug having an activity of active compounds as described herein, wherein the prodrug is an ester of an alcohol or carboxylic acid group, if such a group is present in the compound; an acetal or ketal of an alcohol group, if such a group is present in the compound; an N-Mannich base or an imine of an amine group, if such a group is present in the compound; or a Schiff base, oxime, acetal, enol ester, oxazolidine, or thiazolidine of a carbonyl group, if such a group is present in the compound, such as described in U.S. Pat. Nos. 6,680,324 and 6,680,322.

4. Methods of Use.

The active compounds and methods described herein are useful for the treatment of tumors and cancers. As contemplated herein, the cancer treated can be a primary tumor or a metastatic tumor. In one aspect, the methods described herein are used to treat a solid tumor, for example, melanoma, lung cancer (including lung adenocarcinoma, basal cell carcinoma, squamous cell carcinoma, large cell carcinoma, bronchioloalveolar carcinoma, bronchiogenic carcinoma, non-small-cell carcinoma, small cell carcinoma, mesothelioma); breast cancer (including ductal carcinoma, lobular carcinoma, inflammatory breast cancer, clear cell carcinoma, mucinous carcinoma, serosal cavities breast carcinoma); colorectal cancer (colon cancer, rectal cancer, colorectal adenocarcinoma); anal cancer; pancreatic cancer (including pancreatic adenocarcinoma, islet cell carcinoma, neuroendocrine tumors); prostate cancer; prostate adenocarcinoma; ovarian carcinoma (ovarian epithelial carcinoma or surface epithelial-stromal tumor including serous tumor, endometrioid tumor and mucinous cystadenocarcinoma, sex-cord-stromal tumor); liver and bile duct carcinoma (including hepatocellular carcinoma, cholangiocarcinoma, hemangioma); esophageal carcinoma (including esophageal adenocarcinoma and squamous cell carcinoma); oral and oropharyngeal squamous cell carcinoma; salivary gland adenoid cystic carcinoma; bladder cancer; bladder carcinoma; carcinoma of the uterus (including endometrial adenocarcinoma, ocular, uterine papillary serous carcinoma, uterine clear-cell carcinoma, uterine sarcomas and leiomyosarcomas, mixed mullerian tumors); glioma, glioblastoma, medullablastoma, and other tumors of the brain; kidney cancers (including renal cell carcinoma, clear cell carcinoma, Wilm's tumor); cancer of the head and neck (including squamous cell carcinomas); cancer of the stomach (gastric cancers, stomach adenocarcinoma, gastrointestinal stromal tumor); testicular cancer; germ cell tumor; neuroendocrine tumor; cervical cancer; carcinoids of the gastrointestinal tract, breast, and other organs; signet ring cell carcinoma; mesenchymal tumors including sarcomas, fibrosarcomas, haemangioma, angiomatosis, haemangiopericytoma, pseudoangiomatous stromal hyperplasia, myofibroblastoma, fibromatosis, inflammatory myofibroblastic tumor, lipoma, angiolipoma, granular cell tumor, neurofibroma, schwannoma, angiosarcoma, liposarcoma, rhabdomyosarcoma, osteosarcoma, leiomyoma, leiomysarcoma, skin, including melanoma, cervical, retinoblastoma, head and neck cancer, pancreatic, brain, thyroid, testicular, renal, bladder, soft tissue, adenal gland, urethra, cancers of the penis, myxosarcoma, chondrosarcoma, osteosarcoma, chordoma, malignant fibrous histiocytoma, lymphangiosarcoma, mesothelioma, squamous cell carcinoma; epidermoid carcinoma, malignant skin adnexal tumors, adenocarcinoma, hepatoma, hepatocellular carcinoma, renal cell carcinoma, hypernephroma, cholangiocarcinoma, transitional cell carcinoma, choriocarcinoma, seminoma, embryonal cell carcinoma, glioma anaplastic; glioblastoma multiforme, neuroblastoma, medulloblastoma, malignant meningioma, malignant schwannoma, neurofibrosarcoma, parathyroid carcinoma, medullary carcinoma of thyroid, bronchial carcinoid, pheochromocytoma, Islet cell carcinoma, malignant carcinoid, malignant paraganglioma, melanoma, Merkel cell neoplasm, cystosarcoma phylloide, salivary cancers, thymic carcinomas, and cancers of the vagina among others.

Chemotherapeutic Agents.

In one embodiment, an active compound as described herein is used in combination or alternation with a chemotherapeutic agent. Such agents may include, but are not limited to, tamoxifen, midazolam, letrozole, bortezomib, anastrozole, goserelin, an mTOR inhibitor, a PI3 kinase inhibitors, dual mTOR-PI3K inhibitors, MEK inhibitors, RAS inhibitors, ALK inhibitors, HSP inhibitors (for example, HSP70 and HSP 90 inhibitors, or a combination thereof). Examples of mTOR inhibitors include but are not limited to rapamycin and its analogs, everolimus (Afinitor), temsirolimus, ridaforolimus, sirolimus, and deforolimus. Examples of PI3 kinase inhibitors include but are not limited to Wortmannin, demethoxyviridin, perifosine, idelalisib, PX-866, IPI-145, BAY 80-6946, BEZ235, RP6503, TGR 1202 (RP5264), MLN1117 (INK1117), Pictilisib, Buparlisib, SAR245408 (XL147), SAR245409 (XL765), Palomid 529, ZSTK474, PWT33597, RP6530, CUDC-907, and AEZS-136. Examples of MEK inhibitors include but are not limited to Tametinib, Selumetinib, MEK162, GDC-0973 (XL518), and PD0325901. Examples of RAS inhibitors include but are not limited to Reolysin and siG12D LODER. Examples of ALK inhibitors include but are not limited to Crizotinib, AP26113, and LDK378. HSP inhibitors include but are not limited to Geldanamycin or 17-N-Allylamino-17-demethoxygeldanamycin (17AAG), and Radicicol. In one embodiment, the chemotherapeutic agent is an anti-programmed cell death-1 (PD-1) agent, for example, nivolumab, pembrolizumab, BMS936559, lambrolizumab, MPDL3280A, pidilizumab, AMP-244, and MEDI4736. In one embodiment, the chemotherapeutic agent is a B-RAF inhibitor, for example, vemurafenib or sorafenib. In one embodiment, the chemotherapeutic agent is a FGFR inhibitor, for example, but not limited to, AZD4547, dovitinib, BGJ398, LY2874455, and ponatinib. In one embodiment, an active compound as described herein is used in combination with crizotinib.

Suitable chemotherapeutic agents further include, but are not limited to, radioactive molecules, toxins, also referred to as cytotoxins or cytotoxic agents, which includes any agent that is detrimental to the viability of cells, agents, and liposomes or other vesicles containing chemotherapeutic compounds. General anticancer pharmaceutical agents include: Vincristine (Oncovin®) or liposomal vincristine (Marqibo®), Daunorubicin (daunomycin or Cerubidine®) or doxorubicin (Adriamycin®), Cytarabine (cytosine arabinoside, ara-C, or Cytosar®), L-asparaginase (Elspar®) or PEG-L-asparaginase (pegaspargase or Oncaspar®), Etoposide (VP-16), Teniposide (Vumon®), 6-mercaptopurine (6-MP or Purinethol®), Methotrexate, Cyclophosphamide (Cytoxan®), Prednisone, Dexamethasone (Decadron), imatinib (Gleevec®), dasatinib (Sprycel®), nilotinib (Tasigna®), bosutinib (Bosulif®), and ponatinib (Iclusig™). Examples of additional suitable chemotherapeutic agents include but are not limited to 1-dehydrotestosterone, 5-fluorouracil decarbazine, 6-mercaptopurine, 6-thioguanine, actinomycin D, adriamycin, aldesleukin, alkylating agents, allopurinol sodium, altretamine, amifostine, anastrozole, anthramycin (AMC)), anti-mitotic agents, cis-dichlorodiamine platinum (II) (DDP) cisplatin), diamino dichloro platinum, anthracyclines, antibiotics, antimetabolites, asparaginase, BCG live (intravesical), betamethasone sodium phosphate and betamethasone acetate, bicalutamide, bleomycin sulfate, busulfan, calcium leucouorin, calicheamicin, capecitabine, carboplatin, lomustine (CCNU), carmustine (BSNU), Chlorambucil, Cisplatin, Cladribine, Colchicin, conjugated estrogens, Cyclophosphamide, Cyclothosphamide, Cytarabine, Cytarabine, cytochalasin B, Cytoxan, Dacarbazine, Dactinomycin, dactinomycin (formerly actinomycin), daunirubicin HCL, daunorucbicin citrate, denileukin diftitox, Dexrazoxane, Dibromomannitol, dihydroxy anthracin dione, Docetaxel, dolasetron mesylate, doxorubicin HCL, dronabinol, E. coli L-asparaginase, emetine, epoetin-α, Erwinia L-asparaginase, esterified estrogens, estradiol, estramustine phosphate sodium, ethidium bromide, ethinyl estradiol, etidronate, etoposide citrororum factor, etoposide phosphate, filgrastim, floxuridine, fluconazole, fludarabine phosphate, fluorouracil, flutamide, folinic acid, gemcitabine HCL, glucocorticoids, goserelin acetate, gramicidin D, granisetron HCL, hydroxyurea, idarubicin HCL, ifosfamide, interferon α-2b, irinotecan HCL, letrozole, leucovorin calcium, leuprolide acetate, levamisole HCL, lidocaine, lomustine, maytansinoid, mechlorethamine HCL, medroxyprogesterone acetate, megestrol acetate, melphalan HCL, mercaptipurine, mesna, methotrexate, methyltestosterone, mithramycin, mitomycin C, mitotane, mitoxantrone, nilutamide, octreotide acetate, oligomycin A, ondansetron HCL, paclitaxel, pamidronate disodium, pentostatin, pilocarpine HCL, plimycin, polifeprosan 20 with carmustine implant, porfimer sodium, procaine, procarbazine HCL, propranolol, rituximab, sargramostim, streptozotocin, tamoxifen, taxol, teniposide, tenoposide, testolactone, tetracaine, thioepa chlorambucil, thioguanine, thiotepa, topotecan HCL, toremifene citrate, trastuzumab, tretinoin, valrubicin, vinblastine sulfate, vincristine sulfate, and vinorelbine tartrate.

Ionizing Radiation

Ionizing radiation (IR) is an important therapeutic modality to treat a range of cancers and other proliferative disorders such as tumors. Radiation therapy uses high energy radiation to shrink tumors and kill the proliferating cells. X-rays, gamma rays, and charged particles are typical kinds of ionizing radiation used for cancer treatments. IR causes extensive DNA damage to abnormally proliferating cells such as cancer and tumor cells.

As contemplated herein, the pan-TAM kinase and MerTK/AXL inhibitors and immune checkpoint inhibitor can be further combined or alternated with ionizing radiation treatments directed at a particular cancer. For example, the combinations contemplated herein can be combined or alternated with standard of care radiation treatments based on the particular cancer a host may be suffering from. Certain standard of care radiation modalities may include those wherein the subject is exposed to IR at least 5 times a week, at least 4 times a week, at least 3 times a week, at least 2 times a week, at least 1 time a week, at least 3 times a month, at least 2 times a month, or at least 1 time a month.

The methods contemplated herein are also useful for treating a host suffering from a tumor or cancer wherein the administration of the combination results in an additive proliferation inhibitory, growth inhibitory, or growth delayed effect in the cancer compared to the use of either the pan-TAM kinase or MerTK/AXL inhibitors alone or the immune checkpoint inhibitor alone. In some embodiments, the cancer treated may be a cancer that otherwise is not responsive to immune downregulation inhibitor monotherapy, that is, a cancer wherein its growth or proliferation is not significantly, substantially, or markedly inhibited or delayed by the administration of an immune checkpoint inhibitor alone.

The methods described herein can also be used for treating a host suffering from a lymphoma or lymphocytic or myelocytic proliferation disorder or abnormality. For example, the cancer can be a Hodgkin Lymphoma of a Non-Hodgkin Lymphoma. For example, the subject can be suffering from a Non-Hodgkin Lymphoma such as, but not limited to: an AIDS-Related Lymphoma; Anaplastic Large-Cell Lymphoma; Angioimmunoblastic Lymphoma; Blastic NK-Cell Lymphoma; Burkitt's Lymphoma; Burkitt-like Lymphoma (Small Non-Cleaved Cell Lymphoma); Chronic Lymphocytic Leukemia/Small Lymphocytic Lymphoma; Cutaneous T-Cell Lymphoma; Diffuse Large B-Cell Lymphoma; Enteropathy-Type T-Cell Lymphoma; Follicular Lymphoma; Hepatosplenic Gamma-Delta T-Cell Lymphoma; Lymphoblastic Lymphoma; Mantle Cell Lymphoma; Marginal Zone Lymphoma; Nasal T-Cell Lymphoma; Pediatric Lymphoma; Peripheral T-Cell Lymphomas; Primary Central Nervous System Lymphoma; T-Cell Leukemias; Transformed Lymphomas; Treatment-Related T-Cell Lymphomas; or Waldenstrom's Macroglobulinemia.

Alternatively, the subject may be suffering from a Hodgkin Lymphoma, such as, but not limited to: Nodular Sclerosis Classical Hodgkin's Lymphoma (CHL); Mixed Cellularity CHL; Lymphocyte-depletion CHL; Lymphocyte-rich CHL; Lymphocyte Predominant Hodgkin Lymphoma; or Nodular Lymphocyte Predominant HL.

In one embodiment, the methods as described herein may be useful to treat a host suffering from a specific T-cell, a B-cell, or a NK-cell based lymphoma, proliferative disorder, or abnormality. For example, the subject can be suffering from a specific T-cell or NK-cell lymphoma, for example, but not limited to: Peripheral T-cell lymphoma, for example, peripheral T-cell lymphoma and peripheral T-cell lymphoma not otherwise specified (PTCL-NOS); anaplastic large cell lymphoma, for example anaplastic lymphoma kinase (ALK) positive, ALK negative anaplastic large cell lymphoma, or primary cutaneous anaplastic large cell lymphoma; angioimmunoblastic lymphoma; cutaneous T-cell lymphoma, for example mycosis fungoides, Sézary syndrome, primary cutaneous anaplastic large cell lymphoma, primary cutaneous CD30+ T-cell lymphoproliferative disorder; primary cutaneous aggressive epidermotropic CD8+ cytotoxic T-cell lymphoma; primary cutaneous gamma-delta T-cell lymphoma; primary cutaneous small/medium CD4+ T-cell lymphoma, and lymphomatoid papulosis; Adult T-cell Leukemia/Lymphoma (ATLL); Blastic NK-cell Lymphoma; Enteropathy-type T-cell lymphoma; Hematosplenic gamma-delta T-cell Lymphoma; Lymphoblastic Lymphoma; Nasal NK/T-cell Lymphomas; Treatment-related T-cell lymphomas; for example lymphomas that appear after solid organ or bone marrow transplantation; T-cell prolymphocytic leukemia; T-cell large granular lymphocytic leukemia; Chronic lymphoproliferative disorder of NK-cells; Aggressive NK cell leukemia; Systemic EBV+ T-cell lymphoproliferative disease of childhood (associated with chronic active EBV infection); Hydroa vacciniforme-like lymphoma; Adult T-cell leukemia/lymphoma; Enteropathy-associated T-cell lymphoma; Hepatosplenic T-cell lymphoma; or Subcutaneous panniculitis-like T-cell lymphoma.

Alternatively, the subject may be suffering from a specific B-cell lymphoma or proliferative disorder such as, but not limited to: multiple myeloma; Diffuse large B cell lymphoma; Follicular lymphoma; Mucosa-Associated Lymphatic Tissue lymphoma (MALT); Small cell lymphocytic lymphoma; Mantle cell lymphoma (MCL); Burkitt lymphoma; Mediastinal large B cell lymphoma; Waldenstrom macroglobulinemia; Nodal marginal zone B cell lymphoma (NMZL); Splenic marginal zone lymphoma (SMZL); Intravascular large B-cell lymphoma; Primary effusion lymphoma; or Lymphomatoid granulomatosis; Chronic lymphocytic leukemia/small lymphocytic lymphoma; B-cell prolymphocytic leukemia; Hairy cell leukemia; Splenic lymphoma/leukemia, unclassifiable; Splenic diffuse red pulp small B-cell lymphoma; Hairy cell leukemia-variant; Lymphoplasmacytic lymphoma; Heavy chain diseases, for example, Alpha heavy chain disease, Gamma heavy chain disease, Mu heavy chain disease; Plasma cell myeloma; Solitary plasmacytoma of bone; Extraosseous plasmacytoma; Primary cutaneous follicle center lymphoma; T cell/histiocyte rich large B-cell lymphoma; DLBCL associated with chronic inflammation; Epstein-Barr virus (EBV)+ DLBCL of the elderly; Primary mediastinal (thymic) large B-cell lymphoma; Primary cutaneous DLBCL, leg type; ALK+ large B-cell lymphoma; Plasmablastic lymphoma; Large B-cell lymphoma arising in HHV8-associated multicentric; Castleman disease; B-cell lymphoma, unclassifiable, with features intermediate between diffuse large B-cell lymphoma and Burkitt lymphoma; B-cell lymphoma, unclassifiable, with features intermediate between diffuse large B-cell lymphoma and classical Hodgkin lymphoma; Nodular sclerosis classical Hodgkin lymphoma; Lymphocyte-rich classical Hodgkin lymphoma; Mixed cellularity classical Hodgkin lymphoma; or Lymphocyte-depleted classical Hodgkin lymphoma.

The methods described herein can be used to treat a subject suffering from a leukemia. For example, the subject may be suffering from an acute or chronic leukemia of a lymphocytic or myelogenous origin, such as, but not limited to: Acute lymphoblastic leukemia (ALL); Acute myelogenous leukemia (AML); Chronic lymphocytic leukemia (CLL); Chronic myelogenous leukemia (CML); juvenile myelomonocytic leukemia (JMML); hairy cell leukemia (HCL); acute promyelocytic leukemia (a subtype of AML); T-cell prolymphocytic leukemia (TPLL); large granular lymphocytic leukemia; or Adult T-cell chronic leukemia; large granular lymphocytic leukemia (LGL). In one embodiment, the patient suffers from an acute myelogenous leukemia, for example an undifferentiated AML (M0); myeloblastic leukemia (M1; with/without minimal cell maturation); myeloblastic leukemia (M2; with cell maturation); promyelocytic leukemia (M3 or M3 variant [M3V]); myelomonocytic leukemia (M4 or M4 variant with eosinophilia [M4E]); monocytic leukemia (M5); erythroleukemia (M6); or megakaryoblastic leukemia (M7).

In one embodiment, the methods described herein can be used to treat a host suffering from Acute Myeloid Leukemia (AML). In one embodiment, the AML contains a wild type FLT3 protein. In one embodiment, the replication of the AML cells are dependent on FLT3 expression for proliferation. In one embodiment, the AML contains a FLT3-ITD mutation. In one embodiment, the AML contains a FLT3-TKD mutation. In one embodiment, the AML contains both a FLT3-ITD and FLT3-TKD mutation.

FLT3-ITD mutations are well known in the art. FLT3-TKD mutations are also well known in the art. In one embodiment, a MerTK inhibitor in combination with an immune checkpoint inhibitor is administered to a host suffering from AML, wherein the AML contains a mutation within the FLT3-TKD at amino acid F691 or D835. In one embodiment, the FLT3-TKD mutation is selected from D835H, D835N, D835Y, D835A, D835V, D835V, D835E, I836F, I836L, I836V, I836D, I836H, I836M, and F691L. In one embodiment, the host is suffering from the FLT3-TKD mutation D835Y. In one embodiment, the host is suffering from the FLT3-TKD mutation F691L.

In one embodiment, the host is suffering from acute promyelocytic leukemia (a subtype of AML); a minimally differentiated AML (M0); myeloblastic leukemia (M1; with/ without minimal cell maturation); myeloblastic leukemia (M2; with cell maturation); promyelocytic leukemia (M3 or M3 variant [M3V]); myelomonocytic leukemia (M4 or M4 variant with eosinophilia [M4E]); monocytic leukemia (M5); erythroleukemia (M6); or megakaryocytic leukemia (M7). In one embodiment, the host is suffering from AML that has relapsed or become refractory to previous treatments. In one embodiment, the host has previously been treated with a FLT3 inhibitor or other chemotherapeutic agent.

In one embodiment, the host is suffering from AML having both FLT3-ITD and FLT3-TKD mutations, wherein resistance to other FLT3 inhibitors, for example, AC220, has been established. In one embodiment, the host has an AML tumor comprising a FLT3 mutation, wherein the mutation has conferred resistance to quizartinib (AC220) or other FLT3 inhibitor selected from lestaurtinib, sunitinib, sorafenib, tandutinib, midostaurin, amuvatinib crenolanib, dovitinib, ENMD-2076 (Entremed), or KW-2449 (Kyowa Hakko Kirin), or a combination thereof.

In one embodiment, the cancer treated overexpresses MerTK, Axl, or Tyro3, or a combination thereof. In one embodiment, the cancer, which overexpresses MerTK is selected from the group consisting of acute myeloid leukemia, T-cell acute lymphoid leukemia, B-cell acute lymphoid leukemia, lung cancer, glioma, melanoma, prostate cancer, schwannoma, mantle cell lymphoma, and rhabdomyosarcoma. In an alternative embodiment, the cancer ectopically expresses MerTK.

In one embodiment, the cancer treated has a mutation in the amino acid sequence of the MerTK extracellular or transmembrane domain selected from P40S (melanoma), S159F (lung), E204K (urinary tract) S428G (gastric), I431F (lung), A446G (kidney), N4545 (liver), W485S/C (lymphoma), and V486I (melanoma). In one embodiment the cancer treated has a mutation in the amino acid sequence of the MerTK cytosolic domain mutation selected from L586F (urinary tract), G594R (breast), S626C (urinary tract), P672S (lung), L688M (colon), A7085 (head and neck), N718Y (lung), R722stop (colon), M790V (lung), P802S (melanoma), V873I (liver), S905F (lung), K923R (melanoma), P958L (kidney), D983N (liver), and D990N (colon).

In one embodiment, the cancer is a MerTK-negative (−/−) cancer.

In one embodiment, a compound of Formula I, II, III, IV, V, VI, VII, or VIII, as described herein, in combination with an immune checkpoint inhibitor, is provided for use in treating colon cancer. In one embodiment, the immune checkpoint inhibitor is an anti-programmed cell death-1 (PD1) antibody. In one embodiment, the immune checkpoint inhibitor is an anti-CTLA4 antibody. In one embodiment, a compound of Formula I, II, III, IV, V, VI, or VII is administered in combination with pembrolizumab. In one embodiment, a compound of Formula I, II, III, IV, V, VI, or VII is administered in combination with nivolumab. In one embodiment, a compound of Formula I, II, III, IV, V, VI, or VII is administered in combination with an anti-CTLA4 antibody. In one embodiment, a compound of Formula I, II, III, IV, V, VI, or VII is administered in combination with ipilimumab. In one embodiment, the pan-TAM and.or MerTK/AXL inhibitor compound administered is selected from the compound of Tables 1-5. In embodiments, a compound of Formula I, II, III, IV, V, VI, VII, or VIII, as described herein, in combination with an immune checkpoint inhibitor is further combined with a TLR agonist and/or ionizing radiation.

In one embodiment, a compound of Formula I, II, III, IV, V, VI, VII, or VIII, as described herein, in combination with an immune checkpoint inhibitor, is provided for use in treating a non-small cell lung carcinoma (NSCLC). In one embodiment, the immune checkpoint inhibitor is an anti-programmed cell death-1 (PD1) antibody. In one embodiment, the immune checkpoint inhibitor is an anti-CTLA4 antibody. In one embodiment, a compound of Formula I, II, III, IV, V, VI, or VII is administered in combination with pembrolizumab. In one embodiment, a compound of Formula I, II, III, IV, V, VI, or VII is administered in combination with nivolumab. In one embodiment, a compound of Formula I, II, III, IV, V, VI, or VII is administered in combination with an anti-CTLA4 antibody. In one embodiment, a compound of Formula I, II, III, IV, V, VI, or VII is administered in combination with ipilimumab. In one embodiment, the pan-TAM and.or MerTK/AXL inhibitor compound administered is selected from the compound of Tables 1-5. In embodiments, a compound of Formula I, II, III, IV, V, VI, VII, or VIII, as described herein, in combination with an immune checkpoint inhibitor is further combined with a TLR agonist and/or ionizing radiation.

In one embodiment, a compound of Formula I, as described herein, in combination with an immune checkpoint inhibitor, is provided for use in treating prostate cancer. In one embodiment, the immune checkpoint inhibitor is an anti-programmed cell death-1 (PD1) antibody. In one embodiment, the immune checkpoint inhibitor is an anti-CTLA4 antibody. In one embodiment, a compound of Formula I, II, III, IV, V, VI, or VII is administered in combination with pembrolizumab. In one embodiment, a compound of Formula I, II, III, IV, V, VI, or VII is administered in combination with nivolumab. In one embodiment, a compound of Formula I, II, III, IV, V, VI, or VII is administered in combination with an anti-CTLA4 antibody. In one embodiment, a compound of Formula I, II, III, IV, V, VI, or VII is administered in combination with ipilimumab. In one embodiment, the pan-TAM and.or MerTK/AXL inhibitor compound administered is selected from the compound of Tables 1-5. In embodiments, a compound of Formula I, II, III, IV, V, VI, VII, or VIII, as described herein, in combination with an immune checkpoint inhibitor is further combined with a TLR agonist and/or ionizing radiation.

In one embodiment, a compound of Formula I, II, III, IV, V, VI, VII, or VIII, as described herein, in combination with an immune checkpoint inhibitor, is provided for use in treating a melanoma. In one embodiment, the immune checkpoint inhibitor is an anti-programmed cell death-1 (PD1) antibody. In one embodiment, the immune checkpoint inhibitor is an anti-CTLA4 antibody. In one embodiment, the host does not have a melanoma with a B-RAF mutation. In one embodiment, the host has a melanoma with a B-RAF mutation. In one embodiment, the host has a melanoma with a RAS mutation. In one embodiment, the melanoma overexpresses MerTK. In one embodiment, the melanoma has metastasized. In one embodiment, a compound of Formula I, II, III, IV, V, VI, or VII is administered in combination with pembrolizumab. In one embodiment, a compound of Formula I, II, III, IV, V, VI, or VII is administered in combination with nivolumab. In one embodiment, a compound of Formula I, II, III, IV, V, VI, or VII is administered in combination with an anti-CTLA4 antibody. In one embodiment, a compound of Formula I, II, III, IV, V, VI, or VII is administered in combination with ipilimumab. In one embodiment, the pan-TAM and/or MerTK/AXL inhibitor compound administered is selected from the compound of Tables 1-5. In embodiments, a compound of Formula I, II, III, IV, V, VI, VII, or VIII, as described herein, in combination with an immune checkpoint inhibitor is further combined with a TLR agonist and/or ionizing radiation.

In one embodiment, a compound of Formula I, II, III, IV, V, VI, VII, or VIII, as described herein, in combination with an immune checkpoint inhibitor, is provided for use in treating Acute Lymphoblastic Leukemia (ALL). In one embodiment, a method is provided to treat a host with ALL comprising administering to the host an effective amount of a compound of Formula I, II, III, IV, V, VI, or VII in combination with an immune checkpoint inhibitor. In one embodiment, the pan-TAM and.or MerTK/AXL inhibitor compound administered is selected from the compound of Tables 1-5. In embodiments, a compound of Formula I, II, III, IV, V, VI, VII, or VIII, as described herein, in combination with an immune checkpoint inhibitor is further combined with a TLR agonist and/or ionizing radiation.

In one embodiment, a compound of Formula I, II, III, IV, V, VI, VII, or VIII, as described herein, in combination with an immune checkpoint inhibitor, is provided for use in treating Acute Myeloid Leukemia (AML). In one embodiment, the AML contains a wild type FLT3 protein. In one embodiment, the replication of the AML cells are dependent on FLT3 expression. In one embodiment, the AML contains a FLT3-ITD mutation. In one embodiment, the AML contains a FLT3-TKD mutation. In one embodiment, the AML contains both a FLT3-ITD and FLT3-TKD mutation. In one embodiment, a pan-TAM and/or MerTK/AXL inhibitor compound described herein is administered to a host suffering from AML, wherein the AML contains a mutation within the FLT3-TKD at amino acid F691 or D835. In one embodiment, the pan-TAM and/or MerTK/AXL inhibitor compound administered is selected from the compound of Tables 1-5. In embodiments, a compound of Formula I, II, III, IV, V, VI, VII, or VIII, as described herein, in combination with an immune checkpoint inhibitor is further combined with a TLR agonist and/or ionizing radiation.

The present invention is explained in greater detail in the following non-limiting Examples.

EXAMPLES

Example 1 trans-4-((5-(Pyridin-2-yl)-2-((4-vinylphenyl)amino)pyrimidin-4-yl)amino)cyclohexan-1-ol General Procedure A:

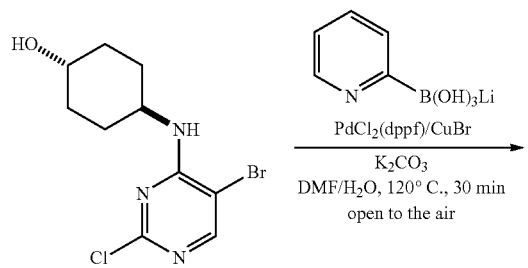

-continued

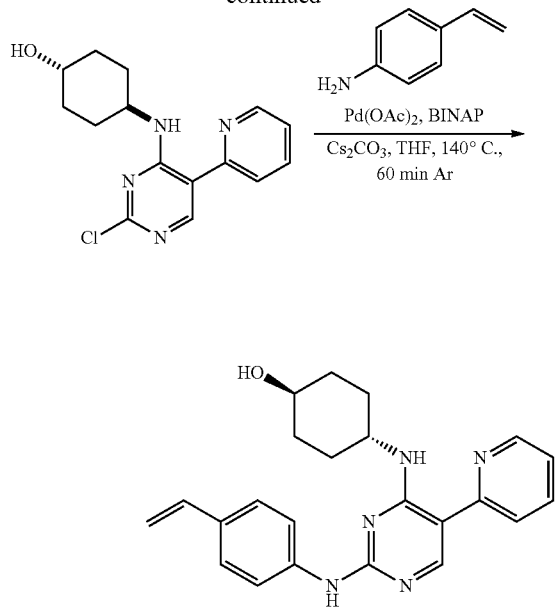

To a mixture of 2-pyridinyl trihydroxyborate lithium (1.32 g, 9 mmol, 3.0 eq.), copper bromide (85.8 mg, 0.6 mmol, 0.2 eq.) in a mixture of DMF and $H_2O$ (4:1, 15 mL) was added potassium carbonate (1.24 g, 9.0 mmol, 3.0 eq.), 4-((5-bromo-2-chloropyrimidin-4-yl)amino)cyclohexan-1-ol (1.12 g, 3.0 mmol, 1.0 eq), and $PdCl_2$(dppf) (246 mg, 0.30 mmol, 0.1 eq.). The resulting mixture was heated at 120° C. in the open air for 30 min, then allowed to cool to room temperature. The insoluble material was removed by filtration through a short pad of celite, which was washed with DMF. The solvents were removed under the reduced pressure. The residue was filtered through a short pad of silica gel to remove the palladium black. The crude product was used without further purification.

To a solution of crude 4-((2'-chloro-[4,5'-bipyrimidin]-4'-yl)amino)cyclohexanol (183 mg, 0.6 mmol) and 4-vinylaniline (86 mg, 0.72 mmol) in THF (1.5 mL) was added $Pd(OAc)_2$ (45 mg, 0.12 mmol), BINAP (75.0 mg, 0.12 mmol) and $Cs_2CO_3$ (470 mg, 0.72 mmol) in sequence. The resulting mixture was heated at 140° C. in the open air for 30 min, then allowed to cool to room temperature. The solvent was removed and the residue was purified by with dry loading to afford the title compound (104 mg, 31%) (UNC3204A). $^1$H NMR (400 MHz, $CD_3OD$) δ 8.70-8.68 (m, 1H), 8.36 (s, 1H), 8.10 (dt, $J_1$=2.0 Hz, $J_2$=8.0 Hz, 1H), 7.99 (d, J=8.0 Hz, 1H), 7.59-7.52 (m, 5H), 7.76 (dd, $J_1$=2.0 Hz, $J_2$=8.0 Hz, 1H), 5.81 (dd, $J_1$=2.0 Hz, $J_2$=20.0 Hz, 1H), 5.27 (dd, $J_1$=2.0 Hz, $J_2$=12.0 Hz, 1H), 4.15-4.05 (m, 1H), 3.69-3.60 (m, 1H), 2.20-2.10 (m, 2H), 2.06-1.96 (m, 2H), 1. column chromatography with ISCO system 60-1.58 (m, 2H), 1.50-1.35 (m, 2H). MS m/z 388.49 [M+H]$^+$.

TABLE 1

*describes compounds could be prepared following procedures described in Example 1, using appropriate reagents. (Note: IC50: ++++ means <10 nM; +++ means between 10-100 nM, ++ means between 100 nM-1 μM; + means between 1-30 μM; – means inactive.)*

| | Structure | Compound_ID | Mer IC$_{50}$ | Axl IC$_{50}$ | Tyro3 IC$_{50}$ | Physical Data MS m/z (M + 1) or/and $^1$H NMR |
|---|---|---|---|---|---|---|
| 1 | 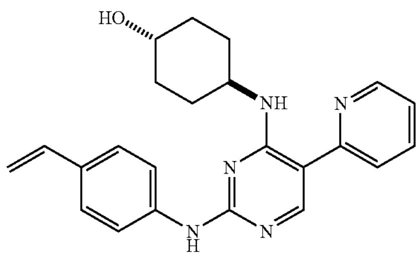 | UNC3204A | +++ | ++ | +++ | $^1$H NMR (400 MHz, CD$_3$OD) δ 8.70-8.68 (m, 1H), 8.36 (s, 1H), 8.10 (dt, J$_1$ = 2.0 Hz, J$_2$ = 8.0 Hz, 1H), 7.99 (d, J = 8.0 Hz, 1H), 7.59-7.52 (m, 5H), 7.76 (dd, J$_1$ = 2.0 Hz, J$_2$ = 8.0 Hz, 1H), 5.81 (dd, J$_1$ = 2.0 Hz, J$_2$ = 20.0 Hz, 1H), 5.27 (dd, J$_1$ = 2.0 Hz, J$_2$ = 12.0 Hz, 1H), 4.15-4.05 (m, 1H), 3.69-3.60 (m, 1H), 2.20-2.10 (m, 2H), 2.06-1.96 (m, 2H), 1.60-1.58 (m, 2H), 1.50-1.35 (m, 2H). MS m/z 388.49 [M + H]$^+$. |
| 2 | 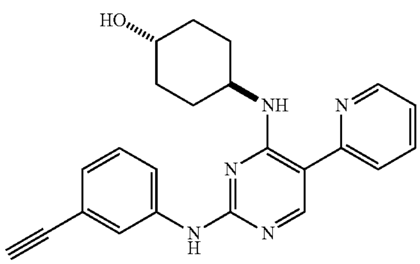 | UNC3223A | ++++ | ++ | ++++ | $^1$H NMR (400 MHz, CD$_3$OD) δ 8.64 (dd, J$_1$ = 2.0 Hz, J$_2$ = 4.0 Hz, 1H), 8.43 (s, 1H), 7.90-7.98 (m, 3H), 7.47-7.36 (m, 4H), 4.20-4.06 (m, 1H), 3.82-3.63 (m, 1H), 3.61 (s, 1H), 2.21-2.15 (m, 2H), 2.06-1.98 (m, 2H), 1.60-1.45 (m, 4H). MS m/z 386.47 [M + H]$^+$. |
| 3 | 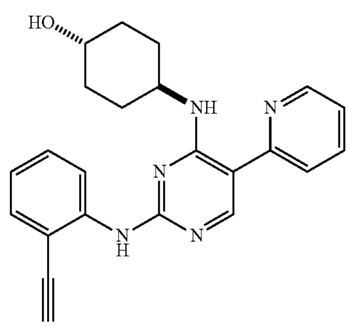 | UNC3206A | + | | + | $^1$H NMR (400 MHz, CD3OD) δ 8.91 (s, 1H), 7.75 (dd, J$_1$ = 2.0 Hz, J$_2$ = 8.0 Hz, 1H), 8.17 (d, J = 8.0 Hz, 1H), 8.06 (dt, J$_1$ = 2.0 Hz, J$_2$ = 8.0 Hz, 1H), 7.63 (dd, J$_1$ = 2.0 Hz, J$_2$ = 8.0 Hz, 1H), 7.57-7.52 (m, 2H), 7.36 (ddd, J$_1$ = 2.0 Hz, J$_2$ = 4.0 Hz, J$_3$ = 8.0 Hz, 2H), 7.09 (s, 1H), 4.48-4.35 (m, 1H), 3.76-3.60 (m, 1H), 2.30-2.22 (m, 2H), 2.10-2.02 (m, 2H), 1.70-1.58 (m, 2H), 1.53-1.40 (m, 2H). MS m/z 386.46 [M + H]$^+$. |
| 4 | 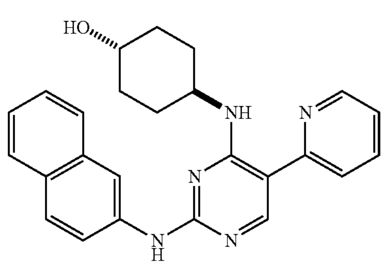 | UNC3207A | +++ | ++ | +++ | $^1$H NMR (400 MHz, d-DMSO) δ 11.33 (s, 1H), 10.92 (s, 1H), 8.72 (s, 1H), 8.62 (s, 1H), 8.22 (s, 1H), 8.06-7.78 (m, 3H), 7.66 (s, 1H), 7.51 (s, 1H), 7.44 (s, 1H), 5.69 (s, 1H), 3.99 (s, 1H), 3.13 (s, 1H), 2.11-1.80 (m, 4H), 1.60-1.11 (m, 4H). MS m/z 412.51 [M + H]$^+$. |
| 5 | 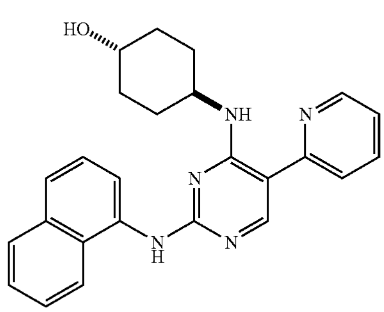 | UNC3205A | | | +++ | $^1$H NMR (400 MHz, d-DMSO) δ 11.03 (d, J = 2.0 Hz, 1H), 10.52 (s, 1H), 8.61 (dt, J$_1$ = 2.0 Hz, J$_2$ = 8.0 Hz, 1H), 8.56 (br, 1H), 8.07-7.92 (m, 4H), 7.76 (d, J = 8.0 Hz, 1H), 7.61-7.55 (m, 2H), 7.48-7.41 (m, 1H), 1.80-1.68 (m, 4H), 1.32-1.20 (m, 2H), 0.98-0.93 (m, 2H). MS m/z 412.51 [M + H]$^+$. |

TABLE 1-continued

*describes compounds could be prepared following procedures described in Example 1, using appropriate reagents. (Note: IC50: ++++ means <10 nM; +++ means between 10-100 nM; ++ means between 100 nM-1 μM; + means between 1-30 μM; − means inactive.)*

| Structure | Compound_ID | Mer IC$_{50}$ | Axl IC$_{50}$ | Tyro3 IC$_{50}$ | Physical Data MS m/z (M + 1) or/and $^1$H NMR |
|---|---|---|---|---|---|
| 6 | UNC3224A | ++ |  | +++ | $^1$H NMR (400 MHz, d-DMSO) δ 8.70 (ddd, J$_1$ = 2.0 Hz, J$_2$ = 4.0 Hz, J$_3$ = 8.0 Hz, 2H), 8.56 (s, 1H), 8.43 (ddd, J$_1$ = 2.0 Hz, J$_2$ = 4.0 Hz, J$_3$ = 8.0 Hz, 2H), 8.11 (td, J$_1$ = 2.0 Hz, J$_2$ = 8.0 Hz, 1H), 8.11 (dt, J$_1$ = 2.0 Hz, J$_2$ = 8.0 Hz, 1H), 7.95 (ddd, J$_1$ = 2.0 Hz, J$_2$ = 4.0 Hz, J$_3$ = 8.0 Hz, 1H), 7.57 (ddd, J$_1$ = 2.0 Hz, J$_2$ = 4.0 Hz, J$_3$ = 8.0 Hz, 1H), 7.26 (td, J$_1$ = 2.0 Hz, J$_2$ = 8.0 Hz, 2H), 4.28-4.20 (m, 1H), 3.72-3.65 (m, 1H), 2.22-2.14 (m, 2H), 2.07-2.00 (m, 2H), 1.60-1.40 (m, 4H). MS m/z 363.44 [M + H]$^+$. |
| 7 | UNC3209A | ++++ | ++ | +++ | $^1$H NMR (400 MHz, CD3OD) δ 9.35 (d, J = 2.0 Hz, 1H), 8.88 (d, J = 2.0 Hz, 1H), 8.76-8.73 (m, 2H), 8.56 (s, 1H), 8.23-8.13 (s, 2H), 8.11 (d, J = 8.0 Hz, 1H), 7.68-7.65 (m, 1H), 4.13-4.07 (m, 1H), 3.70-3.64 (m, 1H), 2.16-2.12 (m, 2H), 2.04-2.00 (m, 2 H), 1.58-1.44 (m, 4 H). MS m/z 412.51 [M + H]$^+$. |
| 8 | UNC3208A | ++++ | +++ | ++++ | $^1$H NMR (400 MHz, d-DMSO) δ 11.12 (s, 1H), 10.27 (d, J = 8.0 Hz, 1H), 8.78 (s, 1H), 8.62 (ddd, J$_1$ = 2.0 Hz, J$_2$ = 4.0 Hz, 8.0 Hz, 2H), 8.56 (d, J = 4.0 Hz, 2H), 8.23 (d, J = 8.0 Hz, 2H), 8.07 (d, J = 8.0 Hz, 1H), 7.93 (td, J$_1$ = 2.0 Hz, J$_2$ = 8.0 Hz, 1H), 7.38 (ddd, J$_1$ = 2.0 Hz, J$_2$ = 4.0 Hz, J$_3$ = 8.0 Hz, 1H), 3.98 (s, 1H), 2.11-2.00 (m, 2H), 1.90-1.80 (m, 2H), 1.45-1.32 (m, 4H). MS m/z 412.51 [M + H]$^+$. |
| 9 | UNC4240A | ++++ | ++ | ++++ | $^1$H NMR (400 MHz, CD$_3$OD) δ 8.79 (s, 1H), 8.44 (m, 1H), 8.13-8.05 (m, 2H), 7.43 (d, J = 8.0 Hz, 2H), 7.03 (d, J = 8.0 Hz, 2H), 4.51 (s, 2H), 4.09-4.08 (m, 1H), 3.86 (s, 1H), 3.64-3.48 (m, 3H), 3.26-3.21 (m, 3H), 2.23-1.99 (m, 9H), 1.57-1.39 (m, 4H); MS m/z 475.30 [M + 1]$^+$. |
| 10 | UNC4241A | ++++ | ++++ | ++++ | $^1$H NMR (400 MHz, CD$_3$OD) δ 8.79 (s, 1H), 8.50 (m, 1H), 8.14-8.07 (m, 2H), 7.58-7.55 (m. 2H), 7.25-7.20 (m, 2H), 4.52 (s, 2H), 4.06-4.03 (m, 1H), 3.65-3.47 (m, 3H), 3.21-3.28 (m, 2H), 2.16-1.99 (m, 8H), 1.54-1.38 (m, 4H); MS m/z 463.30 [M + 1]$^+$. |

TABLE 1-continued

*describes compounds could be prepared following procedures described in Example 1, using appropriate reagents. (Note: IC50: ++++ means <10 nM; +++ means between 10-100 nM; ++ means between 100 nM-1 µM; + means between 1-30 µM; − means inactive.)*

| Structure | Compound_ID | Mer IC$_{50}$ | Axl IC$_{50}$ | Tyro3 IC$_{50}$ | Physical Data MS m/z (M + 1) or/and $^1$H NMR |
|---|---|---|---|---|---|
| 11 | UNC4242A | ++++ | ++++ | ++++ | $^1$H NMR (400 MHz, CD$_3$OD) δ 8.74 (s, 1H), 8.49 (s, 1H), 8.05-8.02 (m, 2H), 7.48 (d, J = 8.0 Hz, 2H), 7.24 (d, J = 8.0 Hz, 2H), 4.49 (s, 2H), 4.11-4.08 (m, 1H), 3.66-3.48 (m, 3H), 3.27-3.24 (m, 2H), 2.37 (s, 3H), 2.22-1.99 (m, 8H), 1.52-1.43 (m, 4H); MS m/z 459.30 [M + 1]$^+$. |
| 12 | UNC4243A | ++++ | +++ | ++++ | $^1$H NMR (400 MHz, CD$_3$OD) δ 8.79 (s, 1H), 8.60 (s, 1H), 8.11-8.13 (m, 2H), 7.86 (d, J = 8.0 Hz, 2H), 7.75 (d, J = 8.0 Hz, 2H), 4.52 (s, 2H), 4.15-4.09 (m, 1H), 3.69-3.55 (m, 3H), 3.22-3.29 (m, 2H), 2.27-2.01 (m, 8H), 1.57-1.44 (m, 4H); MS m/z 513.30 [M + 1]$^+$. |
| 13 | UNC4244A | ++++ | +++ | ++++ | $^1$H NMR (400 MHz, CD$_3$OD) δ 8.79 (s, 1H), 8.56 (s, 1H), 8.10-8.08 (m, 2H), 7.77-7.75 (m, 1H), 7.39-7.29 (m, 3H), 4.52 (s, 2H), 4.01-3.94 (m, 1H), 3.64-3.48 (m, 3H), 3.21-3.26 (m, 2H), 2.23-1.98 (m, 8H), 1.52-1.32 (m, 4H); MS m/z 463.30 [M + 1]$^+$. |
| 14 | UNC4247A | ++++ | ++++ | ++++ | $^1$H NMR (400 MHz, CD$_3$OD) δ 8.78 (s, 1H), 8.53 (s, 1H), 8.14-8.07 (m, 2H), 7.61-7.58 (m, 1H), 7.45-7.42 (m, 1H), 7.30-7.27 (m, 1H), 7.03-6.99 (m, 1H), 4.50 (s, 2H), 4.07-4.11 (m, 1H), 3.66-3.53 (m, 2H), 3.23-3.19 (m, 3H), 2.21-1.97 (m, 8H), 1.64-1.39 (m, 4H); MS m/z 463.30 [M + 1]$^+$. |
| 15 | UNC4372A | ++++ | ++++ | ++++ | $^1$H NMR (400 MHz, CD$_3$OD) δ 8.81 (d, J = 1.6 Hz, 1H), 8.62 (s, 1H), 8.20-8.10 (m, 2H), 7.87-7.81 (m, 4H), 4.52 (s, 2H), 4.15-4.08 (m, 1H), 3.69-3.55 (m, 3H), 2.21-1.98 (m, 9H), 1.62-1.41 (m, 4H); MS m/z 470.30 [M + 1]$^+$. |

TABLE 1-continued

*describes compounds could be prepared following procedures described in Example 1, using appropriate reagents. (Note: IC50: ++++ means <10 nM; +++ means between 10-100 nM; ++ means between 100 nM-1 µM; + means between 1-30 µM; – means inactive.)*

| | Structure | Compound_ID | Mer IC$_{50}$ | Axl IC$_{50}$ | Tyro3 IC$_{50}$ | Physical Data MS m/z (M + 1) or/and $^1$H NMR |
|---|---|---|---|---|---|---|
| 16 | (structure) | UNC4373A | ++++ | ++++ | ++++ | $^1$H NMR (400 MHz, CD$_3$OD) δ 8.78 (s, 1H), 8.53 (s, 1H), 8.16-8.07 (m, 2H), 7.59 (d, J = 8.8 Hz, 2H), 7.46 (d, J = 8.8 Hz, 2H), 4.51 (s, 2H), 4.08-4.04 (m, 1H), 3.66-3.56 (m, 3H), 2.22-2.02 (m, 8H), 1.55-1.41 (m, 4H); MS m/z 479.30 [M + 1]$^+$. |
| 17 | (structure) | UNC4377A | ++++ | ++++ | ++++ | $^1$H NMR (400 MHz, CD$_3$OD) δ 8.54 (s, 1H), 8.13 (s, 1H), 8.16-8.07 (m, 2H), 7.61-7.54 (m, 4H), 4.51 (s, 2H), 4.10-4.05 (m, 1H), 3.66-3.52 (m, 3H), 2.18-1.98 (m, 8H), 1.58-1.38 (m, 4H); MS m/z 523.20 [M + 1]$^+$. |
| 18 | (structure) | UNC4397A | ++++ | ++++ | ++++ | $^1$H NMR (400 MHz, CD$_3$OD) δ 8.55 (s, 1H), 8.43 (s, 1H), 7.96-7.84 (m, 2H), 7.59-7.56 (m, 2H), 7.23-7.19 (m, 2H), 6.57 (s, 1H), 4.06-4.01 (m, 1H), 3.75-3.52 (m, 6H), 3.16-3.03 (m, 3H), 2.90-2.64 (m, 3H), 2.15-2.12 (m, 2H), 2.04-1.96 (m, 2H), 1.57-1.47 (m, 2H), 1.39 (m, 8H); MS m/z 517.30 [M + 1]$^+$. |
| 19 | (structure) | UNC4398A | ++++ | +++ | ++++ | $^1$H NMR (400 MHz, CD$_3$OD) δ 8.55 (s, 1H), 8.42 (s, 1H), 7.97-7.86 (m, 2H), 7.59-7.56 (m, 2H), 7.24-7.19 (m, 2H), 4.06-4.00 (m, 1H), 3.75-3.48 (m, 6H), 3.16-2.73 (m, 7H), 2.13-1.91 (m, 6H), 1.59-1.34 (m, 5H); MS m/z 419.35 [M + 1]$^+$. |
| 20 | (structure) | UNC3029A | ++++ | ++ | ++++ | $^1$H NMR (400 MHz, CD$_3$OD) δ 8.63 (d, J = 5.0 Hz, 1H), 8.37 (s, 1H), 7.97 (ddd, J = 21.5, 11.2, 4.9 Hz, 2H), 7.56 (d, J = 8.1 Hz, 2H), 7.52-7.38 (m, 3H), 7.27 (t, J = 7.4 Hz, 1H), 4.07 (ddd, J = 14.7, 9.3, 3.8 Hz, 1H), 3.64 (ddd, J = 14.3, 10.0, 4.1 Hz, 1H), 2.14 (dd, J = 12.9, 2.8 Hz, 2H), 2.00 (dd, J = 13.1, 3.3 Hz, 2H), 1.59-1.44 (m, 2H), 1.39 (ddd, J = 23.3, 12.8, 3.1 Hz, 2H). MS m/z 362.0 [M + 1]$^+$. |

TABLE 1-continued describes compounds could be prepared following procedures described in Example 1, using appropriate reagents. (Note: IC50: ++++ means <10 nM; +++ means between 10-100 nM, ++ means between 100 nM-1 μM; + means between 1-30 μM; − means inactive.)

| | Structure | Compound_ID | Mer IC$_{50}$ | Axl IC$_{50}$ | Tyro3 IC$_{50}$ | Physical Data MS m/z (M + 1) or/and $^1$H NMR |
|---|---|---|---|---|---|---|
| 21 | 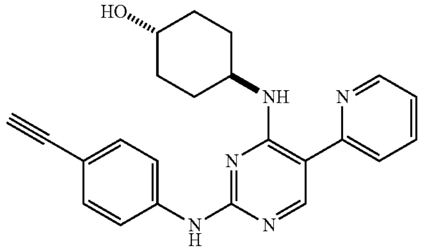 | UNC3203A | ++++ | +++ | ++++ | $^1$H NMR (400 MHz, CD3OD) δ 8.65-8.61 (m, 1H), 8.43 (s, 1H), 8.08 (d, J = 8.0 Hz, 1H), 7.98-7.92 (m, 1H), 7.81-7.73 (m, 1H), 7.63 (d, J = 8.0 Hz, 1H), 7.61 (d, J = 8.0 Hz, 1H), 7.56-7.52 (m, 1H), 7.45-7.41 (m, 1H), 4.15-4.05 (m, 1H), 3.72-3.63 (m, 1H), 3.51 (s, 1H), 2.18 (d, J = 8.0 Hz, 1H), 2.04 (d, J = 8.0 Hz, 1H), 1.63-1.35 (s, 4H), 1.00 (d, J = 8.0 Hz, 3H), 0.96-0.85 (m, 3H). MS m/z 386.46 [M + H]$^+$. |
| 22 | 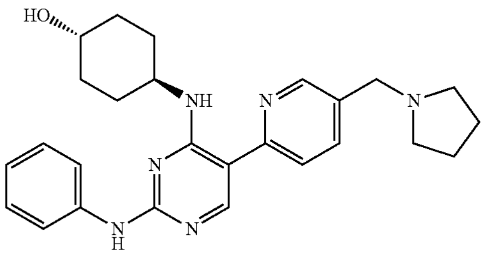 [SMILES: O[C@H]1CC[C@H](Nc2nc(Nc3ccccc3)ncc2-c2ccc(CN3CCCC3)cn2)CC1] | UNC4198A | ++++ | ++++ | ++++ | $^1$H NMR (400 MHz, CD$_3$OD) δ: 8.78 (d, J = 2.0 Hz, 1H), 8.49 (s, 1H), 8.15 (dd, J$_1$ = 4.0 Hz, J$_2$ = 8.0 Hz, 1H), 8.05 (d, J = 8.0 Hz, 1H), 7.56 (d, J = 8.0 Hz, 2H), 7.45 (t, J = 8.0 Hz, 2H), 7.28 (t, J = 8.0 Hz, 1H), 4.50 (s, 2H), 4.12-4.03 (m, 1H), 3.68-3.59 (m. 1H), 3.59-3.51 (m, 2H), 3.26-3.18 (m, 2H), 2.26-2.10 (m, 2H), 2.09-1.95 (m, 2H), 1.57-1.46 (m, 2H), 1.45-1.34 (m, 2H); MS m/z 445.3 [M + 1]$^+$. |

Example 2 trans-4-((5-(pyridin-2-yl)-2-((4-(pyridin-4-yl)phenyl)amino)pyrimidin-4-yl)amino)cyclohexan-1-ol General Procedure B:

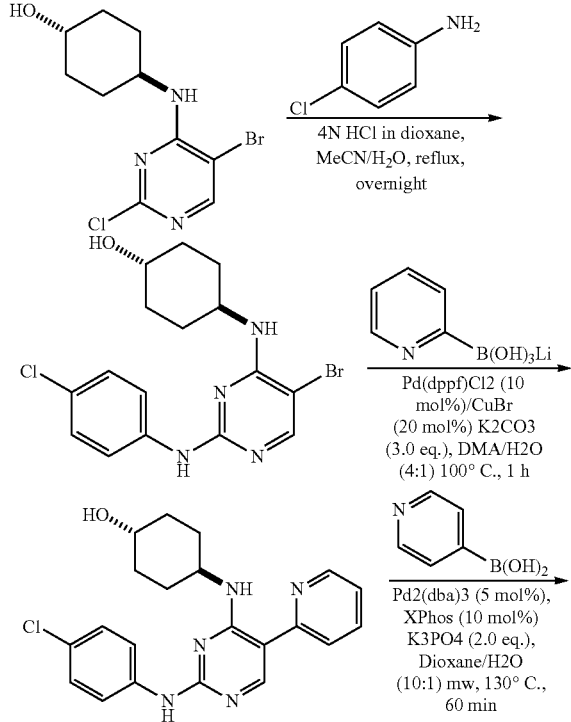

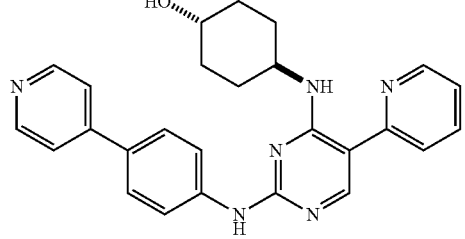

To a solution of trans-4-((5-bromo-2-chloropyrimidin-4-yl)amino)cyclohexan-1-ol (6.12 g, 20 mmol, 1.0 equivalent) and 4-chloroaniline (3.05 g, 24 mmol, 1.2 equivalent) a mixture of MeCN (20 mL) and H$_2$O (5.0 mL) was added a 4.0 N solution of HCl in dioxane (5.0 mL). The reaction mixture was heated under reflux overnight. A large amount of white solid was formed during the reaction which was filtered and washed by small amount of DCM (5.0 mL×2) to provide the desired product trans-4-((5-bromo-2-((4-chlorophenyl)amino)pyrimidin-4-yl)amino)cyclohexan-1-ol as white solid (8.0 g, 85%). $^1$H NMR (CD$_3$OD, 400 MHz): 8.04 (s, 1H), 7.52 (d, J=8.0 Hz, 2H), 7.42 (d, J=8.0 Hz, 2H), 4.02-3.96 (m, 1H), 3.60-3.53 (m, 1H), 2.05-1.93 (m, 4H), 1.62-1.52 (m, 2H), 1.36-1.26 (m, 2H).

To a solution of trans-4-((5-bromo-2-((4-chlorophenyl)amino)pyrimidin-4-yl)amino) cyclohexan-1-ol (2.3 g, 5.0 mmol) in DMF (24 mL) was added a solution of K$_2$CO$_3$ (3.45 g, 25 mmol) in H$_2$O (6.0 mL) in the open air at room temperature. After stirring for about 3 minutes, the 2-bronic acids pyridine lithium salt (2.2 g, 15.0 mmol) was added. The reaction mixture was stirred for 20 min, then was added Pd(dppf)Cl$_2$ (408 mg, 0.50 mmol, 10 mol %) and CuBr (142 mg, 1.0 mmol, 20 mol %) in one portion. The resulting reaction mixture was heated at 110° C. for 45 min. After filtration and concentration, the crude product (black solid) was purified by column chromatography with ISCO system to afford the desired compound trans-4-((2-((4-chlorophenyl)amino)-5-(pyridin-2-yl)pyrimidin-4-yl)amino)cyclohexan-1-ol as a light yellow solid (1.0 g, 25%). NMR (DMSO-D$_6$, 400 MHz): 10.0 (d, J=12.0 Hz, 1H), 9.45 (s, 1H), 8.62 (s, 1H), 8.51 (d, J=4.0 Hz, 1H), 7.94 (d, J=8.0 Hz, 2H), 7.83 (d, J=8.0 Hz, 2H), 7.79-7.77 (m, 1H), 7.25 (d, J=8.0 Hz, 1H), 7.20 (dd, J$_1$=8.0 Hz, J$_2$=4.0 Hz, 1H), 4.54 (d, J=4.0 Hz, 1H), 3.91 (m, 1H), 2.08-2.04 (m, 2H), 1.88-1.84 (m, 2H), 1.35-1.27 (m, 4H).

To a mixture of trans-4-((2-((4-chlorophenyl)amino)-5-(pyridin-2-yl)pyrimidin-4-yl)amino)cyclohexan-1-ol (40 mg, 0.10 mmol), 2-bronic acids pyridine lithium salt (32 mg, 0.20 mmol), Pd$_2$(dba)$_3$ (5 mol %), XPhos (10 mol %) and K$_3$PO$_4$ (63.6 mg, 0.30 mmol) in a mixture of dioxane/H$_2$O (4:1, 2.0 mL) was heated under microwave irradiation at 130° C. for 60 min under N$_2$ atmosphere and then passed through a pad of celite. The solvent was removed under reduced pressure and the crude product was purified by column chromatography through preparative HPLC to afford the title compound as a white solid (38 mg, 88%) (UNC4433A). $^1$H NMR (CD$_3$OD, 400 MHz): 8.84 (s, 1H), 8.67 (d, J=8.0 Hz, 1H), 8.50 (s, 1H), 8.44 (d, J=8.0 Hz, 2H), 8.12 (d, J=8.0 Hz, 2H), 8.07-7.99 (m, 2H), 7.95 (d, J=8.0 Hz, 2H), 7.52-7.49 (m, 1H), 4.17-4.11 (m, 1H), 3.72-3.64 (m, 1H), 2.19 (d, J=8.0 Hz, 2H), 2.04 (d, J=8.0 Hz, 2H), 1.62-1.41 (m, 4H); MS m/z 439.22 [M+H]$^+$.

TABLE 2 describes compounds could be prepared following procedures described in Example 2, using appropriate reagents.

| | Structure | Compound_ID | Mer IC$_{50}$ | Axl IC$_{50}$ | Tyro3 IC$_{50}$ | Physical Data MS m/z (M + 1) or/and $^1$H NMR |
|---|---|---|---|---|---|---|
| 1 | (structure) | UNC4434A | +++ | ++ | ++ | $^1$H NMR (CD$_3$OD 400 MHz): δ 8.65 (d, J = 4.0 Hz, 1H), 8.36 (s, 1H), 8.03-7.99 (m, 1H), 7.94 (d, J = 8.0 Hz, 1H), 7.55 (d, J = 8.0 Hz, 2H), 7.52 (d, J = 8.0 Hz, 2H), 7.49-7.46 (m, 1H), 6.22 (s, 1H), 4.30 (q, J = 4.0 Hz, 2H), 4.10-4.06 (m, 1H), 3.92 (t, J = 4.0 Hz, 1H), 3.68-3.60 (m, 1H), 2.55-2.50 (m, 2H), 2.14 (d, J = 8.0 Hz, 2H), 2.01 (d, J = 8.0 Hz, 2H), 1.57-1.47 (m, 2H), 1.46-1.35 (m, 2H). MS m/z 444.23 [M + 1]$^+$. |
| 2 | (structure) | UNC4435A | ++ | + | ++ | $^1$H NMR (CD$_3$OD, 400 MHz): δ 9.24 (d, J = 4.0 Hz, 1H), 8.98 (dd, J$_1$ = 8.0 Hz, J$_2$ = 4.0 Hz, 1H), 8.83 (d, J = 8.0 Hz, 1H), 8.66 (dd, J$_1$ = 8.0 Hz, J$_2$ = 4.0 Hz, 1H), 8.48 (s, 1H), 8.18 (dd, J$_1$ = 8.0 Hz, J$_2$ = 4.0 Hz, 1H), 7.92 (d, J = 8.0 Hz, 2H), 7.90 (d, J = 8.0 Hz, 2H), 4.16-4.09 (m, 1H), 3.72-3.65 (m, 1H), 2.18 (d, J = 8.0 Hz, 2H), 2.03 (d, J = 8.0 Hz, 2H), 1.62-1.51 (m, 2H), 1.48-1.39 (m, 2H). MS m/z 439.22 [M + 1]$^+$. |
| 3 | (structure) | UNC4436A | ++ | + | ++ | $^1$H NMR (CD$_3$OD, 400 MHz): δ 8.63 (d, J = 4.0 Hz, 1H), 8.45 (s, , 1H), 7.96-7.94 (m, 2H), 7.88 (d, J = 8.0 Hz, 2H), 7.75 (s, 4H), 7.71 (d, J = 8.0 Hz, 2H), 7.44-7.40 (m, 1H), 4.14-4.07 (m, 1H), 3.73-3.67 (m, 1H), 3.33 (s, 6H), 2.18 (d, J = 8.0 Hz, 2H), 2.03 (d, J = 8.0 Hz, 2H), 1.57 (qt, J$_1$ = 12.0 Hz, |

TABLE 2-continued describes compounds could be prepared following procedures described in Example 2, using appropriate reagents.

| Structure | Compound_ID | Mer IC$_{50}$ | Axl IC$_{50}$ | Tyro3 IC$_{50}$ | Physical Data MS m/z (M + 1) or/and $^1$H NMR |
|---|---|---|---|---|---|
| | | | | | J$_2$ = 4.0 Hz, 2H), 1.42 (qt, J$_1$ = 12.0 Hz, J$_2$ = 4.0 Hz, 2H). MS m/z 481.22 [M + 1]$^+$. |
| 4 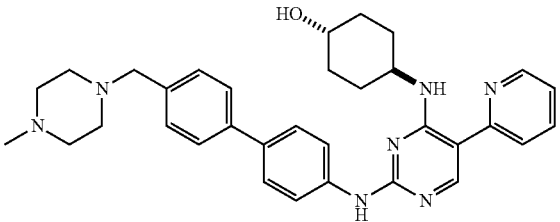 | UNC4437A | ++ | | | $^1$H NMR (CD$_3$OD + DMSO-D$_6$, 400 MHz): δ 8.64 (d, J = 4.0 Hz, 1H), 8.50 (s, 1H), 7.99-7.96 (m, 2H), 7.67 (d, J = 8.0 Hz, 2H), 7.58 (d, J = 8.0 Hz, 2H), 7.46-7.43 (m, 1H), 4.11-4.05 (m, 1H), 3.87 (m, 2H), 3.70-3.66 (m, 1H), 3.48 (t, J = 8.0 Hz, 2H), 2.86-2.82 (m, 2H), 2.17 (d, J = 8.0 Hz, 2H), 2.02 (d, J = 8.0 Hz, 2H), 1.62-1.51 (m, 2H), 1.46-1.36 (m, 2H). MS m/z 550.26 [M + H]$^+$. |
| 5 | UNC4402A | ++ | + | ++ | $^1$H NMR (CD$_3$OD + DMSO-D$_6$, 400 MHz): δ 8.64 (d, J = 4.0 Hz, 1H), 8.50 (s, 1H), 7.99-7.96 (m, 2H), 7.67 (d, J = 8.0 Hz, 2H), 7.58 (d, J = 8.0 Hz, 2H), 7.46-7.43 (m, 1H), 4.11-4.05 (m, 1H), 3.87 (m, 2H), 3.70-3.66 (m, 1H), 3.48 (t, J = 8.0 Hz, 2H), 2.86-2.82 (m, 2H), 2.17 (d, J = 8.0 Hz, 2H), 2.02 (d, J = 8.0 Hz, 2H), 1.62-1.51 (m, 2H), 1.46-1.36 (m, 2H). MS m/z 443.25 [M + H]$^+$. |
| 6 | UNC4403A | ++ | + | ++ | $^1$H NMR (CD$_3$OD, 400 MHz): δ 8.70 (d, J = 4.0 Hz, 1H), 8.35 (s, 1H), 8.12 (t, J = 8.0 Hz, 1H), 8.00 (d, J = 8.0 Hz, 1H), 7.58 (d, J = 8.0 Hz, 2H), 7.52 (d, J = 8.0 Hz, 2H), 6.18 (s, 1H), 4.23 (m, 2H), 4.12-4.18 (m, 1H), 3.83 (t, J = 8.0 Hz, 1H), 3.76 (t, J = 8.0 Hz, 1H), 3.72 (dd, J$_1$ = 8.0 Hz, J$_2$ = 4.0 Hz, 1H), 3.66-3.62 (m, 2H), 3.56 (t, J = 4.0 Hz, 1H), 3.02-2.99 (m, 2H), 2.66 (t, J = 8.0 Hz, 2H), 2.62-2.57 (m, 2H), 2.12-2.10 (m, 2H), 2.02-1.94 (m, 3H), 1.52-1.46 (m, 2H), 1.42-1.36 (m, 2H). MS m/z 538.30 [M + H]$^+$. |

TABLE 2-continued describes compounds could be prepared following procedures described in Example 2, using appropriate reagents.

| | Structure | Compound_ID | Mer IC$_{50}$ | Axl IC$_{50}$ | Tyro3 IC$_{50}$ | Physical Data MS m/z (M + 1) or/and $^1$H NMR |
|---|---|---|---|---|---|---|
| 7 | 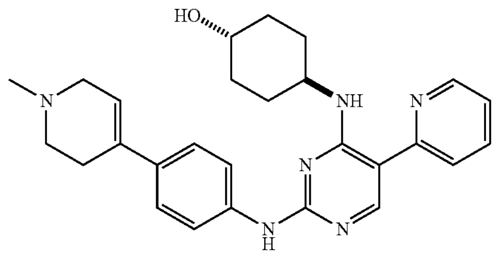 | UNC4431A | ++ | + | ++ | $^1$H NMR (CD$_3$OD + DMSO-D$_6$, 400 MHz): δ 8.65 (d, J = 4.0 Hz, 1H), 8.44 (s, 1H), 8.03-8.00 (m, 1H), 7.98 (d, J = 8.0 Hz, 1H), 7.65 (d, J = 8.0 Hz, 2H), 7.58 (d, J = 8.0 Hz, 2H), 7.51-7.48 (m, 1H), 6.20 (s, 1H), 4.09-4.05 (m, 2H), 3.85-3.80 (m, 1H), 3.75-3.70 (m, 1H), 3.66-3.61 (m, 2H), 3.40-3.25 (m, 1H), 3.01 (s, 3H), 2.97-2.91 (m, 2H), 2.14 (d, J = 8.0 Hz, 2H), 1.99 (d, J = 8.0 Hz, 2H), 1.60-1.50 (m, 2H), 1.45-1.35 (m, 2H). MS m/z 456.26 [M + H]$^+$. |
| 8 | 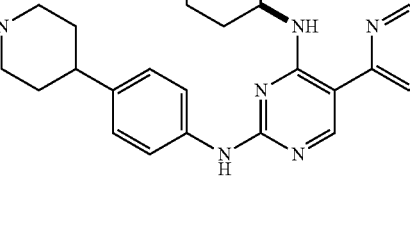 | UNC5128A | ++ | + | ++ | $^1$H NMR (CD$_3$OD, 400 MHz): δ 8.66 (d, J = 4.0 Hz, 1H), 8.42 (s, 1H), 8.00 (t, J = 8.0 Hz, 1H), 7.96 (d, J = 8.0 Hz, 1H), 7.61 (d J = 8.0 Hz, 2H), 7.48 (t, J = 8.0 Hz, 1H), 7.41 (d, J = 8.0 Hz, 2H), 4.08-4.05 (m, 1H), 3.71-3.66 (m, 1H), 3.47-3.44 (m, 2H), 3.17-3.06 (m, 3H), 2.16-2.01 (m, 6H), 193-1.64 (m, 2H), 1.58-1.50 (m, 2H), 1.44-1.34 (m, 2H); MS m/z 445.30 [M + H]$^+$. |
| 9 | 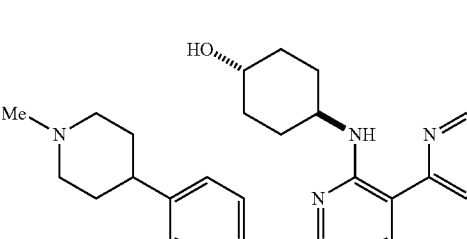 | UNC5130A | +++ | ++ | ++ | $^1$H NMR (CD$_3$OD, 400 MHz): δ 8.70 (d, J = 4.0 Hz, 1H), 8.37 (s, 1H), 8.10 (t, J = 8.0 Hz, 1H), 8.00 (d, J = 8.0 Hz, 1H), 7.59-7.54 (m, 3H), 7.39 (d, J = 8.0 Hz, 1H), 4.06-4.00 (m, 1H), 3.68-3.63 (m, 3H), 3.22-3.166 (m, 2H), 2.93 (s, 3H), 2.18-2.12 (m, 4H), 2.07-2.00 (m, 4H), 1.56-1.48 (m, 2H), 1.42-1.33 (m, 2H); MS m/z 459.30 [M + H]$^+$. |
| 10 | 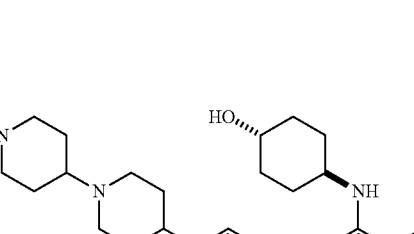 | UNC5072A | +++ | ++ | ++ | $^1$H NMR (CD$_3$OD, 400 MHz): δ 8.65 (d, J = 8.0 Hz, 1H), 8.42 (s, 1H), 8.02-7.94 (m, 2H), 7.58 (d, J = 8.0 Hz, 2H), 7.46 (t, J = 8.0 Hz, 1H), 7.41 (d, J = 8.0 Hz, 2H), 4.07-4.04 (m, 2H), 3.75-3.66 (m, 5H), 3.24-3.17 (m, 2H), 3.03-2.99 (m, 2H), 2.93 (s, 3H), 2.54-2.50 (m, 2H), 2.21-2.14 (m, 8H), |

TABLE 2-continued describes compounds could be prepared following procedures described in Example 2, using appropriate reagents.

| Structure | Compound_ID | Mer IC$_{50}$ | Axl IC$_{50}$ | Tyro3 IC$_{50}$ | Physical Data MS m/z (M + 1) or/and $^1$H NMR |
|---|---|---|---|---|---|
| 11 | UNC5052A | +++ | ++ | ++ | 2.04-2.01 (m, 2H), 1.58-1.49 (m, 2H), 1.44-1.38 (m, 2H); MS m/z 542.40 [M + H]$^+$.<br><br>$^1$H NMR (CD$_3$OD, 400 MHz): δ 9.08 (d, J = 8.0 Hz, 1H), 8.05 (d, J = 8.0 Hz, 1H), 8.53 (t, J = 8.0 Hz, 1H), 8.45 (s, 1H), 8.18 (d, J = 8.0 Hz, 1H), 8.02-7.99 (m, 2H), 7.68-7.59 (m, 2H), 7.50-7.47 (m, 1H), 6.23 (s, 1H), 5.17-5.11 (m, 1H), 4.20-4.07 (m, 1H), 4.07 (m, 2H), 3.80-3.67 (m, 3H), 3.44-3.41 (m, 2H), 3.23-3.20 (m, 1H), 3.03-2.99 (m, 1H), 2.93 (s, 3H), 2.66-2.56 (m, 3H), 2.25-2.15 (m, 3H), 2.08-1.98 (m, 2H), 1.62-1.40 (m, 4H); MS m/z 540.3 [M + H]$^+$. |
| 12 | UNC5113A | +++ | ++ | ++ | $^1$H NMR (CD$_3$OD, 400 MHz): δ 8.64 (d, J = 4.0 Hz, 1H), 8.45 (s, 1H), 7.95 (m, 2H), 7.66 (d, J = 8.0 Hz, 2H), 7.52 (d, J = 8.0 Hz, 2H), 7.45-7.42 (m, 1H), 6.43-6.41 (m, 1H), 4.612 (m, 2H), 4.08-4.06 (m, 2H), 3.73-3.67 (m, 1H), 3.40 (t, J = 8.0 Hz, 2H), 2.64-2.62 (m, 2H), 2.17 (d, J = 8.0 Hz, 2H), 2.04 (d, J = 8.0 Hz, 2H), 1.61-1.51 (m, 2H), 1.47-1.38 (m, 2H); MS m/z 443.30 [M + H]$^+$. |
| 13 | UNC5070A | ++ | + | ++ | $^1$H NMR (CD$_3$OD, 400 MHz): δ 8.63 (d, J = 4.0 Hz, 1H), 8.46 (s, 1H), 7.96 (m, 2H), 7.67 (d, J = 8.0 Hz, 2H), 7.53 (d, J = 8.0 Hz, 2H), 7.45-7.42 (m, 1H), 6.42 (s, 1H), 4.19 (d, J = 16.0 Hz, 1H), 4.10-4.05 (m, 1H), 3.96-3.87 (m, 2H), 3.72-3.67 (m, 1H), 3.61-3.59 (m, 1H), 3.13-3.06 (m, 1H), 2.71-2.67 (m, 2H), 2.47-2.31 (m, 3H), 2.17 (d, J = 8.0 Hz, 2H), 2.08-2.02 (m, 2H), 1.98-1.90 (m, 2H), 1.61-1.51 (m, 2H), 1.47-1.38 (m, 2H); MS m/z 497.30 [M + H]$^+$. |

TABLE 2-continued describes compounds could be prepared following procedures described in Example 2, using appropriate reagents.

| Structure | Compound_ID | Mer IC$_{50}$ | Axl IC$_{50}$ | Tyro3 IC$_{50}$ | Physical Data MS m/z (M + 1) or/and $^1$H NMR |
|---|---|---|---|---|---|
| 14 | UNC5129A | ++ | ++ | ++ | $^1$H NMR (CD$_3$OD, 400 MHz): δ 8.69 (d, J = 4.0 Hz, 1H), 8.38 (s, 1H), 8.08 (td, J$_1$ = 8.0 Hz, J$_2$ = 2.0 Hz, 1H), 7.99 (d, J= 8.0 Hz, 1H), 7.57 (d, J = 8.0 Hz, 2H), 7.54 (td, J$_1$ = 8.0 Hz, J$_2$ = 2.0 Hz, 1H), 7.39 (d, J = 8.0 Hz, 2H), 4.07-4.02 (m, 1H), 3.69-3.62 (m, 1H), 3.52-3.51 (m, 2H), 3.20-3.14 (m, 2H), 3.01-2.96 (m, 1H), 2.85 (s, 3H), 2.14-2.11 (m, 4H), 2.03-1.90 (m, 4H), 1.57-1.47 (m, 2H), 1.43-1.34 (m, 2H); MS m/z 445.30 [M + H]$^+$. |
| 15 | UNC5131A | +++ | ++ | ++ | $^1$H NMR (CD$_3$OD, 400 MHz): δ 8.69 (d, J = 4.0 Hz, 1H), 8.40 (s, 1H), 8.07 (t, J = 8.0 Hz, 1H), 7.99 (d, J = 8.0 Hz, 1H), 7.61 (d, J = 8.0 Hz, 2H), 7.54 (t, J = 4.0 Hz, 1H), 7.42 (d, J = 8.0 Hz, 2H), 4.07-4.02 (m, 1H), 3.69-3.64 (m, 1H), 3.60-3.57 (m, 2H), 3.18-3.04 (m, 3H), 2.93 (s, 3H), 2.15-1.95 (m, 7H ), 1.86-1.75 (m, 1H), 1.57-1.49 (m, 2H), 1.43-1.34 (m, 2H); MS m/z 459.35 [M + H]$^+$. |
| 16 | UNC5133A | ++ | + | ++ | $^1$H NMR (CD$_3$OD, 400 MHz): δ 8.66 (d, J = 4.0 Hz, 1H), 8.38 (s, 1H), 8.00 (td, J$_1$ = 8.0 Hz, J$_2$ = 2.0 Hz, 1H), 7.95 (d, J = 8.0 Hz, 1H), 7.58 (d, J = 8.0 Hz, 2H), 7.47 (t, J = 8.0 Hz, 1H), 7.38 (d, J = 8.0 Hz, 2H), 4.02-3.99 (m, 1H), 3.66-3.62 (m, 2H), 3.22-3.16 (m, 2H), 3.00-2.97 (m, 1H), 2.93 (s, 3H), 2.14 (m, 3H), 2.06-1.97 (m, 3H), 1.86-1.82 (m, 2H), 1.57-1.43 (m, 3H), 1.12-1.03 (m, 2H), 0.96 (d, J = 8.0 Hz, 3H); MS m/z 457.40 [M + H]$^+$. |

TABLE 2-continued describes compounds could be prepared following procedures described in Example 2, using appropriate reagents.

| | Structure | Compound_ID | Mer IC$_{50}$ | Axl IC$_{50}$ | Tyro3 IC$_{50}$ | Physical Data MS m/z (M + 1) or/and $^1$H NMR |
|---|---|---|---|---|---|---|
| 17 | 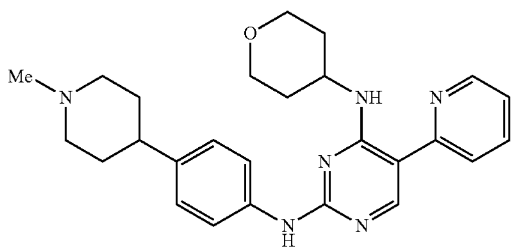 [SMILES: CN1CCC(c2ccc(Nc3ncc(-c4ccccn4)c(NC4CCOCC4)n3)cc2)CC1] | UNC5134A | ++ | + | ++ | $^1$H NMR (CD$_3$OD, 400 MHz): δ 8.67 (d, J = 4.0 Hz, 1H), 8.43 (s, 1H), 8.02-7.95 (m, 2H), 7.56 (d, J = 8.0 Hz, 2H), 7.48-7.45 (m, 1H), 7.39 (d, J = 8.0 Hz, 2H), 4.35-4.30 (m, 1H), 4.02-3.97 (m, 2H), 3.66-3.63 (m, 2H), 3.57-3.51 (m, 2H), 3.22-3.13 (m, 2H), 3.01-2.96 (m, 1H), 2.94 (s, 3H), 2.18-2.15 (m, 2H), 2.07-1.99 (m, 4H), 1.80-1.70 (m, 2H); MS m/z 445.30 [M + H]$^+$. |
| 18 | 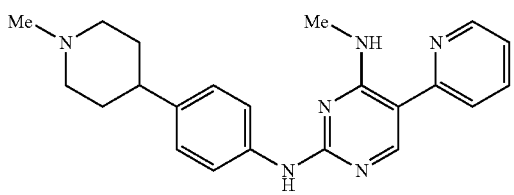 [SMILES: CNc1nc(Nc2ccc(C3CCN(C)CC3)cc2)ncc1-c1ccccn1] | UNC5136A | + | + | + | $^1$H NMR (CD$_3$OD, 400 MHz): δ 8.71 (d, J = 4.0 Hz, 1H), 8.32 (s, 1H), 8.10 (td, J$_1$ = 8.0 Hz, J$_2$ = 2.0 Hz, 2H), 7.97 (d, J = 8.0 Hz, 1H), 7.61 (d, J = 8.0 Hz, 2H), 7.58-7.54 (m, 1H), 7.40 (d, J = 8.0 Hz, 2H), 3.66-3.62 (m, 2H), 3.21-3.16 (m, 2H), 3.18 (s, 3H), 2.98-2.95 (m, 1H), 2.93 (s, 3H), 2.17-2.14 (m, 2H), 2.08-2.01 (m, 2H); MS m/z 375.30 [M + H]$^+$. |
| 19 | 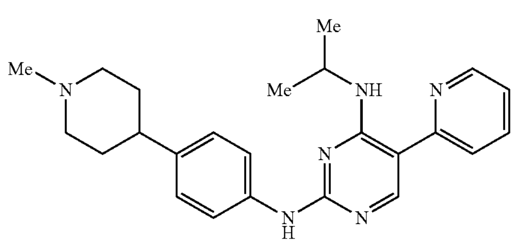 [SMILES: CC(C)Nc1nc(Nc2ccc(C3CCN(C)CC3)cc2)ncc1-c1ccccn1] | UNC5135A | +++ | ++ | ++ | $^1$H NMR (CD$_3$OD, 400 MHz): ) δ 8.75 (d, J = 4.0 Hz, 1H), 8.32 (s, 1H), 8.17 (td, J$_1$ = 8.0 Hz, J$_2$ = 2.0 Hz, 1H), 8.02 (d, J = 8.0 Hz, 1H), 7.63 (dd, J$_1$ = 8.0 Hz, J$_2$ = 4.0 Hz, 1H), 7.57 (d, J = 8.0 Hz, 2H), 7.40 (d, J = 8.0 Hz, 2H), 4.47-4.41 (m, 1H), 3.66-3.62 (m, 2H), 3.22-3.16 (m, 2H), 3.03-2.95 (m, 1H), 2.93 (s, 3H), 2.17-2.08 (m, 2H), 2.04-1.98 (m, 2H); MS m/z 403.30 [M + H]$^+$. |

Example 3

N-(5-((4-((4-(((trans-4-Hydroxycyclohexyl)amino)-5-(pyridin-2-yl)pyrimidin-2-yl)amino)phenyl)ethynyl)pyrazin-2-yl)isobutyramide General Procedure C:

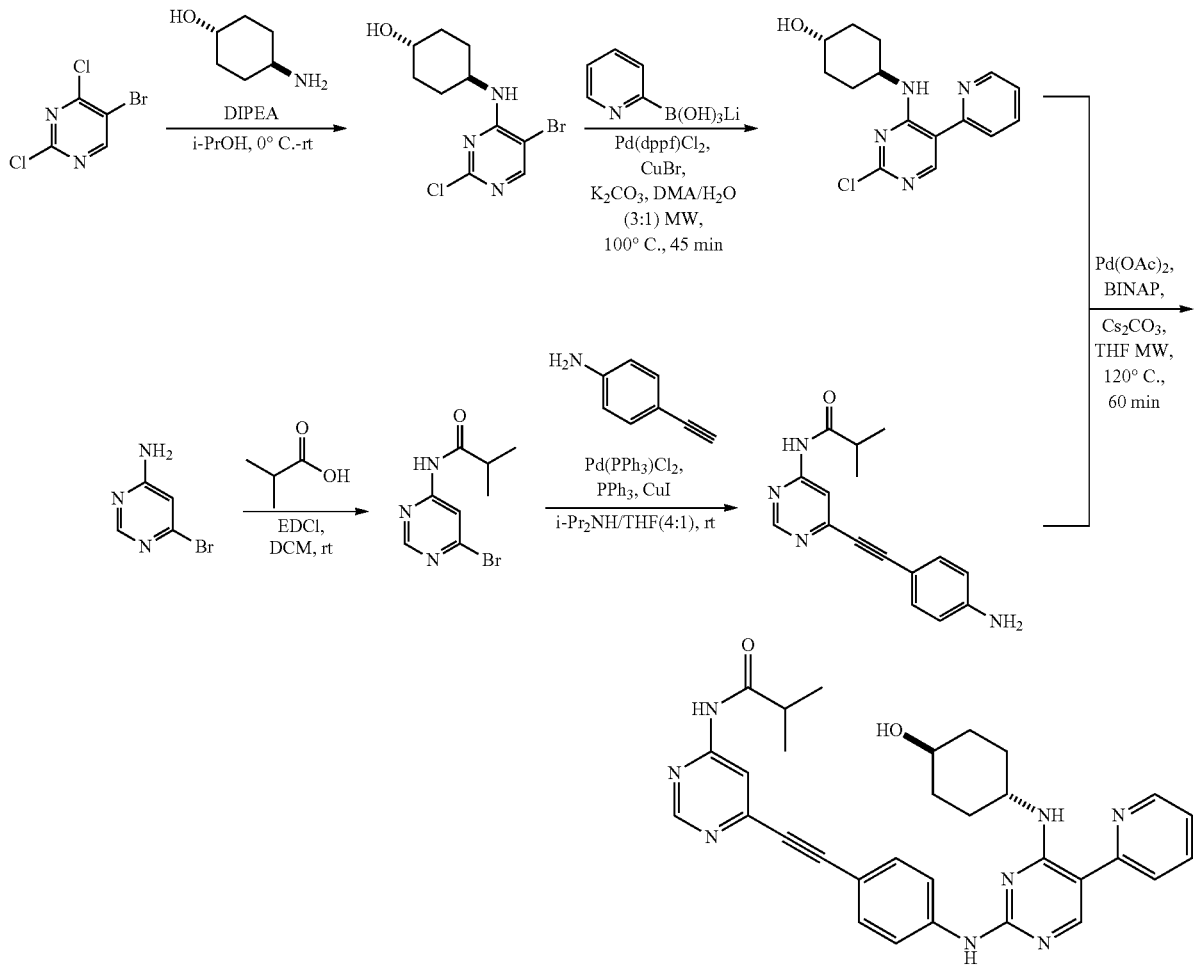

trans-4-((2-Chloro-5-(pyridin-2-yl)pyrimidin-4-yl)amino)cyclohexan-1-ol

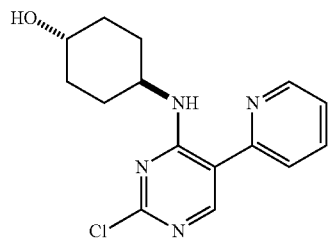

To a solution of 5-bromo-2,4-dichloropyrimidine (114 g, 500 mol) in $^i$PrOH was added DIPEA (91.5 mL, 525 mmol) slowly at 0° C. in ice-water bath, followed by adding trans-4-aminocyclohexan-1-ol (66.5 g, 500 mmol) in $^i$PrOH dropwise at 0° C. The reaction mixture was warmed to rt overnight, and then the solution was washed with brine (200 mL×2), dried (Na$_2$SO$_4$) and concentrated under reduced pressure. The crude product was recrystallized in a solution of EtOAc/Hexane to provide pure trans-4-((5-bromo-2-chloropyrimidin-4-yl)amino)cyclohexan-1-ol (142 g, 93% yield). NMR (CD$_3$OD, 400 MHz): 8.09 (s, 1H), 4.02-3.96 (m, 1H), 3.59-3.52 (m, 1H), 2.00-1.93 (m, 3H), 1.53-1.33 (m, 5H). To a solution of trans-4-((5-bromo-2-chloropyrimidin-4-yl)amino)cyclohexan-1-ol (3.06 g, 10.0 mmol) in DMA (40 mL) was added a solution of K$_2$CO$_3$ (4.14 g, 30.0 mmol) in H$_2$O (10.0 mL) in the open air at room temperature. After stirring for about 3 minutes, 2-bronic acids pyridine lithium salt (4.5 g, 30.0 mmol) was added in one portion. The reaction mixture was stirred for 20 min, then was added Pd(dppf)Cl$_2$ (816 mg, 1.00 mmol) and CuBr (284 mg, 2.00 mmol) in one portion. Then the reaction mixture was heated at 100° C. for 45 min. After filtration and concentration, the crude product (black solid) was purified by column chromatography with ISCO system to afford the title compound as a light yellow solid (821 mg, 27%). NMR (CD₃OD, 400 MHz): 8.59 (d, J=8.0 Hz, 1H), 8.53 (s, 1H), 7.95 (d, J=8.0 Hz, 1H), 7.88 (t, J=8.0 Hz, 1H), 7.34 (dd, J₁=8.0 Hz, J₂=2.0 Hz, 1H), 4.07-3.99 (m, 1H), 3.66-3.59 (m, 1H), 2.13-2.09 (m, 2H), 1.99-1.97 (m, 2H), 1.50-1.36 (m, 4H).

N-(5-((4-((4-(((trans-4-Hydroxycyclohexyl)amino)-5-(pyridin-2-yl)pyrimidin-2-yl)amino)phenyl)ethynyl)pyrazin-2-yl)isobutyramide

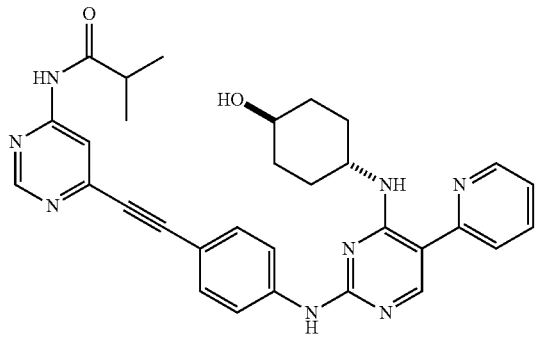

To a solution of 6-bromopyrimidin-4-amine (645 mg, 5.0 mmol) in DCM was added EDCI (1.15 g, 6.0 mmol) and isobutyric acid (440 mg, 6.0 mmol) respectively at room temperature. The reaction mixture was stirred at room temperature overnight. The solvent was removed under reduced pressure and the crude product was purified by column chromatography with ISCO system to afford the desired compound N-(6-bromopyrimidin-4-yl)isobutyramide as a white solid (680 mg, 68%). NMR (CD₃OD, 400 MHz): 8.60 (d, J=2.0 Hz, 1H), 2.69 (q, J=8.0 H, 1H), 1.17 (d, J=8.0 Hz, 6H).

To a mixture of N-(6-bromopyrimidin-4-yl)isobutyramide (600 mg, 3.0 mmol), 4-ethynylaniline (421 mg, 3.6 mmol), Pd(PPh₃)Cl₂ (105 mg, 0.15 mmol, 5 mol %), PPh₃ (78.6 mg, 0.30 mmol, 10 mol %) and CuI (57.3 mg, 0.30 mmol, 10 mol %) in THF (2.0 mL) was added ⁱPr₂NH (18.0 mL) under nitrogen. The reaction mixture was stirred at 50° C. overnight. The solvent was removed under reduced pressure and the crude product was purified by column chromatography with ISCO system to afford the desired compound N-(6-((4-aminophenyl)ethynyl)pyrimidin-4-yl)isobutyramide as a light yellow solid (500 mg, 60%). (CD₃OD, 400 MHz): 8.68 (d, J=4.0 Hz, 1H), 8.38 (d, J=4.0 Hz, 1H), 7.32 (d, J=8.0 Hz, 2H), 7.17 (d, J=4.0 Hz, 1H), 6.64 (d, J=8.0 Hz, 2H), 6.59 (d, J=4.0 Hz, 2H), 2.71 (q, J=8.0 H, 1H), 1.18 (d, f=8.0 Hz, 6H).

To a mixture of N-(6-((4-aminophenyl)ethynyl)pyrimidin-4-yl)isobutyramide (0.24 mmol, 1.2 equivalent), trans-4-((2-chloro-5-(pyridin-2-yl)pyrimidin-4-yl)amino)cyclohexan-141 (60.8 mg, 0.20 mmol, 1.0 equivalent), Pd(OAc)₂ (9.0 mg, 0.02 mmol, 10 mol %), BINAP (25 mg, 0.04 mmol, 20 ml %) and Cs₂CO₃ (157 mg, 0.48 mmol, 2.4 equivalent) in THF (2.0 mL) was heated at 120° C. under microwave irradiation for 1.0 h. The solvent was removed under reduced pressure and the crude product was purified by column chromatography with ISCO system to afford the titled compound as a yellow solid (8.0 mg, 7%). (UNC4293A)¹H NMR (CD₃OD+DMSO-D₆, 400 MHz): 9.42 (d, J=4.0 Hz, 1H), 8.68 (d, J=4.0 Hz, 1H), 8.57 (s, 1H), 8.54 (s, 1H), 8.00 (m, 1H), 7.72 (d, J=8.0 Hz, 2H), 7.70 (d, J=8.0 Hz, 2H), 7.49-7.45 (m, 1H), 4.15-4.10 (m, 1H), 3.70-3.58 (m, 2H), 2.78 (q, J=8.0 H, 1H), 2.20-2.15 (m, 2H), 2.09-2.06 (m, 2H), 1.23 (d, J=8.0 Hz, 6H). MS m/z 549.30 [M+H]⁺.

TABLE 3 describes compounds could be prepared following procedures described in Example 3, using appropriate reagents.

| | Structure | Compound_ID | Mer IC₅₀ | Axl IC₅₀ | Tyro3 IC₅₀ | Physical Data MS m/z (M + 1) or/and ¹H NMR |
|---|---|---|---|---|---|---|
| 1 | (structure) | UNC4293A | ++ | ++ | ++ | ¹H NMR (CD₃OD + DMSO-D₆, 400 MHz): 9.42 (d, J = 4.0 Hz, 1H), 8.68 (d, J = 4.0 Hz, 1H), 8.57 (s, 1H), 8.54 (s, 1H), 8.00 (m, 1H), 7.72 (d, J = 8.0 Hz, 2H), 7.70 (d, J = 8.0 Hz, 2H), 7.49-7.45 (m, 1H), 4.15-4.10 (m, 1H), 3.70-3.58 (m, 2H), 2.78 (q, J = 8.0 H, 1H), 2.20-2.15 (m, 2H), 2.09-2.06 (m, 2H), 1.23 (d, J = 8.0 Hz, 6H);. MS m/z 549.30 [M + H]⁺. |
| 2 | (structure) | UNC4329A | +++ | ++ | ++ | ¹H NMR (CD₃OD + DMSO-D₆, 400 MHz): 8.65 (d, J = 8.0 Hz, 1H), 8.61 (d, J = 8.0 Hz, 1H), 8.54 (s, 1H), 8.27 (d, J = 4.0 Hz, 1H), 7.99-7.98 (m, 2H), 7.83 (d, J = 8.0 Hz, 2H), 7.78 (d, J = 8.0 Hz, 2H), 7.47-7.43 (m, 2H), 4.60 (dd, J₁ = 8.0 Hz, J₂ = 4.0 Hz, 1H), 4.15-4.10 (m, 2H), 3.74-3.55 (m, 3H), 3.53-3.40 (m, 3H), 2.67-2.58 (m, 1H), 2.24-2.06 (m, 6H), 1.63-1.52 (m, 5H); MS m/z 576.20 [M + H]⁺. |

TABLE 3-continued describes compounds could be prepared following procedures described in Example 3, using appropriate reagents.

| Structure | Compound_ ID | Mer IC$_{50}$ | Axl IC$_{50}$ | Tyro3 IC$_{50}$ | Physical Data MS m/z (M + 1) or/and $^1$H NMR |
|---|---|---|---|---|---|
| 3 | UNC4325A | +++ | +++ | +++ | $^1$H NMR (CD$_3$OD, 400 MHz): 8.84-8.81(br, 1H), 8.65 (d, J = 4.0 Hz, 1H), 8.50 (s, 1H), 7.99 (m, 3H), 7.78 (m, 4H), 7.47 (m, 2H), 4.16-4.13 (m, 2H), 3.74 (t, J = 8.0 Hz, 1H), 3.70-3.55 (m, 2H), 3.58 (t, J = 8.0 Hz, 1H), 2.23-2.18 (m, 2H), 2.09-2.04 (m, 2H), 1.63-1.42 (m, 8H), 1.26 (d, J = 8.0 Hz, 3H), 0.97 (t, J = 8.0 Hz, 3H); MS m/z 576.30 [M + H]$^+$. |
| 4 | UNC3228A | ++ | + | ++ | $^1$H NMR (400 MHz, CD$_3$OD) δ 8.67 (dd, J$_1$ = 2.0 Hz, J$_2$ = 8.0 Hz, 1H), 8.43 (s, 1H), 8.05-8.01 (m, 1H), 7.99-7.95 (m, 2H), 7.79 (dd, J$_1$ = 2.0 Hz, J$_2$ = 8.0 Hz, 1H), 7.70-7.64 (m, 2H), 7.63-7.60 (m, 2H), 7.52-7.45 (m, 3H), 4.13-4.06 (m, 1H), 3.75-3.61 (m, 1H), 3.89-2.83 (m, 1H), 2.19 (d, J = 8.0 Hz, 2H), 2.06 (d, J = 8.0 Hz, 2H), 1.62-1.39 (m, 4H), 1.15 (d, J = 2.0 Hz, 1H), 0.84-0.79 (m, 2H), 0.67-0.64 (m, 2H), MS m/z 545.3 [M + H]$^+$. |
| 5 | UNC3259A | ++++ | ++++ | +++ | $^1$H NMR (400 MHz, CD$_3$OD) δ 8.79 (d, J = 2.0 Hz, 1H), 7.79 (dt, J$_1$ = 2.0 Hz, J$_2$ = 8.0 Hz, 1H), 8.49 (s, 1H), 8.22 (dd, J$_1$ = 1.0 Hz, J$_2$ = 4.0 Hz, 1H), 8.00-7.96 (m, 3H), 7.80-7.74 (m, 4H), 7.48-7.45 (m, 1H), 4.15-4.09 (m, 1H), 3.72-3.64 (m, 1H), 2.96-2.90 (m, 1H), 2.19 (dd, J$_1$ = 1.0 Hz, J$_2$ = 4.0 Hz, 2H), 2.06 (dd, J$_1$ = 1.0 Hz, J$_2$ = 4.0 Hz, 2H), 1.63-1.53 (m, 2H), 1.50-1.41 (m, 2H), 0.89-0.84 (m, 2H), 0.72-0.69 (m, 2H), MS m/z 546.3 [M + H]$^+$. |
| 6 | UNC3229A | +++ | +++ | +++ | $^1$H NMR (400 MHz, CD$_3$OD) δ 8.64 (d, J = 4.0 Hz, 1H), 8.46 (s, 1H), 8.28 (s, 1H), 8.00-7.93 (m, 2H), 7.79 (dt, J = 2.0 Hz, J$_2$ = 8.0 Hz, 1H), 8.49 (s, 1H), 7.75 (d, J = 8.0 Hz, 2H), 7.70 (d, J = 8.0 Hz, 2H), 7.47-7.42 (m, 1H), 4.16-4.07 (m, 1H), 3.75-3.56 (m, 1H), 2.87-2.80 (m, 1H), 2.20 (d, J = 12.0 Hz, 2H), 2.06 (d, J = 12.0 Hz, 2H), 1.63-1.38 (m, 4H), 0.85-0.78 (m, 2H), 0.68-0.62 (m, 2H), MS m/z 552.2 [M + H]$^+$. |

TABLE 3-continued describes compounds could be prepared following procedures described in Example 3, using appropriate reagents.

| Structure | Compound_ID | Mer IC$_{50}$ | Axl IC$_{50}$ | Tyro3 IC$_{50}$ | Physical Data MS m/z (M + 1) or/and $^1$H NMR |
|---|---|---|---|---|---|
| 7 | UNC3293A | +++ | +++ | +++ | $^1$H NMR (400 MHz, CD$_3$OD) δ 8.79 (d, J = 4.0 Hz, 1H), 8.20 (dd, J$_1$ = 1.0 Hz, J$_2$ = 2.0 Hz, 1H), 7.96 (dd, J$_1$ = 1.0 Hz, J$_2$ = 4.0 Hz, 1H), 7.77 (s, 1H), 7.76 (s, 4H), 7.68 (s, 1H), 7.56 (s, 1H), 7.54 (s, 1H), 4.49 (s, 2H), 4.15-4.08 (m, 1H), 3.81-3.53 (m, 9H), 3.01 (s, 3H), 2.95-2.90 (m, 1H), 2.06-1.95 (m, 4H), 1.58-1.46 (m, 2H), 1.42-1.32 (m, 2H), 1.87-1.85 (m, 2H), 0.71-0.69 (m, 2H), MS m/z 657.4 [M + H]$^+$. |
| 8 | UNC3319A | ++++ | ++++ | ++++ | $^1$H NMR (400 MHz, D$_2$O) δ 8.10-8.04 (m, 1H), 8.02-7.96 (m, 1H), 7.94 (s, 1H), 7.53 (d, J = 8.0 Hz, 1H), 7.31 (d, J = 8.0 Hz, 1H), 7.26-7.15 (m, 3H), 7.05-6.95 (s, 2H), 6.90 (s, 1H), 3.85-3.75 (m, 1H), 3.68 (s, 2H), 3.63-3.59 (m, 1H), 3.58-3.51 (m, 2H), 3.44-3.06 (m, 6H), 2.80 (s, 3H), 2.59-2.50 (m, 1H), 2.18-1.99 (m, 4H), 1.60-1.49 (m, 2H), 1.45-1.32 (m, 2H), 0.77-0.70 (m, 2H), 0.47-0.41 (m, 2H), MS m/z 658.0 [M + H]$^+$. |
| 9 | UNC3320A | ++ | + | ++ | $^1$H NMR (400 MHz, D$_2$O) δ 8.56 (d, J = 2.0 Hz, 1H), 7.90 (dd, J$_1$ = 1.0 Hz, J$_2$ = 8.0 Hz, 1H), 7.45-7.25 (m, 10H), 4.25 (s, 2H), 3.73-3.40 (m, 9H), 2.90 (s, 3H), 2.56-2.49 (m, 1H), 2.00-1.87 (m, 4H), 1.38-1.22 (m, 4H), 0.70-0.63 (m, 2H), 0.40-0.34 (m, 2H), MS m/z 657.0 [M + H]$^+$. |
| 10 | UNC3321A | ++ | + | ++ | $^1$H NMR (400 MHz, D$_2$O) δ 7.81-7.73 (m, 3H), 7.51-7.46 (m, 3H), 7.44-7.38 (m, 2H), 7.33 (d, J = 2.0 Hz, 2H), 7.24 (d, J = 2.0 Hz, 2H), 3.97 (s, 2H), 3.74-3.64 (m, 1H), 3.63-3.52 (m, 1H), 3.48-3.27 (m, 4H), 3.24-3.06 (m, 4H), 2.71-2.65 (m, 1H), 1.99-1.86 (m, 4H), 1.33-1.19 (m, 4H), 0.80-0.73 (m, 2H), 0.56-0.51 (m, 2H), MS m/z 657.0 [M + H]$^+$. |
| 11 | UNC3328A | +++ | +++ | + | $^1$H NMR (400 MHz, CD$_3$OD) δ 8.76-8.74 (m, 1H), 8.27-8.25 (m, 1H), 8.07-8.03 (m, 1H), 7.88-7.83 (m, 2H), 7.80-7.73 (m, 2H), 7.72-7.65 (m, 2H), 7.57-7.51 (m, 2H), 7.36-7.33 (m, 1H), 3.78-3.69 (m, 4H), 3.37-3.65 (m, 1H), 3.08-3.00 (m, 4H), 2.94-2.87 (m, 1H), 2.06-1.95 (m, 4H), 1.43-1.30 (m, 4H), 0.87-0.80 (m, 2H), 0.73-0.65 (m, 2H), MS m/z 694.3 [M + H]$^+$. |

TABLE 3-continued describes compounds could be prepared following procedures described in Example 3, using appropriate reagents.

| | Structure | Compound_ID | Mer IC$_{50}$ | Axl IC$_{50}$ | Tyro3 IC$_{50}$ | Physical Data MS m/z (M + 1) or/and $^1$H NMR |
|---|---|---|---|---|---|---|
| 12 | 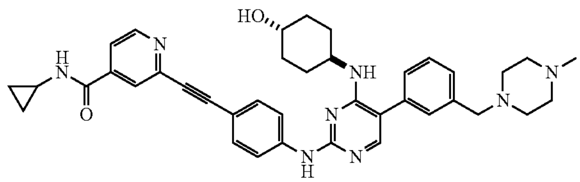 | UNC3322A | +++ | +++ | ++ | $^1$H NMR (400 MHz, D$_2$O) δ 8.47 (dd, J$_1$ = 2.0 Hz, J$_2$ = 8.0 Hz, 1H), 7.52-7.26 (m, 11H), 4.16 (s, 2H), 3.75-3.67 (m, 1H), 3.63-3.31 (m, 9H), 2.87 (s, 3H), 2.67-2.60 (m, 1H), 2.00-1.86 (m, 4H), 1.34-1.23 (m, 4H), 0.77-0.70 (m, 2H), 0.54-0.48 (m, 2H), MS m/z 657.4 [M + H]$^+$. |
| 13 | 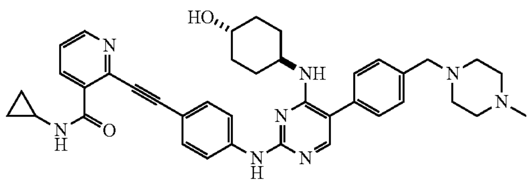 | UNC3323A | ++ | + | ++ | $^1$H NMR (400 MHz, D$_2$O) δ 8.52 (dd, J$_1$ = 2.0 Hz, J$_2$ = 8.0 Hz, 1H), 7.94 (dd, J$_1$ = 2.0 Hz, J$_2$ = 8.0 Hz, 1H), 7.47-7.23 (m, 9H), 6.92 (s, 1H), 4.33 (s, 2H), 3.72-3.36 (m, 10H), 2.91 (s, 3H), 2.66-2.61 (m, 1H), 1.92-1.83 (m, 2H), 1.82-1.73 (m, 2H), 1.29-1.03 (m, 4H), 0.43-0.34 (m, 3H), MS m/z 657.2 [M + H]$^+$. |
| 14 | 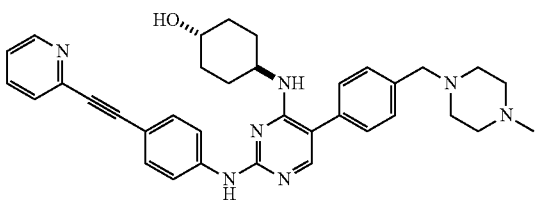 | UNC3324A | +++ | ++ | +++ | $^1$H NMR (400 MHz, D$_2$O) δ 8.55-8.52 (m, 1H), 8.27 (td, J$_1$ = 2.0 Hz, J$_2$ = 8.0 Hz, 1H), 7.88-7.84 (m, 1H), 7.75-7.70 (m, 1H), 7.66-7.57 (s, 4H), 7.51 (s, 1H), 7.47 (d, J = 2.0 Hz, 2H), 7.40 (d, J = 2.0 Hz, 2H), 4.24 (s, 2H), 3.90-3.80 (m, 1H), 3.56-3.28 (m, 10H), 2.88 (s, 3H), 1.89 (d, J = 8.0 Hz, 2H), 1.32-1.16 (m, 2H), MS m/z 574.3 [M + H]$^+$. |
| 15 | 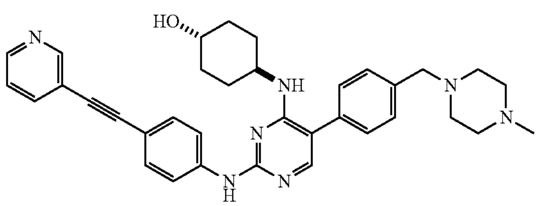 | UNC3325A | + | + | ++ | $^1$H NMR (400 MHz, D$_2$O) δ 8.75-8.73 (m, 1H), 8.59-8.56 (m, 1H), 8.27 (dt, J$_1$ = 2.0 Hz, J$_2$ = 8.0 Hz, 1H), 8.27 (ddd, J$_1$ = 1.0 Hz, J$_2$ = 2.0 Hz, J$_3$ = 8.0 Hz, 1H), 7.63-7.54 (m, 4H), 7.50 (s, 1H), 7.48 (d, J = 2.0 Hz, 2H), 7.41 (d, J = 2.0 Hz, 2H), 4.24 (s, 2H), 3.90-3.80 (m, 1H), 3.55-3.28 (m, 10H), 2.87 (s, 3H), 1.88 (d, J = 8.0 Hz, 2H), 1.30-1.19 (m, 2H), MS m/z 574.3 [M + H]$^+$. |
| 16 | 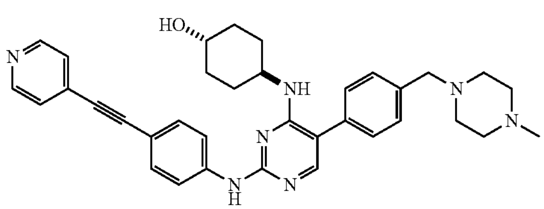 | UNC3326A | ++ | + | + | $^1$H NMR (400 MHz, D$_2$O) δ 8.60 (d, J = 8.0 Hz, 2H), 7.95 (d, J = 8.0 Hz, 2H), 7.68 (d, J = 8.0 Hz, 2H), 7.61 (d, J = 8.0 Hz, 2H), 7.52 (s, 1H), 7.49 (d, J = 8.0 Hz, 2H), 7.41 (d, J = 8.0 Hz, 2H), 4.23 (s, 2H), 3.93-3.83 (m, 1H), 3.57-3.22 (m, 10H), 2.86 (s, 3H), 1.88(d, J = 8.0 Hz, 2H), 1.32-1.15 (m, 2H), MS m/z 574.3 [M + H]$^+$. |
| 17 | 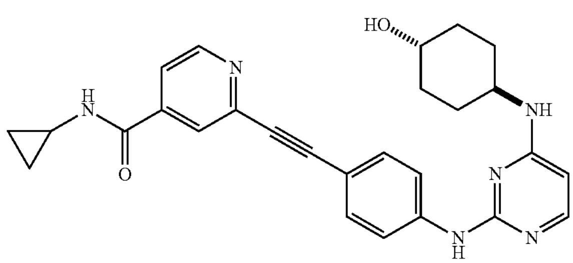 | UNC3327A | ++ | ++ | ++ | $^1$H NMR (400 MHz, CD$_3$OD) δ 8.82 (d, J = 8.0 Hz, 2H), 8.30 (dd, J$_1$ = 1.0 Hz, J$_2$ = 2.0 Hz, 1H), 8.06 (dd, J$_1$ = 2.0 Hz, J$_2$ = 8.0 Hz, 1H), 7.73 (s, 4H), 7.67 (d, J = 8.0 Hz, 2H), 6.62 (d, J = 4.0 Hz, 2H), 3.94-3.86 (m, 1H), 3.66-3.60 (m, 1H), 2.95-2.89 (m, 1H), 2.11-2.96 (m, 4H), 1.47-1.30 (m, 4H), 0.88-0.81 (m, 2H), 0.72-0.65 (m, 2H), MS m/z 469.2 [M + H]$^+$. |

TABLE 3-continued describes compounds could be prepared following procedures described in Example 3, using appropriate reagents.

| | Structure | Compound_ID | Mer IC$_{50}$ | Axl IC$_{50}$ | Tyro3 IC$_{50}$ | Physical Data MS m/z (M + 1) or/and $^1$H NMR |
|---|---|---|---|---|---|---|
| 18 | 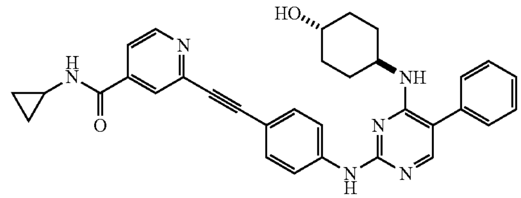 | UNC3374A | ++ | +++ | + | $^1$H NMR (400 MHz, D$_2$O) δ 8.66 (dd, J$_1$ = 1.0 Hz, J$_2$ = 2.0 Hz, 1H), 7.95 (dd, J$_1$ = 1.0 Hz, J$_2$ = 2.0 Hz, 1H), 7.71 (dd, J$_1$ = 1.0 Hz, J$_2$ = 2.0 Hz, 1H), 7.69 (s, 3H), 7.59 (s, 1H), 7.54-7.47 (m, 4H), 7.43-7.39 (m, 2H), 3.94-3.86 (m, 1H), 4.13-4.01 (m, 1H), 3.56-3.45 (m, 1H), 2.91-2.85 (m, 1H), 2.03-1.93 (m, 4H), 1.51-1.27 (m, 4H), 0.86-0.79 (m, 2H), 0.68-0.62 (m, 2H), MS m/z 545.3 [M + H]$^+$. |
| 19 | 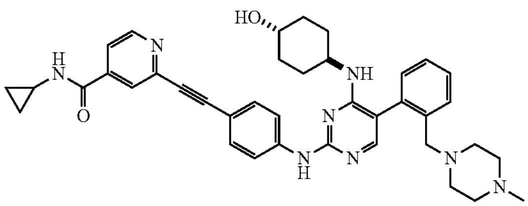 | UNC3393A | + | + | | $^1$H NMR (400 MHz, D$_2$O) δ 8.53 (dd, J$_1$ = 1.0 Hz, J$_2$ = 4.0 Hz, 1H), 7.70-7.68 (m, 1H), 7.60-7.36 (m, 9H), 7.23 (dd, J$_1$ = 1.0 Hz, J$_2$ = 8.0 Hz, 1H), 3.92-3.76 (m, 2H), 3.72-3.65 (m, 1H), 3.56-3.45 (m, 1H), 3.42-3.11 (m, 4H), 3.07-2.81 (m, 4H), 2.77 (s, 3H), 2.71-2.63 (m, 1H), 2.95-2.71 (m, 4H), 1.30-1.04 (m, 4H), 0.78-0.71 (m, 2H), 0.57-0.51 (m, 2H), MS m/z 657.3 [M + H]$^+$. |
| 20 | 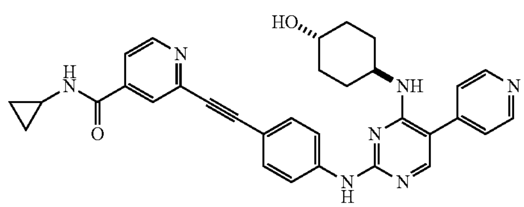 | UNC3395A | +++ | +++ | ++ | $^1$H NMR (400 MHz, D$_2$O) δ 8.59 (d, J = 8.0 Hz, 2H), 8.46 (dd, J$_1$ = 2.0 Hz, J$_2$ = 8.0 Hz, 1H), 7.88 (d, J = 8.0 Hz, 2H), 7.78 (s, 1H), 7.58-7.56 (m, 1H), 7.51 (dd, J$_1$ = 2.0 Hz, J$_2$ = 8.0 Hz, 1H), 7.47 (d, J = 8.0 Hz, 2H), 7.41 (d, J = 8.0 Hz, 2H), 3.77-3.67 (m, 1H), 3.63-3.52 (m, 1H), 2.65-2.58 (m, 1H), 2.00-1.88 (m, 4H), 1.39-1.19 (m, 4H), 0.77-0.68 (m, 2H), 0.54-0.48 (m, 2H), MS m/z 546.3 [M + H]$^+$. |
| 21 | 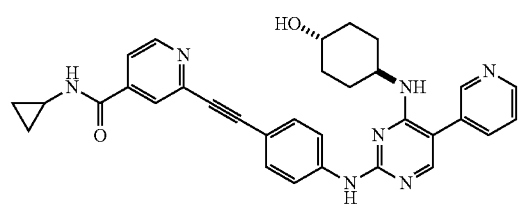 | UNC3396A | +++ | +++ | ++ | $^1$H NMR (400 MHz, D$_2$O) δ 8.74 (d, J = 1.0 Hz, 1H), 8.70 (d, J = 4.0 Hz, 1H), 8.53 (dd, J$_1$ = 2.0 Hz, J$_2$ = 8.0 Hz, 1H), 8.53 (dd, J$_1$ = 2.0 Hz, J$_2$ = 8.0 Hz, 1H), 8.45 (dt, J$_1$ = 4.0 Hz, J$_2$ = 8.0 Hz, 1H), 7.98 (dd, J$_1$ = 2.0 Hz, J$_2$ = 8.0 Hz, 1H), 7.73-7.71 (m, 1H), 7.66 (s, 1H), 7.63 (dd, J$_1$ = 2.0 Hz, J$_2$ = 8.0 Hz, 1H), 7.54-7.48 (m, 4H), 3.84-3.70 (m, 1H), 3.60-3.49 (m, 1H), 2.69-2.61 (m, 1H), 1.96-1.83 (m, 4H), 1.35-1.18 (m, 4H), 0.77-0.70 (m, 2H), 0.56-0.49 (m, 2H), MS m/z 547.2 [M + H]$^+$. |

TABLE 3-continued describes compounds could be prepared following procedures described in Example 3, using appropriate reagents.

| Structure | Compound_ ID | Mer IC$_{50}$ | Axl IC$_{50}$ | Tyro3 IC$_{50}$ | Physical Data MS m/z (M + 1) or/and $^1$H NMR |
|---|---|---|---|---|---|
| 22 | UNC3397A | +++ | ++++ | ++ | $^1$H NMR (400 MHz, D$_2$O) δ 8.36 (d, J = 4.0 Hz, 1H), 7.52-7.45 (m, 3H), 7.42-7.37 (m, 3H), 7.36-7.30 (m, 3H), 7.26 (d, J = 12.0 Hz, 2H), 3.81-3.67 (m, 2H), 3.66-3.57 (m, 2H), 3.52-3.44 (m, 2H), 3.18-3.05 (m, 2H), 2.76-2.65 (m, 2H), 2.64-2.57 (m, 1H), 2.00 (d, J = 8.0 Hz, 2H), 1.90 (d, J = 8.0 Hz, 2H), 1.43-1.19 (m, 4H), 0.76-0.65 (m, 2H), 0.55-0.49 (m, 2H), MS m/z 707.2 [M + H]$^+$. |
| 23 | UNC3398A | ++++ | ++++ | ++++ | $^1$H NMR (400 MHz, D$_2$O) δ 8.02 (d, J = 4.0 Hz, 1H), 8.67-8.63 (m, 2H), 8.28 (dd, J$_1$ = 4.0 Hz, J$_2$ = 8.0 Hz, 1H), 8.17 (d, J = 8.0 Hz, 1H), 7.95-7.93 (m, 1H), 7.74 (d, J = 8.0 Hz, 1H), 7.70 (dd, J$_1$ = 4.0 Hz, J$_2$ = 8.0 Hz, 1H), 7.65 (d, J = 8.0 Hz, 2H), 4.16-4.06 (m, 1H), 4.05-3.73 (m, 4H), 3.70-3.62 (m, 1H), 3.60-3.35 (m, 4H), 3.29 (s, 3H), 2.90-2.85 (m, 1H), 2.19 (d, J = 8.0 Hz, 2H), 2.06 (d, J = 8.0 Hz, 2H), 1.64-1.37 (m, 4H), 0.86-0.80 (m, 2H), 0.68-0.63 (m, 2H), MS m/z 708.3 [M + H]$^+$. |
| 24 | UNC3399A | ++++ | ++++ | +++ | $^1$H NMR (400 MHz, D$_2$O) δ 8.94-8.91 (m, 1H), 8.70 (s, 1H), 8.66 (d, J = 8.0 Hz, 1H), 8.24-8.14 (m, 2H), 8.04 (s, 1H), 4.14-4.06 (m, 1H), 3.79-3.72 (m, 4H), 3.70-3.62 (m, 1H), 3.14-3.04 (m, 4H), 2.92-2.85 (m, 1H), 2.21 (d, J = 8.0 Hz, 2H), 2.08 (d, J = 8.0 Hz, 2H), 1.64-1.41 (m, 4H), 0.88-0.78 (m, 2H), 0.70-0.63 (m, 2H), MS m/z 695.3 [M + H]$^+$. |
| 25 | UNC3437A | +++ | ++ | +++ | $^1$H NMR (400 MHz, CD$_3$OD) δ 8.77 (dd, J$_1$ = 2.0 Hz, J$_2$ = 8.0 Hz, 1H), 8.13-8.12 (m, 1H), 7.92 (dd, J$_1$ = 2.0 Hz, J$_2$ = 8.0 Hz, 1H), 7.81-7.78 (m, 4H), 7.75 (d, J = 8.0 Hz, 1H), 7.69 (s, 1H), 7.54 (d, J = 8.0 Hz, 2H), 6.00 (s, 1H), 4.42 (s, 2H), 4.11 (s, 4H), 3.81-3.47 (m, 10H), 3.00 (s, 3H), 2.06-1.96 (m, 4H), 1.58-1.45 (m, 2H), 1.43-1.27 (m, 2H), MS m/z 646.0 [M + H]$^+$. |

TABLE 3-continued describes compounds could be prepared following procedures described in Example 3, using appropriate reagents.

| Structure | Compound_ID | Mer IC$_{50}$ | Axl IC$_{50}$ | Tyro3 IC$_{50}$ | Physical Data MS m/z (M + 1) or/and $^1$H NMR |
|---|---|---|---|---|---|
| 26 | UNC3438A | +++ | ++ | +++ | $^1$H NMR (400 MHz, CD$_3$OD) δ 8.66 (dd, J$_1$ = 2.0 Hz, J$_2$ = 8.0 Hz, 1H), 7.80-7.77 (m, 1H), 7.76-7.71 (m, 2H), 7.71-7.66 (m, 2H), 7.64 (d, J = 8.0 Hz, 1H), 7.57 (dd, J$_1$ = 2.0 Hz, J$_2$ = 8.0 Hz, 2H), 7.55-7.51 (m, 1H), 7.48-7.43 (m, 2H), 4.42 (s, 2H), 4.22-4.05 (m, 1H), 3.93 (s, 2H), 3.60-3.49 (m, 1H), 3.47-3.35 (m, 4H), 3.12-2.95 (m, 4H), 2.92 (s, 3H), 2.88-2.81 (m, 1H), 2.15 (dd, J$_1$ = 8.0 Hz, J$_2$ = 24.0 Hz, 2H), 2.01 (d, J = 8.0 Hz, 1H), 1.69-1.55 (m, 2H), 1.49-1.32 (m, 2H), 1.01-0.89 (m, 4H), MS m/z 643.4 [M + H]$^+$. |
| 27 | UNC3439A | +++ | ++ | ++ | $^1$H NMR (400 MHz, CD$_3$OD) δ 8.66 (dd, J$_1$ = 2.0 Hz, J$_2$ = 8.0 Hz, 1H), 7.78-7.77 (m, 1H), 7.76-7.71 (m, 2H), 7.71-7.66 (m, 2H), 7.64 (d, J = 8.0 Hz, 1H), 7.57 (dd, J$_1$ = 2.0 Hz, J$_2$ = 8.0 Hz, 2H), 7.52-7.48 (m, 1H), 7.48-7.43 (m, 2H), 4.20 (s, 2H), 4.18-4.06 (m, 1H), 3.94-3.80 (m, 3H), 3.58-3.49 (m, 1H), 3.47-3.34 (m, 4H), 3.13-2.93 (m, 4H), 2.91 (s, 3H), 2.43-2.33 (m, 2H), 2.31-2.21 (m, 2H), 2.21-2.07 (m, 2H), 2.04-1.89 (m, 4H), 1.70-1.54 (m, 2H), 1.50-1.31 (m, 2H), MS m/z 657.4 [M + H]$^+$. |
| 28 | UNC3440A | ++ | ++ | ++ | $^1$H NMR (400 MHz, CD$_3$OD) δ 8.66 (dd, J$_1$ = 2.0 Hz, J$_2$ = 8.0 Hz, 1H), 7.79-7.77 (m, 1H), 7.75-7.60 (m, 6H), 7.55-7.50 (m, 2H), 7.45-7.40 (m, 2H), 4.31 (s, 2H), 4.17-4.05 (m, 1H), 3.72 (s, 2H), 3.70-3.61 (m, 1H), 3.60-3.41 (m, 4H), 3.21-3.03 (m, 4H), 2.89 (s, 2H), 2.27-2.14 (m, 2H), 2.04-1.95 (m, 2H), 1.94-1.80 (m, 2H), 1.79-1.65 (m, 4H), 1.52-1.27 (m, 2H), MS m/z 671.4 [M + H]$^+$. |
| 29 | UNC3441A | +++ | ++ | ++ | $^1$H NMR (400 MHz, CD$_3$OD) δ 8.66 (dd, J$_1$ = 2.0 Hz, J$_2$ = 8.0 Hz, 1H), 7.81-7.78 (m, 1H), 7.76-7.71 (m, 2H), 7.71-7.66 (m, 2H), 7.64 (d, J = 8.0 Hz, 1H), 7.57 (dd, J$_1$ = 2.0 Hz, J$_2$ = 8.0 Hz, 2H), 7.54-7.51 (m, 1H), 7.48-7.43 (m, 2H), 4.34 (s, 2H), 4.22-4.06 (m, 1H), 3.93 (s, 3H), 3.58-3.49 (m, 1H), 3.48-3.35 (m, 4H), 3.25-3.15 (m, 1H), 3.13-2.95 (m, 4H), 2.92 (s, 3H), 2.27-2.14 (m, 3H), 2.14-2.07 (m, 1H), 2.01 (d, J = 8.0 Hz, 2H), 1.96-1.86 (m, 2H), 1.78-1.70 (m, 1H), 1.66-1.54 (m, 3H), 1.50-1.33 (m, 5H), 1.32-1.18 (m, 1H), MS m/z 685.4 [M + H]$^+$. |

TABLE 3-continued describes compounds could be prepared following procedures described in Example 3, using appropriate reagents.

| Structure | Compound_ID | Mer IC$_{50}$ | Axl IC$_{50}$ | Tyro3 IC$_{50}$ | Physical Data MS m/z (M + 1) or/and $^1$H NMR |
|---|---|---|---|---|---|
| 30 | UNC3445A | +++ | +++ | +++ | $^1$H NMR (400 MHz, CD$_3$OD) δ 8.80 (dd, J$_1$ = 2.0 Hz, J$_2$ = 8.0 Hz, 1H), 8.66 (dt, J$_1$ = 4.0 Hz, J$_2$ = 8.0 Hz, 1H), 8.49 (s, 1H), 8.23 (dd, J$_1$ = 1.0 Hz, J$_2$ = 2.0 Hz, 1H), 8.00-7.97 (m, 3H), 7.80-7.74 (m, 4H), 7.48-7.44 (m, 1H), 4.57-4.47 (m, 1H), 4.16-4.08 (m, 1H), 3.76-7.62 (m, 1H), 2.43-3.33 (m, 2H), 2.25-2.12 (m, 3H), 2.10-2.02 (m, 2H), 1.87-1.78 (m, 2H), 1.64-1.52 (m, 2H), 1.51-1.39 (m, 2H), 1.33-1.27 (m, 1H), MS m/z 560.3 [M + H]$^+$. |
| 31 | UNC3446A | +++ | +++ | +++ | $^1$H NMR (400 MHz, CD$_3$OD) δ 8.83 (dd, J$_1$ = 2.0 Hz, J$_2$ = 8.0 Hz, 1H), 8.66 (dd, J$_1$ = 4.0 Hz, J$_2$ = 8.0 Hz, 1H), 8.50 (s, 1H), 8.31 (dd, J$_1$ = 1.0 Hz, J$_2$ = 2.0 Hz, 1H), 8.06 (dd, J$_1$ = 4.0 Hz, J$_2$ = 8.0 Hz, 1H), 8.04-7.96 (m, 2H), 7.83-7.76 (m, 4H), 7.49-7.46 (m, 1H), 4.39-4.30 (m, 1H), 4.17-4.07 (m, 1H), 3.75-3.64 (m, 1H), 2.24-2.16 (m, 2H), 2.13-2.01 (m, 4H), 1.86-1.74 (m, 2H), 1.72-1.55 (m, 4H), 1.54-1.37 (m, 4H), MS m/z 574.3 [M + H]$^+$. |
| 32 | UNC3447A | +++ | +++ | ++ | $^1$H NMR (400 MHz, CD$_3$OD) δ 8.81 (dd, J$_1$ = 2.0 Hz, J$_2$ = 8.0 Hz, 1H), 8.66 (dd, J$_1$ = 4.0 Hz, J$_2$ = 8.0 Hz, 1H), 8.49 (s, 1H), 8.27 (dd, J$_1$ = 1.0 Hz, J$_2$ = 2.0 Hz, 1H), 8.02 (dd, J$_1$ = 4.0 Hz, J$_2$ = 8.0 Hz, 1H), 8.01-7.98 (m, 2H), 7.82-7.74 (m, 4H), 7.49-7.44 (m, 1H), 4.16-4.07 (m, 1H), 3.94-3.84 (m, 1H), 3.76-3.63 (m, 1H), 2.25-2.15 (m, 2H), 2.10-2.02 (m, 2H), 2.02-1.94 (m, 2H), 1.88-1.80 (m, 2H), 1.74-1.66 (m, 1H), 1.64-1.52 (m, 2H), 1.52-1.35 (m, 6H), 1.32-1.18 (m, 1H), MS m/z 588.3 [M + H]$^+$. |
| 33 | UNC3448A | ++++ | ++++ | ++++ | $^1$H NMR (400 MHz, CD$_3$OD) δ 8.82 (dd, J$_1$ = 2.0 Hz, J$_2$ = 8.0 Hz, 1H), 8.66 (dd, J$_1$ = 4.0 Hz, J$_2$ = 8.0 Hz, 1H), 8.49 (s, 1H), 8.27 (dd, J$_1$ = 1.0 Hz, J$_2$ = 2.0 Hz, 1H), 8.03 (dd, J$_1$ = 4.0 Hz, J$_2$ = 8.0 Hz, 1H), 8.01-7.96 (m, 2H), 7.82-7.75 (m, 4H), 7.49-7.44 (m, 1H), 4.28-4.18 (m, 1H), 4.16-4.07 (m, 1H), 3.75-3.65 (m, 1H), 2.20 (dd, J$_1$ = 4.0 Hz, J$_2$ = 8.0 Hz, 2H), 2.06 (dd, J$_1$ = 4.0 Hz, J$_2$ = 8.0 Hz, 2H), 1.65-1.51 (m, 2H), 1.51-1.39 (m, 2H), 1.29 (d, J = 8.0 Hz, 6H), MS m/z 548.3 [M + H]$^+$. |

TABLE 3-continued describes compounds could be prepared following procedures described in Example 3, using appropriate reagents.

| Structure | Compound_ID | Mer IC$_{50}$ | Axl IC$_{50}$ | Tyro3 IC$_{50}$ | Physical Data MS m/z (M + 1) or/and $^1$H NMR |
|---|---|---|---|---|---|
| 34 | UNC3449A | +++ | +++ | ++ | $^1$H NMR (400 MHz, CD$_3$OD) δ 8.77 (dd, J$_1$ = 2.0 Hz, J$_2$ = 8.0 Hz, 1H), 8.16 (dd, J$_1$ = 1.0 Hz, J$_2$ = 2.0 Hz, 1H), 7.91 (dd, J$_1$ = 2.0 Hz, J$_2$ = 4.0 Hz, 1H), 7.78 (s, 1H), 7.76-7.73 (m, 4H), 7.58 (d, J = 8.0 Hz, 1H), 7.57 (dd, J$_1$ = 2.0 Hz, J$_2$ = 8.0 Hz, 2H), 7.55-7.51 (m, 1H), 7.48-7.43 (m, 2H), 4.18-4.08 (m, 1H), 4.08-3.78 (m, 4H), 3.93 (s, 2H), 3.74-3.48 (m, 3H), 3.26-3.08 (m, 2H), 2.95-2.88 (m, 1H), 2.06-1.97 (m, 4H), 1.77-1.72 (m, 2H), 1.55-1.40 (m, 3H), 1.40-1.32 (m, 3H), 0.88-0.83 (m, 2H), 0.71-0.67 (m, 2H), MS m/z 670.4 [M + H]$^+$. |
| 35 | UNC3456A | ++++ | ++++ | ++++ | $^1$H NMR (400 MHz, CD$_3$OD) δ 8.79 (dd, J$_1$ = 2.0 Hz, J$_2$ = 8.0 Hz, 1H), 8.70 (dd, J$_1$ = 1.0 Hz, J$_2$ = 2.0 Hz, 1H), 8.61 (s, 1H), 8.27 (dd, J$_1$ = 1.0 Hz, J$_2$ = 2.0 Hz, 1H), 8.07-7.98 (m, 3H), 7.80 (d, J = 8.0 Hz, 2H), 7.74 (d, J = 8.0 Hz, 2H), 4.16-4.08 (m, 1H), 3.89-3.47 (m, 10H), 2.95-2.88 (m, 1H), 2.21 (d, J = 12.0 Hz, 2H), 2.08 (d, J = 12.0 Hz, 2H), 1.64-1.52 (m, 2H), 1.52-1.42 (m, 2H), 0.89-0.83 (m, 2H), 0.73-0.68 (m, 2H), MS m/z 659.3 [M + H]$^+$. |
| 36 | UNC3457A | +++ | +++ | ++ | $^1$H NMR (400 MHz, CD$_3$OD) δ 8.74 (d, J = 4.0 Hz, 1H), 8.70 (dd, J$_1$ = 2.0 Hz, J$_2$ = 4.0 Hz, 1H), 8.01 (d, J = 8.0 Hz, 2H), 7.98 (dd, J$_1$ = 2.0 Hz, J$_2$ = 8.0 Hz, 1H), 7.76 (d, J = 8.0 Hz, 2H), 7.69 (d, J = 8.0 Hz, 2H), 7.52-7.50 (m, 1H), 7.49 (s, 1H), 4.11-3.98 (m, 1H), 3.59-3.49 (m, 1H), 2.94-2.87 (m, 1H), 2.02 (t, J = 12.0 Hz, 4H), 1.64-1.52 (m, 2H), 1.49-1.31 (m, 4H), 0.88-0.82 (m, 2H), 0.72-0.66 (m, 2H), MS m/z 625.2 [M + H]$^+$. |
| 37 | UNC3458A | ++++ | ++++ | ++++ | $^1$H NMR (400 MHz, CD$_3$OD) δ 8.82 (dd, J$_1$ = 2.0 Hz, J$_2$ = 8.0 Hz, 1H), 8.70 (dt, J$_1$ = 1.0 Hz, J$_2$ = 4.0 Hz, 1H), 8.50 (s, 1H), 8.27 (dd, J$_1$ = 1.0 Hz, J$_2$ = 2.0 Hz, 1H), 8.04-7.96 (m, 3H), 7.82-7.74 (m 4H), 7.49-7.45 (m, 1H), 4.17-4.07 (m, 1H) 3.75-3.64 (m, 1H), 3.47 (q, J = 8.0 Hz, 2H), 2.20 (d, J = 12.0 Hz, 2H), 2.06 (d, J = 12.0 Hz, 2H), 1.64-1.52 (m, 2H), 1.52-1.40 (m, 2H), 1.26 (t, J = 0.8 Hz, 3H), MS m/z 534.3 [M + H]$^+$. |

TABLE 3-continued describes compounds could be prepared following procedures described in Example 3, using appropriate reagents.

| | Structure | Compound_ID | Mer IC$_{50}$ | Axl IC$_{50}$ | Tyro3 IC$_{50}$ | Physical Data MS m/z (M + 1) or/and $^1$H NMR |
|---|---|---|---|---|---|---|
| 38 | 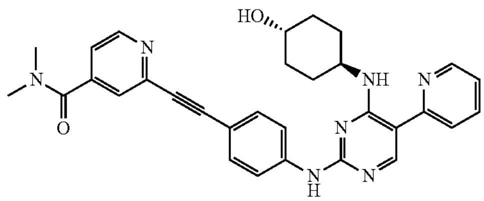 [SMILES: CN(C)C(=O)c1ccnc(C#Cc2ccc(Nc3ncc(-c4ccccn4)c(N[C@H]4CC[C@H](O)CC4)n3)cc2)c1] | UNC3459A | +++ | + | ++++ | $^1$H NMR (400 MHz, CD$_3$OD) δ 8.85 (dd, J$_1$ = 2.0 Hz, J$_2$ = 8.0 Hz, 1H), 8.67 (dd, J$_1$ = 2.0 Hz, J$_2$ = 8.0 Hz, 1H), 8.50 (s, 1H), 8.15-8.12 (m, 1H), 8.08-7.98 (m, 3H), 7.89-7.85 (m, 1H), 7.85-7.77 (m, 4H), 7.53-7.48 (m, 1H), 4.16-4.07 (m, 1H), 3.74-3.65 (m, 1H), 3.15 (s, 3H), 3.01 (s, 3H), 2.20 (d, J = 12.0 Hz, 2H), 2.06 (d, J = 12.0 Hz, 2H), 1.64-1.52 (m, 2H), 1.52-1.40 (m, 2H), MS m/z 534.3 [M + H]$^+$. |
| 39 | 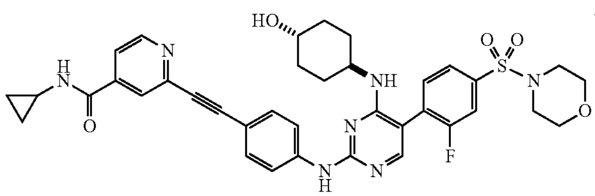 | UNC3614A | ++ | +++ | + | $^1$H NMR (400 MHz, CD$_3$OD) δ 8.72 (d, J = 4.0 Hz, 1H), 8.05 (s, 1H), 7.82-7.78 (m, 2H), 7.75-7.65 (m, 7H), 4.17-4.07 (m, 1H), 3.73 (t, J = 4.0 Hz, 4H), 3.57-3.45 (m, 1H), 3.06 (t, J = 4.0 Hz, 4H), 2.92-2.86 (m, 1H), 1.98 (t, J = 12.0 Hz, 4H), 1.52-1.40 (m, 2H), 1.40-1.24 (m, 2H), 0.86-0.80 (m, 2H), 0.69-0.64 (m, 2H), MS m/z 712.3 [M + H]$^+$. |
| 40 | 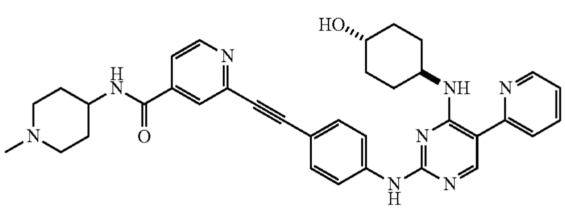 | UNC3615A | +++ | + | ++ | $^1$H NMR (400 MHz, CD$_3$OD) δ 8.85 (d, J = 4.0 Hz, 1H), 8.67-8.65 (m, 1H), 8.48 (s, 1H), 8.36 (dd, J$_1$ = 2.0 Hz, J$_2$ = 4.0 Hz, 1H), 8.10 (dd, J$_1$ = 2.0 Hz, J$_2$ = 4.0 Hz, 1H), 8.06-7.96 (m, 2H), 7.82-7.75 (m, 4H), 7.51-7.47 (m, 1H), 4.23-4.05 (m, 2H), 3.69-3.56 (m, 1H), 3.47-3.42 (m, 1H), 3.15 (s, 3H), 3.23-3.13 (m, 2H), 2.88 (s, 3H), 2.27 (d, J = 12.0 Hz, 2H), 2.18 (d, J = 12.0 Hz, 2H), 2.08-1.92 (m, 4H), 1.62-1.51 (m, 2H), 1.51.01.38-(m, 2H), MS m/z 603.3 [M + H]$^+$. |
| 41 | 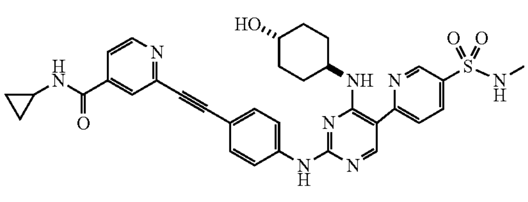 | UNC3617A | ++++ | +++ | ++++ | $^1$H NMR (400 MHz, CD$_3$OD) δ 9.02 (dd, J$_1$ = 2.0 Hz, J$_2$ = 4.0 Hz, 1H), 8.68 (d, J = 4.0 Hz, 1H), 8.58 (s, 1H), 8.30 (dd, J$_1$ = 4.0 Hz, J$_2$ = 8.0 Hz, 1H), 8.13 (d, J = 8.0 Hz, 1H), 7.98 (dd, J$_1$ = 1.0 Hz, J$_2$ = 4.0 Hz, 1H), 7.73 (dd, J$_1$ = 1.0 Hz, J$_2$ = 2.0 Hz, 1H), 7.71 (s, 4H), 4.15-4.03 (m, 1H), 3.74-3.60 (m, 1H), 2.93-2.83 (m, 1H), 2.61 (s, 3H), 2.02 (d, J = 12.0 Hz, 2H), 2.05 (d, J = 12.0 Hz, 2H), 1.63-1.49 (m, 2H), 1.49-1.35 (m, 2H), 0.89-0.77 (m, 2H), 0.68-0.62 (m, 2H), MS m/z 639.2 [M + H]$^+$. |

TABLE 3-continued describes compounds could be prepared following procedures described in Example 3, using appropriate reagents.

| | Structure | Compound_ID | Mer IC$_{50}$ | Axl IC$_{50}$ | Tyro3 IC$_{50}$ | Physical Data MS m/z (M + 1) or/and $^1$H NMR |
|---|---|---|---|---|---|---|
| 42 | 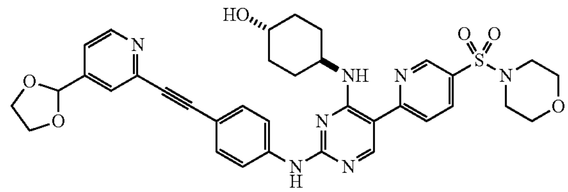 | UNC3619A | ++++ | ++ | ++++ | $^1$H NMR (400 MHz, CD$_3$OD) δ 8.99 (d, J = 4.0 Hz, 1H), 8.72 (d, J = 8.0 Hz, 1H), 8.67 (s, 1H), 8.26 (dd, J$_1$ = 4.0 Hz, J$_2$ = 8.0 Hz, 1H), 8.19 (d, J = 8.0 Hz, 1H), 8.06 (s, 1H), 7.85 (dd, J$_1$ = 1.0 Hz, J$_2$ = 4.0 Hz, 1H), 7.82-7.73 (m, 4H), 5.97 (m, 1H), 3.73 (t, J = 4.0 Hz, 4H), 3.07 (t, J = 4.0 Hz, 4H), 2.19 (d, J = 12.0 Hz, 2H), 2.06 (d, J = 12.0 Hz, 2H), 1.65-1.53 (m, 2H), 1.50-1.39 (m, 2H), MS m/z 684.2 [M + H]$^+$. |
| 43 | 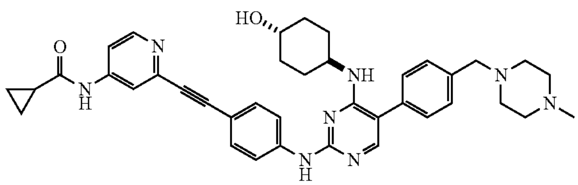 | UNC3622A | ++++ | ++++ | ++++ | $^1$H NMR (400 MHz, CD$_3$OD) δ 8.52 (d, J = 8.0 Hz, 1H), 8.34 (d, J = 4.0 Hz, 1H), 7.97 (dd, J$_1$ = 4.0 Hz, J$_2$ = 8.0 Hz, 1H), 7.82-7.75 (m, 3H), 7.73-7.66 (m, 3H), 7.51 (d, J = 8.0 Hz, 2H), 4.34-4.26 (m, 1H), 4.15-4.03 (m, 1H), 3.75-3.45 (m, 10H), 2.97 (s, 3H), 2.04-1.94 (m, 4H), 1.92-1.85 (m, 1H), 1.57-1.43 (m, 2H), 1.43-1.30 (m, 2H), 1.10-1.05 (m, 2H) 1.05-1.01 (m, 2H), MS m/z 657.0 [M + H]$^+$. |
| 44 | 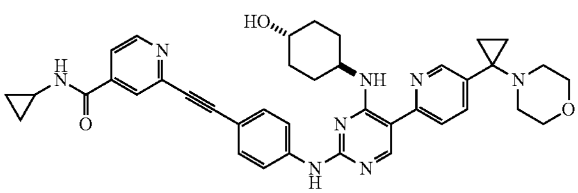 | UNC3632A | ++++ | ++++ | ++++ | $^1$H NMR (400 MHz, CD$_3$OD) δ 8.87 (dd, J$_1$ = 2.0 Hz, J$_2$ = 4.0 Hz, 1H), 8.71 (dd, J$_1$ = 2.0 Hz, J$_2$ = 4.0 Hz, 1H), 8.58 (s, 1H), 8.18 (dd, J$_1$ = 2.0 Hz, J$_2$ = 4.0 Hz, 1H), 8.09 (dd, J$_1$ = 2.0 Hz, J$_2$ = 4.0 Hz, 1H), 8.04 (dd, J$_1$ = 1.0 Hz, J$_2$ = 2.0 Hz, 1H), 7.79 (dd, J$_1$ = 2.0 Hz, J$_2$ = 4.0 Hz, 1H), 7.75-7.69 (m, 4H), 4.16-4.07 (m, 1H), 3.95-3.87 (m, 4H), 3.74-3.54 (m, 5H), 2.92-2.86 (m, 1H), 2.22-2.14 (m, 2H), 2.09-2.01 (m, 2H), 1.76-1.70 (m, 2H), 1.62-1.41 (m, 6H), 1.41-1.35 (m, 2H), 0.86-0.80 (m, 2H), 0.69-0.64 (m, 2H), MS m/z 671.2 [M + H]$^+$. |
| 45 | 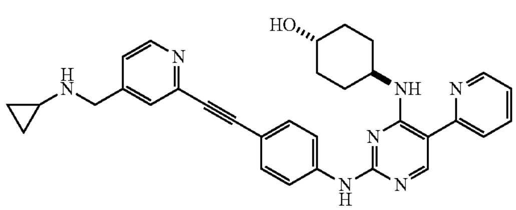 | UNC3661A | +++ | +++ | +++ | $^1$H NMR (400 MHz, CD$_3$OD) δ 8.79 (d, J = 4.0 Hz, 1H), 8.67-8.64 (m, 1H), 8.48 (s, 1H), 8.10 (d, J = 1.0 Hz, 1H), 8.03-7.96 (m, 2H), 7.84 (dd, J$_1$ = 2.0 Hz, J$_2$ = 4.0 Hz, 1H), 7.81-7.72 (m, 4H), 7.49-7.45 (m, 1H), 4.55 (s, 2H), 4.15-4.05 (m, 1H), 3.73-3.64 (m, 1H), 2.92-2.85 (m, 1H), 2.18 (d, J = 12.0 Hz, 2H), 2.15 (d, J = 12.0 Hz, 2H), 1.62-1.50 (m, 2H), 1.50-1.38 (m, 2H), 1.02-0.95 (m, 4H), MS m/z 532.3 [M + H]$^+$. |
| 46 | 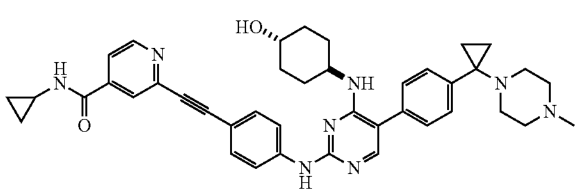 | UNC3662A | +++ | ++++ | +++ | $^1$H NMR (400 MHz, CD$_3$OD) δ 8.79 (dd, J$_1$ = 2.0 Hz, J$_2$ = 8.0 Hz, 1H), 8.23 (dd, J$_1$ = 2.0 Hz, J$_2$ = 8.0 Hz, 1H), 7.98 (dd, J$_1$ = 2.0 Hz, J$_2$ = 8.0 Hz, 1H), 7.75 (s, 4H), 7.63 (s, 1H), 7.58 (d, J = 8.0 Hz, 2H), 7.45 (d, J = 8.0 Hz, 2H), 4.14-4.04 (m, 1H), 3.59-3.39 (m, 5H), 3.27-3.17 (m, 2H), 2.99-2.87 (m, 3H), 2.83 (s, 3H), 1.98 (d, J = 12.0 |

TABLE 3-continued describes compounds could be prepared following procedures described in Example 3, using appropriate reagents.

| Structure | Compound_ID | Mer IC$_{50}$ | Axl IC$_{50}$ | Tyro3 IC$_{50}$ | Physical Data MS m/z (M + 1) or/and $^1$H NMR |
|---|---|---|---|---|---|
| | | | | | Hz, 4H), 1.60-1.47 (m, 3H), 1.40-1.26 (m, 5H), 1.09-1.03 (m, 2H), 0.87-0.82 (m, 2H), 0.71-0.66 (m, 2H), MS m/z 683.0 [M + H]$^+$. |
| 47 | UNC3663A | +++ | +++ | +++ | $^1$H NMR (400 MHz, CD$_3$OD) δ 9.08 (dd, J$_1$ = 2.0 Hz, J$_2$ = 4.0 Hz, 1H), 8.74 (dd, J$_1$ = 2.0 Hz, J$_2$ = 4.0 Hz, 1H), 8.61 (s, 1H), 8.35 (dd, J$_1$ = 2.0 Hz, J$_2$ = 4.0 Hz, 1H), 8.13 (dd, J$_1$ = 2.0 Hz, J$_2$ = 4.0 Hz, 1H), 8.10-8.08 (m, 1H), 7.84 (dd, J$_1$ = 2.0 Hz, J$_2$ = 4.0 Hz, 1H), 7.75 (s, 4H), 4.18-4.09 (m, 1H), 3.75-3.64 (m, 1H), 2.95-2.88 (m, 1H), 2.20 (d, J = 12.0 Hz, 2H), 2.08 (d, J = 12.0 Hz, 2H), 1.67-1.55 (m, 2H), 1.51-1.39 (m, 2H), 1.25 (s, 9H), 0.89-0.82 (m, 2H), 0.71-0.66 (m, 2H), MS m/z 671.2 [M + H]$^+$. |
| 48 | UNC4040A | ++++ | ++ | ++++ | $^1$H NMR (400 MHz, CD$_3$OD) δ 8.57 (d, J = 8.0 Hz, 1H), 8.41 (d, J = 4.0 Hz, 1H), 8.14 (t, J = 8.0 Hz, 1H), 7.97 (dd, J$_1$ = 4.0 Hz, J$_2$ = 8.0 Hz, 1H), 7.75-7.63 (m, 5H), 7.52 (d, J = 8.0 Hz, 2H), 4.36-4.22 (m, 2H), 4.07-3.95 (m, 1H), 3.81-3.44 (m, 9H), 2.98 (s, 3H), 2.80-2.70 (m, 1H), 2.02-1.90 (m, 4H), 1.55-1.41 (m, 2H), 1.35-1.27 (m, 2H), 1.24 (d, J = 8 Hz, 6H), 1.10-1.05 (m, 2H), 1.05-1.01 (m, 2H), MS m/z 677.1 [M + H]$^+$. |
| 49 | UNC4041A | +++ | ++ | +++ | $^1$H NMR (400 MHz, CD$_3$OD) δ 8.52 (d, J = 8.0 Hz, 1H), 8.31 (d, J = 2.0 Hz, 1H), 7.95 (dd, J$_1$ = 4.0 Hz, J$_2$ = 8.0 Hz, 1H), 7.82-7.75 (m, 4H), 7.65 (s, 1H), 7.57-7.49 (m, 3H), 7.47-7.40 (m, 2H), 4.15-4.05 (m, 1H), 3.61-3.50 (m, 1H), 2.78-2.69 (m, 1H), 2.04-1.96 (m, 4H), 1.54-1.39 (m, 2H), 1.41-1.30 (m, 1H), 1.24 (d, J = 8.0 Hz, 6H), 0.91 (d, J = 8.0 Hz, 1H), MS m/z 547.1 [M + H]$^+$. |
| 50 | UNC4042A | ++++ | ++++ | ++++ | $^1$H NMR (400 MHz, CD$_3$OD) δ 8.65 (dt, J$_1$ = 2.0 Hz, J$_2$ = 4.0 Hz, 1H), 8.52 (d, J = 8.0 Hz, 1H), 8.52 (s, 1H), 8.36 (d, J = 4.0 Hz, 1H), 8.02-7.96 (m, 3H), 7.86-7.77 (m, 4H), 7.45 (dd, J$_1$ = 4.0 Hz, J$_2$ = 8.0 Hz, 1H), 4.17-4.07 (m, 1H), 3.75-3.65 (m, 1H), 2.79-2.70 (m, 1H), 2.24-2.16 (m, 2H), 2.11-2.04 (m, 2H), 1.64-1.53 (m, 2H), 1.53-1.40 (m, 2H), 1.25 (d, J = 4.0 Hz, 6H), MS m/z 548.0 [M + H]$^+$. |

TABLE 3-continued describes compounds could be prepared following procedures described in Example 3, using appropriate reagents.

| | Structure | Compound_ID | Mer IC$_{50}$ | Axl IC$_{50}$ | Tyro3 IC$_{50}$ | Physical Data MS m/z (M + 1) or/and $^1$H NMR |
|---|---|---|---|---|---|---|
| 51 | 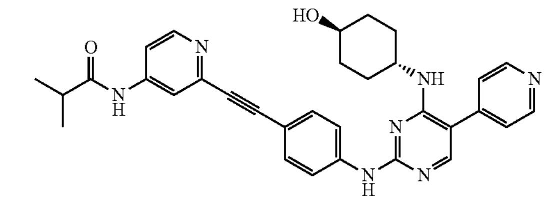 [SMILES: CC(C)C(=O)Nc1ccnc(C#Cc2ccc(Nc3ncc(-c4ccncc4)c(N[C@H]4CC[C@H](O)CC4)n3)cc2)c1] | UNC4043A | ++++ | +++ | ++++ | $^1$H NMR (400 MHz, CD$_3$OD) δ 8.94 (d, J = 8.0 Hz, 1H), 8.55 (d, J = 8.0 Hz, 1H), 8.38 (d, J = 2.0 Hz, 1H), 8.21 (d, J = 4.0 Hz, 1H), 8.09 (s, 1H), 8.65 (dd, J$_1$ = 4.0 Hz, J$_2$ = 8.0 Hz, 1H), 8.85-8.79 (m, 4H), 4.15-4.07 (m, 1H), 3.61-3.53 (m, 1H), 2.79-2.71 (m, 1H), 2.11-2.00 (m, 4H), 1.54-1.42 (m, 2H), 1.42-1.31 (m, 2H), 1.25 (d, J = 4.0 Hz, 6H), MS m/z 548.1 [M + H]$^+$. |
| 52 | 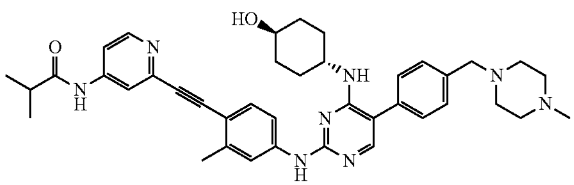 [SMILES: Cc1cc(Nc2ncc(-c3ccc(CN4CCN(C)CC4)cc3)c(N[C@H]3CC[C@H](O)CC3)n2)ccc1C#Cc1cc(NC(=O)C(C)C)ccn1] | UNC4044A | ++++ | ++++ | ++++ | $^1$H NMR (400 MHz, CD$_3$OD) δ 8.55 (d, J = 4.0 Hz, 1H), 8.38 (d, J = 2.0 Hz, 1H), 8.02 (dd, J$_1$ = 4.0 Hz, J$_2$ = 8.0 Hz, 1H), 7.77-7.66 (m, 5H), 7.61 (dd, J$_1$ = 4.0 Hz, J$_2$ = 8.0 Hz, 1H), 7.52 (d, J = 8.0 Hz, 2H), 4.39-4.27 (m, 2H), 4.19-4.09 (m, 1H), 3.78-3.43 (m, 9H), 2.98 (s, 3H), 2.79-2.71 (m, 1H), 2.65 (s, 3H), 2.05-1.95 (m, 4H), 1.59-1.45 (m, 2H), 1.42-1.28 (m, 2H), 1.25 (d, J = 4.0 Hz, 6H), MS m/z 673.1 [M + H]$^+$. |
| 53 | 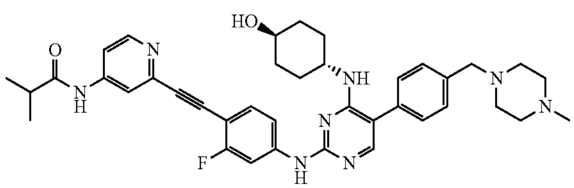 [SMILES: CC(C)C(=O)Nc1ccnc(C#Cc2ccc(Nc3ncc(-c4ccc(CN5CCN(C)CC5)cc4)c(N[C@H]4CC[C@H](O)CC4)n3)cc2F)c1] | UNC4045A | ++++ | ++++ | ++++ | $^1$H NMR (400 MHz, CD$_3$OD) δ 8.55 (d, J = 8.0 Hz, 1H), 8.38 (d, J = 4.0 Hz, 1H), 8.05 (dd, J$_1$ = 2.0 Hz, J$_2$ = 8.0 Hz, 1H), 7.94 (dd, J$_1$ = 4.0 Hz, J$_2$ = 12.0 Hz, 1H), 7.79 (t, J = 8.0 Hz, 1H), 7.75-7.70 (m, 3H), 7.54 (d, J = 8.0 Hz, 1H), 7.48 (dd, J$_1$ = 2.0 Hz, J$_2$ = 8.0 Hz, 1H), 4.40-4.30 (m, 2H), 4.19-4.10 (m, 1H), 3.83-3.41 (m, 9H), 2.99 (s, 3H), 2.79-2.70 (m, 1H), 2.07-1.97 (m, 4H), 1.61-1.48 (m, 2H), 1.48-1.35 (m, 2H), 1.25 (d, J = 4.0 Hz, 6H), MS m/z 677.2 [M + H]$^+$. |
| 54 | 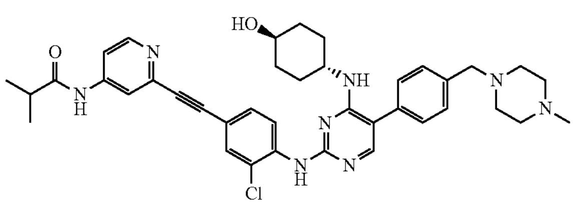 [SMILES: CC(C)C(=O)Nc1ccnc(C#Cc2ccc(Nc3ncc(-c4ccc(CN5CCN(C)CC5)cc4)c(N[C@H]4CC[C@H](O)CC4)n3)c(Cl)c2)c1] | UNC4046A | +++ | ++++ | +++ | $^1$H NMR (400 MHz, CD$_3$OD) δ 8.58 (d, J = 8.0 Hz, 1H), 8.41 (d, J = 4.0 Hz, 1H), 8.05 (dd, J$_1$ = 2.0 Hz, J$_2$ = 8.0 Hz, 1H), 8.15 (d, J = 8.0 Hz, 1H), 8.04 (dd, J$_1$ = 2.0 Hz, J$_2$ = 8.0 Hz, 1H), 7.97 (d, J = 2.0 Hz, 1H), 7.79 (dd, J$_1$ = 4.0 Hz, J$_2$ = 8.0 Hz, 1H), 7.75 (s, 1H), 7.71 (d, J = 8.0 Hz, 2H), 7.52 (d, J = 8.0 Hz, 2H), 4.37-4.25 (m, 2H), 4.02-3.91 (m, 1H), 3.79-3.45 (m, 9H), 2.98 (s, 3H), 2.80-2.71 (m, 1H), 2.00-1.88 (m, 4H), 1.54-1.41 (m, 2H), 1.32-1.26 (m, 2H), 1.24 (d, J = 8.0 Hz, 6H), MS m/z 693.0 [M + H]$^+$. |
| 55 | 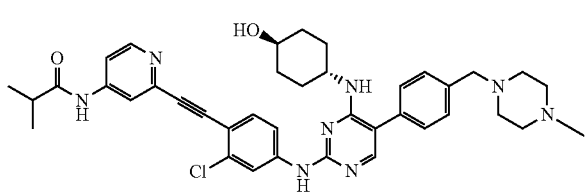 [SMILES: CC(C)C(=O)Nc1ccnc(C#Cc2ccc(Nc3ncc(-c4ccc(CN5CCN(C)CC5)cc4)c(N[C@H]4CC[C@H](O)CC4)n3)cc2Cl)c1] | UNC4047A | ++++ | ++++ | ++++ | $^1$H NMR (400 MHz, CD$_3$OD) δ 8.56 (d, J = 8.0 Hz, 1H), 8.40 (d, J = 4.0 Hz, 1H), 8.23 (d, J = 4.0 Hz, 1H), 8.06 (dd, J$_1$ = 2.0 Hz, J$_2$ = 8.0 Hz, 1H), 7.84 (d, J = 12.0 Hz, 1H), 7.76-7.69 (m, 3H), 7.58 (dd, J$_1$ = 4.0 Hz, J$_2$ = 8.0 Hz, 1H), 7.53 (d, J = 8.0 Hz, 1H), 4.40-4.28 (m, 2H), 4.20-4.10 (m, 1H), 3.80-3.39 (m, 9H), 2.98 (s, 3H), 2.79-2.69 |

TABLE 3-continued describes compounds could be prepared following procedures described in Example 3, using appropriate reagents.

| | Structure | Compound_ID | Mer IC$_{50}$ | Axl IC$_{50}$ | Tyro3 IC$_{50}$ | Physical Data MS m/z (M + 1) or/and $^1$H NMR |
|---|---|---|---|---|---|---|
| | | | | | | (m, 4H), 2.05-1.95 (m, 4H), 1.60-1.38 (m, 2H), 1.25 (d, J = 4.0 Hz, 6H), MS m/z 693.0 [M + H]$^+$. |
| 56 | 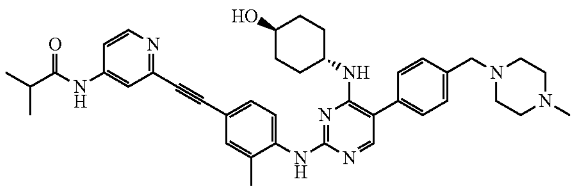 [SMILES: Cc1cc(C#Cc2cc(NC(=O)C(C)C)ccn2)ccc1Nc1ncc(-c2ccc(CN3CCN(C)CC3)cc2)c(N[C@H]2CC[C@H](O)CC2)n1] | UNC4048A | +++ | ++ | +++ | $^1$H NMR (400 MHz, CD$_3$OD) δ 8.53 (d, J = 8.0 Hz, 1H), 8.38 (d, J = 2.0 Hz, 1H), 8.02 (dd, J$_1$ = 2.0 Hz, J$_2$ = 8.0 Hz, 1H), 7.79 (d, J = 8.0 Hz, 1H), 7.73 (s, 1H), 7.72-7.65 (m, 3H), 7.64 (s, 1H), 7.50 (d, J = 8.0 Hz, 2H), 4.33-4.19 (m, 2H), 4.00-3.89 (m, 1H), 3.76-3.39 (m, 9H), 2.97 (s, 3H), 2.78-2.70 (m, 1H), 2.42 (s, 3H), 2.00-1.84 (m, 4H), 1.50-1.37 (m, 2H), 1.32-1.26 (m, 2H), 1.30-1.13 (m, 8H), MS m/z 673.0 [M + H]$^+$. |
| 57 | 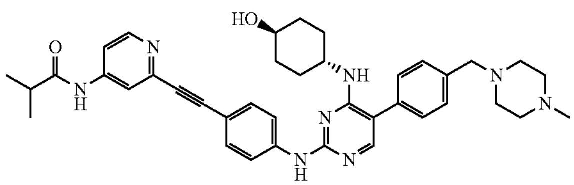 [SMILES: CC(C)C(=O)Nc1ccnc(C#Cc2ccc(Nc3ncc(-c4ccc(CN5CCN(C)CC5)cc4)c(N[C@H]4CC[C@H](O)CC4)n3)cc2)c1] | UNC3870A | ++++ | ++++ | ++++ | $^1$H NMR (400 MHz, CD$_3$OD) δ 8.55 (d, J = 4.0 Hz, 1H), 8.38 (d, J = 4.0 Hz, 1H), 8.03 (dd, J$_1$ = 2.0 Hz, J$_2$ = 8.0 Hz, 1H), 7.84-7.78 (m, 4H), 7.72 (d, J = 8.0 Hz, 1H), 7.69 (s, 1H), 7.53 (d, J = 8.0 Hz, 2H), 4.38-4.29 (m, 2H), 4.16-4.06 (m, 1H), 3.77-3.43 (m, 9H), 2.99 (s, 3H), 2.80-2.70 (m, 1H), 2.05-1.97 (m, 4H), 1.58-1.44 (m, 2H), 1.43-1.29 (m, 2H), 1.25 (d, J = 4.0 Hz, 6H), MS m/z 659.0 [M + H]$^+$. |
| 58 | 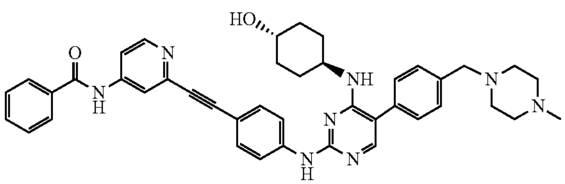 [SMILES: CN1CCN(Cc2ccc(-c3cnc(Nc4ccc(C#Cc5cc(NC(=O)c6ccccc6)ccn5)cc4)nc3N[C@H]3CC[C@H](O)CC3)cc2)CC1] | UNC3868A | ++++ | +++ | +++ | $^1$H NMR (400 MHz, CD$_3$OD) δ 8.63 (d, J = 8.0 Hz, 1H), 8.57 (d, J = 8.0 Hz, 1H), 8.25 (dd, J$_1$ = 4.0 Hz, J$_2$ = 8.0 Hz, 1H), 8.04 (dd, J$_1$ = 2.0 Hz, J$_2$ = 8.0 Hz, 1H), 7.82 (s, 4H), 7.74-7.66 (m, 4H), 7.59 (t, J = 8.0 Hz, 2H), 7.53 (d, J = 8.0 Hz, 2H), 4.32 (s, 2H), 4.18-4.07 (m, 2H), 3.82-3.39 (m, 8H), 2.98 (s, 3H), 2.06-1.96 (m, 4H), 0.89-0.81 (m, 2H), 1.60-1.44 (m, 2H), 1.45-1.25 (m, 2H), MS m/z 693.0 [M + H]$^+$. |
| 59 | 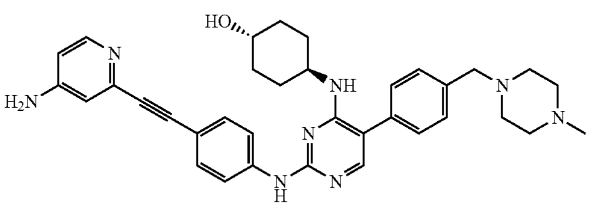 [SMILES: CN1CCN(Cc2ccc(-c3cnc(Nc4ccc(C#Cc5cc(N)ccn5)cc4)nc3N[C@H]3CC[C@H](O)CC3)cc2)CC1] | UNC3869A | +++ | + | ++ | $^1$H NMR (400 MHz, CD$_3$OD) δ 8.00 (d, J = 8.0 Hz, 1H), 7.79 (d, J = 12.0 Hz, 2H), 7.74 (d, J = 12.0 Hz, 2H), 7.68 (t, J = 4.0 Hz, 2H), 7.50 (d, J = 8.0 Hz, 2H), 7.01 (d, J = 2.0 Hz, 2H), 6.62 (dd, J$_1$ = 2.0 Hz, J$_2$ = 8.0 Hz, 1H), 4.20 (s, 2H), 4.15-4.05 (m, 2H), 3.75-3.40 (m, 8H), 2.96 (s, 3H), 2.05-1.95 (m, 4H), 1.57-1.44 (m, 2H), 1.43-1.27 (m, 2H), MS m/z 589.0 [M + H]$^+$. |
| 60 | 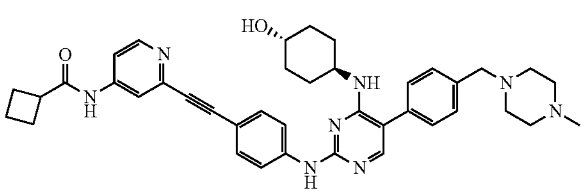 [SMILES: CN1CCN(Cc2ccc(-c3cnc(Nc4ccc(C#Cc5cc(NC(=O)C6CCC6)ccn5)cc4)nc3N[C@H]3CC[C@H](O)CC3)cc2)CC1] | UNC3871A | ++++ | +++ | ++++ | $^1$H NMR (400 MHz, CD$_3$OD) δ 8.53 (d, J = 8.0 Hz, 1H), 8.37 (d, J = 4.0 Hz, 2H), 8.02 (dd, J$_1$ = 2.0 Hz, J$_2$ = 8.0 Hz, 1H), 7.84-7.77 (m, 4H), 7.73-7.67 (m, 3H), 7.52 (d, J = 8.0 Hz, 2H), 4.29 (s, 2H), 4.17-4.06 (m, 2H), 3.76-3.36 (m, 8H), 2.98 (s, 3H), 2.43-2.34 (m, 2H), 2.35-2.25 (m, 2H), 2.13-2.05 (m, 1H), 2.05-1.92 (m, 4H), 1.57- |

TABLE 3-continued describes compounds could be prepared following procedures described in Example 3, using appropriate reagents.

| Structure | Compound_ ID | Mer IC$_{50}$ | Axl IC$_{50}$ | Tyro3 IC$_{50}$ | Physical Data MS m/z (M + 1) or/and $^1$H NMR |
|---|---|---|---|---|---|
| (61) | | | | | 1.45 (m, 2H), 1.43-1.31 (m, 2H), 1.06-0.97 (m, 2H), MS m/z 671.0 [M + H]$^+$. |
| 61 | UNC3872A | ++++ | ++++ | ++++ | $^1$H NMR (400 MHz, CD$_3$OD) δ 8.54 (d, J = 8.0 Hz, 1H), 8.38 (d, J = 4.0 Hz, 2H), 8.01 (dd, J$_1$ = 4.0 Hz, J$_2$ = 8.0 Hz, 1H), 7.84-7.77 (m, 4H), 7.72 (d, J = 8.0 Hz, 2H), 7.69 (s, 1H), 7.53 (dd, J$_1$ = 2.0 Hz, J$_2$ = 8.0 Hz, 1H), 4.34 (s, 2H), 4.16-4.03 (m, 2H), 3.78-3.36 (m, 8H), 2.99 (s, 3H), 2.97-2.91 (m, 1H), 2.06-1.95 (m, 6H), 1.94-1.83 (m, 2H), 1.83-1.72 (m, 2H), 1.72-1.64 (m, 2H), 1.58-1.43 (m, 2H), 1.42-1.29 (m, 2H), MS m/z 685.0 [M + H]$^+$. |
| 62 | UNC3873A | ++++ | +++ | +++ | $^1$H NMR (400 MHz, CD$_3$OD) δ 8.54 (d, J = 4.0 Hz, 1H), 8.36 (d, J = 4.0 Hz, 2H), 8.01 (dd, J$_1$ = 4.0 Hz, J$_2$ = 8.0 Hz, 1H), 7.84-7.78 (m, 4H), 7.72 (d, J = 8.0 Hz, 2H), 7.70 (s, 1H), 7.53 (d, J = 8.0 Hz, 2H), 4.34 (s, 2H), 4.16-4.06 (m, 2H), 3.81-3.37 (m, 8H), 2.98 (s, 3H), 2.55-2.45 (m, 1H), 2.05-1.95 (m, 5H), 1.94-1.90 (m, 1H), 1.89-1.81 (m, 2H), 1.78-1.70 (m, 2H), 1.59-1.45 (m, 4H), 1.46-1.32 (m, 4H), 1.31-1.23 (m, 1H), MS m/z 699.0 [M + H]$^+$. |
| 63 | UNC3874A | +++ | ++ | +++ | $^1$H NMR (400 MHz, CD$_3$OD) δ 8.54 (d, J = 4.0 Hz, 1H), 8.35 (d, J = 4.0 Hz, 2H), 7.96 (dd, J$_1$ = 2.0 Hz, J$_2$ = 8.0 Hz, 1H), 7.83-7.76 (m, 4H), 7.71 (d, J = 8.0 Hz, 2H), 7.69 (s, 1H), 7.52 (d, J = 8.0 Hz, 2H), 4.30 (s, 2H), 4.15-4.06 (m, 2H), 3.83-3.42 (m, 8H), 2.98 (s, 3H), 2.28 (s, 3H), 2.06-1.96 (m, 4H), 1.59-1.45 (m, 2H), 1.43-1.27 (m, 4H), MS m/z 631. [M + H]$^+$. |
| 64 | UNC3391A | +++ | +++ | ++ | $^1$H NMR (400 MHz, CD$_3$OD) δ 8.81 (d, J = 4.0 Hz, 1H), 8.38 (d, J = 4.0 Hz, 1H), 8.34 (dd, J$_1$ = 8.0 Hz, J$_2$ = 4.0 Hz, 1H), 7.75-7.71 (m, 4H), 7.61 (s, 1H), 5.97 (s, 1H), 4.09-4.03 (m, 1H), 3.81 (d, J = 4.0 Hz, 2H), 3.62-3.55 (m, 1H), 3.49 (t, J = 8.0 Hz, 2H), 2.95-2.89 (m, 1H), 2.04-1.97 (t, J = 12.0 Hz, 4H), 1.72 (q, J = 12.0 Hz, 2H), 1.35 (q, J = 12.0 Hz, 2H), 0.87-0.82 (m, 2H), 0.71-0.67 (m, 2H), MS m/z 550.30 [M + H]$^+$. |

TABLE 3-continued describes compounds could be prepared following procedures described in Example 3, using appropriate reagents.

| Structure | Compound_ID | Mer IC$_{50}$ | Axl IC$_{50}$ | Tyro3 IC$_{50}$ | Physical Data MS m/z (M + 1) or/and $^1$H NMR |
|---|---|---|---|---|---|
| 65 | UNC3430A | +++ | +++ | ++ | $^1$H NMR (400 MHz, CD$_3$OD) δ 8.85 (d, J = 4.0 Hz, 1H), 8.35 (d, J = 4.0 Hz, 1H), 8.20 (dd, J$_1$ = 8.0 Hz, J$_2$ = 4.0 Hz, 1H), 7.80-7.74 (m, 4H), 7.69 (s, 1H), 5.97 (s, 1H), 4.11-4.05 (m, 1H), 4.00 (d, J = 16.0 Hz, 1H), 3.79 (d, J = 16.0 Hz, 1H), 3.69 (dd, J$_1$ = 12.0 Hz, J$_2$ = 4.0 Hz, 1H), 3.61-3.75 (m, 1H), 3.47-3.40 (m, 1H), 3.00 (s, 3H), 2.97-2.92(m, 1H), 2.05-1.97 (m, 4H), 1.76-1.66 (m, 2H), 1.41-1.31 (m, 2H), 0.89-0.84 (m, 2H), 0.73-0.70 (m, 2H), MS m/z 564.30 [M + H]$^+$. |
| 66 | UNC3489A | ++ | ++ | ++ | $^1$H NMR (400 MHz, CD$_3$OD) δ 8.86 (d, J = 8.0 Hz, 1H), 8.51 (s, 1H), 8.25 (s, 1H), 8.20 (d, J = 8.0 Hz, 1H), 7.52 (d, J = 8.0 Hz, 2H), 7.36 (d, J = 8.0 Hz, 2H), 4.04-3.96 (m, 1H), 3.91 (s, 3H), 3.68-3.61 (m, 1H), 3.46 (t, J = 12.0 Hz, 2H), 3.20 (t, J = 12.0 Hz, 2H), 2.96-2.89 (m, 1H), 2.09 (d, J = 12.0 Hz, 2H), 2.00 (d, J = 12.0 Hz, 2H), 1.54-1.46 (m, 2H), 1.39-1.28 (m, 2H), 0.89-0.85 (m, 2H), 0.73-0.70 (m, 2H), MS m/z 531.20 [M + H]$^+$. |
| 67 | UNC3487A | ++++ | ++++ | +++ | $^1$H NMR (400 MHz, CD$_3$OD) δ 8.82 (d, J = 8.0 Hz, 1H), 8.52 (s, 1H), 8.26 (s, 1H), 8.02 (d, J = 8.0 Hz, 1H), 7.76 (m, 4H), 4.16-4.08 (m, 1H), 4.03-3.96 (m, 1H), 3.67-3.62 (m, 1H), 3.58 (d, J = 12.0 Hz, 2H), 3.16 (t, J = 12.0 Hz, 2H), 2.96-2.90 (m, 1H), 2.88 (s, 3H), 2.22 (d, J = 12.0 Hz, 2H), 2.11 (d, J = 12.0 Hz, 2H), 2.00 (d, J = 12.0 Hz, 2H), 2.00-1.94 (m, 2H), 1.54-1.37 (m, 4H), 0.87-0.85 (m, 2H), 0.72-0.69 (m, 2H), MS m/z 609.40. [M + H]$^+$. |
| 68 | UNC3488A | ++ | +++ | ++ | $^1$H NMR (400 MHz, CD$_3$OD) δ 8.80 (d, J = 8.0 Hz, 1H), 8.23 (s, 1H), 8.04 (s, 1H), 7.99 (d, J = 8.0 Hz, 1H), 7.75 (m, 4H), 4.45-4.38 (m, 1H), 4.09-3.00 (m, 1H), 3.65-3.46 (m, 4H), 3.25-3.19 (m, 1H), 2.96 (s, 3H), 2.05 (m, 4H), 1.56-1.45 (m, 2H), 1.40-1.35 (m, 2H), 0.86-0.86 (m, 2H), 0.72-0.68 (m, 2H), MS m/z 595.30. [M + H]$^+$. |

TABLE 3-continued describes compounds could be prepared following procedures described in Example 3, using appropriate reagents.

| Structure | Compound_ ID | Mer IC$_{50}$ | Axl IC$_{50}$ | Tyro3 IC$_{50}$ | Physical Data MS m/z (M + 1) or/and $^1$H NMR |
|---|---|---|---|---|---|
| 69 | UNC3442A | +++ | ++++ | +++ | $^1$H NMR (400 MHz, CD$_3$OD) δ 8.83 (d, J = 8.0 Hz, 1H), 8.31 (s, 1H), 8.04 (s, 1H), 8.06 (d, J = 4.0 Hz, 1H), 8.01 (s, 1H), 7.77 (m, 4H), 7.72 (d, J = 4.0 Hz, 1H), 6.81 (d, J$_1$ = 4.0 Hz, J$_2$ = 2.0 H, 1H), 6.62 (dd, J$_1$ = 4.0 Hz, J$_2$ = 2.0 H, 1H), 4.15-4.09 (m, 1H), 3.66-3.59 (m, 1H), 2.97-2.91 (m, 1H), 2.10-2.05 (m, 4H), 1.63-1.57 (m, 2H), 1.46-1.36 (m, 2H), 0.89-0.84 (m, 2H), 0.73-0.69 (m, 2H), MS m/z 535.30. [M + H]$^+$. |
| 70 | UNC3389A | +++ | +++ | ++ | $^1$H NMR (400 MHz, CD$_3$OD) δ 8.75 (d, J = 4.0 Hz, 1H), 8.36 (s, 1H), 8.15 (s, 1H), 8.06 (d, J = 4.0 Hz, 1H), 8.01 (s, 1H), 7.90 (s, 1H), 7.74-7.68 (m, 4H), 7.38-7.34 (m, 2H), 7.07-7.02 (m, 2H), 4.47 (s, 2H), 4.01-3.96 (m, 1H), 3.66-3.60 (m, 1H), 2.93-2.87 (m, 1H), 2.10 (d, J = 12.0 Hz, 2H), 2.01 (d, J = 12.0 Hz, 2H), 1.50-1.36 (m, 4H), 0.85-0.81 (m, 2H), 0.69-0.66 (m, 2H), MS m/z 620.30. [M + H]$^+$. |
| 71 | UNC3392A | +++ | ++ | + | $^1$H NMR (400 MHz, CD$_3$OD) δ 8.83 (d, J = 8.0 Hz, 1H), 8.31 (s, 1H), 8.07 (d, J = 8.0 Hz, 1H), 7.74-7.73 (m, 4H), 7.50 (s, 1H), 7.07-7.02 (m, 2H), 5.92-5.90 (m, 1H), 4.09-4.02 (m, 1H), 3.61-3.55 (m, 1H), 2.21-2.16 (m, 4H), 2.04-1.97 (m, 4H), 1.82-1.78 (m, 2H), 1.71-1.69 (m, 2H), 1.61-1.51 (m, 2H), 1.41-1.28 (m, 2H), 0.88-0.83 (m, 2H), 0.71-0.67 (m, 2H), MS m/z 549.30 [M + H]$^+$. |
| 72 | UNC3390A | +++ | +++ | ++ | $^1$H NMR (400 MHz, CD$_3$OD) δ 8.86 (d, J = 4.0 Hz, 1H), 8.36 (s, 1H), 8.12 (d, J = 8.0 Hz, 1H), 7.76 (m, 4H), 7.59 (s, 1H), 6.00 (s, 1H), 4.26-4.24 (m, 2H), 4.09-4.03 (m, 1H), 3.93-3.90 (m, 2H), 3.61-3.56 (m, 1H), 2.96-2.90 (m, 1H), 3.32-3.17 (m, 2H), 2.06-1.95 (m, 4H), 1.60-1.52 (m, 2H), 1.40-1.32 (m, 2H), 0.88-0.83 (m, 2H), 0.72-0.69 (m, 2H), MS m/z 551.30. [M + H]$^+$. |

Example 4 trans-4-((2-((4-((4-(Furan-2-yl)pyridin-2-yl)ethynyl)phenyl)amino)-5-(pyridin-2-yl)pyrimidin-4-yl)amino)cyclohexan-1-ol and trans-4-((2-((4-((4-((3-methoxyphenyl)amino)pyridin-2-yl)ethynyl)phenyl)amino)-5-(pyridin-2-yl)pyrimidin-4-yl)amino)cyclohexan-1-ol General Procedure D:

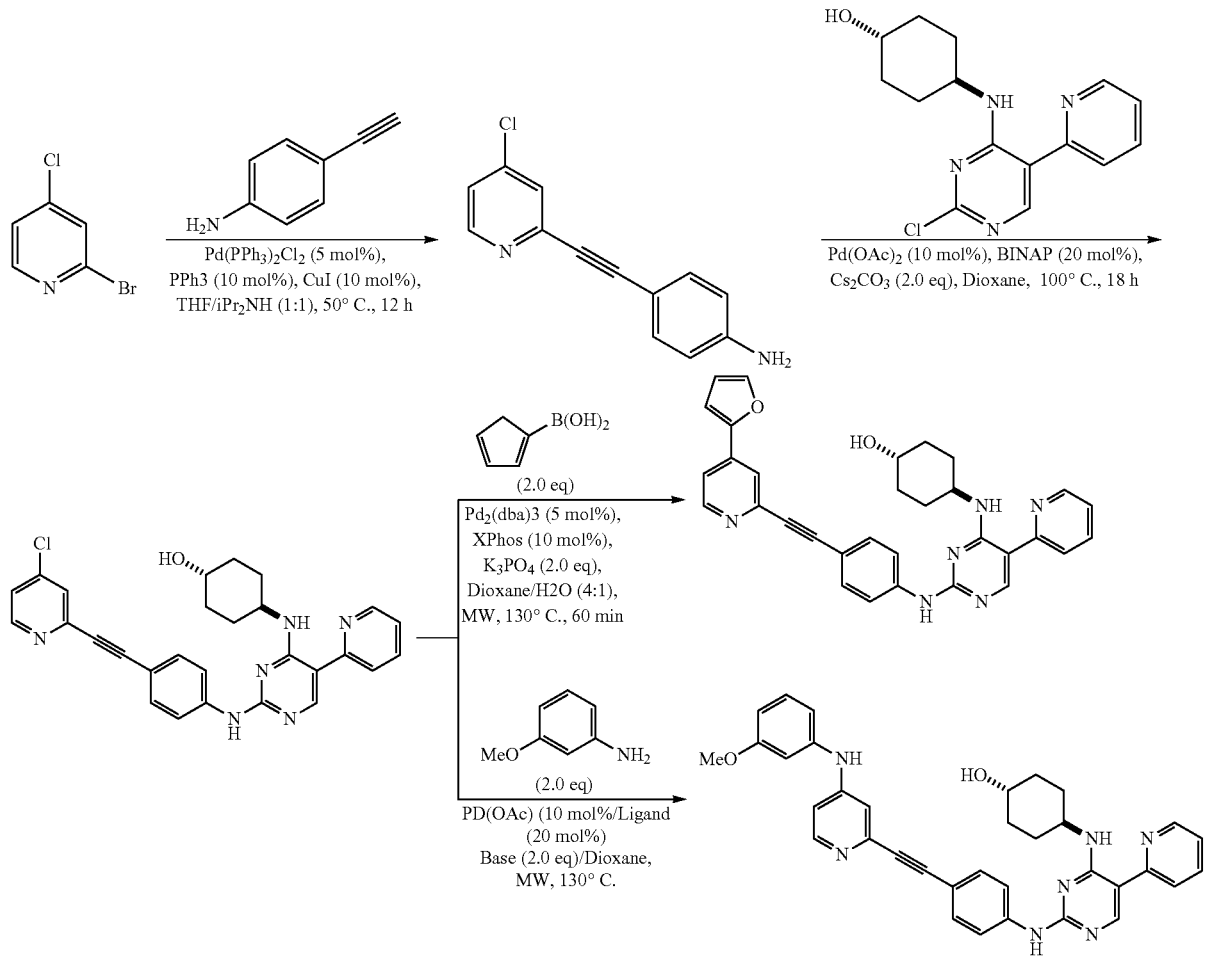

trans-4-((2-((4-((4-Chloropyridin-2-yl)ethynyl)phenyl)amino)-5-(pyridin-2-yl)pyrimidin-4-yl)amino)cyclohexan-1-ol

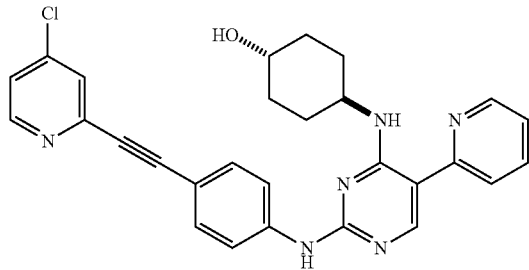

To a mixture of 2-bromo-4-chloropyridine (6e, 3.84 g, 20 mmol, 1.0 equivalent), 4-ethynylaniline (2.57 g, 22 mmol, 1.1 equivalent), Pd(PPh$_3$)$_2$Cl2 (702 mg, 1.0 mmol, 5 mol %), PPh$_3$ (524 mg, 2.0 mmol, 10 ml %) and CuI (382 mg, 2.0 mmol, 10 mol %) in a 100 mL round-bottom flask was added 50 mL $^i$Pr$_2$NH/THF (9:1) under nitrogen. The reaction mixture was stirred at 50° C. overnight, and then concentrated. The residue was purified by column chromatography with ISCO system to afford the desired compound 4-((4-chloropyridin-2-yl)ethynyl)aniline as a light yellow solid (4.1 g, 90%). $^1$H NMR (CD$_3$OD, 400 MHz): 8.45 (d, J=4.0 Hz, 1H), 7.80 (dd, J$_1$=8.0 Hz, J$_2$=4.0 Hz, 1H), 7.48 (d, J=8.0 Hz, 1H), 7.28 (d, J=8.0 Hz, 2H), 8.64 (d, J=8.0 Hz, 2H).

To a mixture of trans-4-((2-chloro-5-(pyridin-2-yl)pyrimidin-4-yl)amino)cyclohexan-1-ol (456 mg, 1.5 mmol, 1.0 equivalent), Pd(OAc)$_2$ (34 mg, 0.15 mmol, 10 mol %), BINAP (187 mg, 0.3 mmol, 20 mol %), Cs$_2$CO$_3$ (948 mg, 3.0 mmol, 2.0 equivalent), and 4-((4-chloropyridin-2-yl)ethynyl)aniline (410 mg, 1.8 mmol, 1.2 equivalent) in dioxane (20 mL) was heated at 100° C. overnight. The resulting mixture was cooled to room temperature, filtrated through a pad of celite, and concentrated. The residue was purified by column chromatography with ISCO system to afford the title compound as a yellow solid (350 mg, 47% yield). (UNC3427A) $^1$H NMR (DMSO-$D_6$, 400 MHz): 8.65 (d, J=4.0 Hz, 1H), 8.59 (d, J=4.0 Hz, 1H), 8.51 (s, 1H), 7.99-7.97 (m, 2H), 7.92 (dd, $J_1$=8.0 Hz, $J_2$=4.0 Hz, 1H), 7.75 (d, J=8.0 Hz, 2H), 7.68 (d, J=8.0 Hz, 2H), 7.64 (d, J=8.0 Hz, 1H), 4.16-4.09 (m, 2H), 3.72-3.66 (m, 2H), 2.22-2.19 (m, 2H), 2.09-2.05 (m, 2H), 1.63-1.42 (m, 4H). MS m/z 497.17 [M+H]$^+$.

trans-4-((2-((4-((4-(Furan-2-yl)pyridin-2-yl)ethynyl)phenyl)amino)-5-(pyridin-2-yl)pyrimidin-4-yl)amino)cyclohexan-1-ol

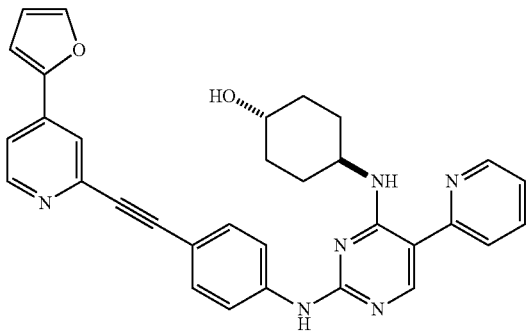

To a mixture of trans-4-((2-((4-((4-chloropyridin-2-yl)ethynyl)phenyl)amino)-5-(pyridin-2-yl)pyrimidin-4-yl)amino)cyclohexan-1-ol (50 mg, 0.10 mmol), furan-2-ylboronic acid (22 mg, 0.20 mmol), $Pd_2(dba)_3$ (4.5 mg, 5 mol %), XPhos (4.7 mg, 10 mol %) and $K_3PO_4$ (42.4 mg, 0.20 mmol) in a mixture of dioxane/$H_2O$ (4:1, 1.0 mL) was heated under microwave irradiation at 130° C. for 60 min under nitrogen atmosphere. The resulting mixture was cooled to room temperature, filtrated through a pad of celite, and concentrated. The residue was purified through preparative HPLC to afford the title product as a yellow solid (25 mg, 47%) (UNC4355A). $^1$H NMR (DMSO-$D_6$, 400 MHz): 11.06 (s, 1H), 10.52 (s, 1H), 8.94 (s, 1H), 8.67 (s, 1H), 8.63 (d, J=4.0 Hz, 1H), 8.09 (dd, $J_1$=8.0 Hz, $J_2$=4.0 Hz, 1H), 8.02 (d, J=8.0 Hz, 1H), 7.96 (dd, $J_1$=8.0 Hz, $J_2$=4.0 Hz, 1H), 7.67-7.65 (m, 1H), 4.00-3.95 (m, 2H), 2.06 (d, J=8.0 Hz, 2H), 1.90 (d, J=8.0 Hz, 2H), 1.47-1.42 (m, 4H); MS m/z 529.22 [M+H]$^+$.

trans-4-((2-((4-((4-(3-Methoxyphenyl)amino)pyridin-2-yl)ethynyl)phenyl)amino)-5-(pyridin-2-yl)pyrimidin-4-yl)amino)cyclohexan-1-ol

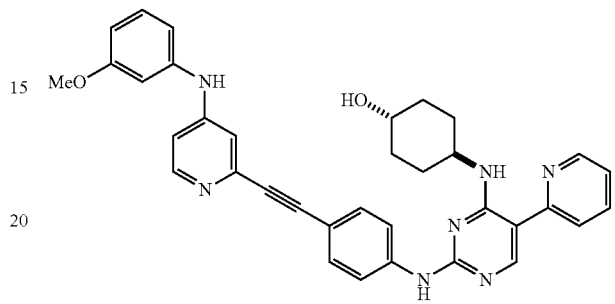

To a mixture of trans-4-((2-((4-((4-chloropyridin-2-yl)ethynyl)phenyl)amino)-5-(pyridin-2-yl)pyrimidin-4-yl)amino)cyclohexan-1-ol (50 mg, 0.10 mmol), Pd(OAc)$_2$ (2.3 mg, 10 mol %), BINAP (12 mg, 20 mol %), $Cs_2CO_3$ (73 mg, 0.20 mmol), and 3-methoxyaniline (25 mg, 0.20 mmol) in dioxane (2.0 mL) was heated under microwave irradiation at 130° C. for 2h under nitrogen atmosphere. The resulting mixture was cooled to room temperature, filtrated through a pad of celite, and concentrated. The residue was purified through preparative HPLC to afford the title product as a yellow solid (40 mg, 69%) (UNC4389A). $^1$H NMR ($CD_3OD$, 400 MHz): 8.64 (d, J=4.0 Hz, 1H), 8.48 (s, 1H), 8.22 (d, J=4.0 Hz, 1H), 8.00-7.97 (m, 3H), 7.90 (d, J=8.0 Hz, 1H), 7.98 (d, J=8.0 Hz, 2H), 7.71 (d, J=8.0 Hz, 2H), 7.47-743 (m, 2H), 7.34 (t, J=8.0 Hz, 1H), 6.87 (dd, $J_1$=8.0 Hz, $J_2$=4.0 Hz, 1H), 6.82 (m, 1H), 6.79 (dd, $J_1$=8.0 Hz, $J_2$=4.0 Hz, 1H), 4.12-4.06 (m, 1H), 3.80 (s, 3H), 3.74-3.69 (m, 1H), 3.57-3.55 (m, 1H), 2.17 (d, J=8.0 Hz, 2H), 2.03 (d, J=8.0 Hz, 2H), 1.61-1.54 (m, 2H), 1.48-1.41 (m, 2H); MS m/z 584.27 [M+1]$^+$.

TABLE 4 describes compounds could be prepared following procedures described in Example 4, using appropriate reagents.

| Structure | Compound_ID | Mer $IC_{50}$ | Axl $IC_{50}$ | Tryo3 $IC_{50}$ | Physical Data MS m/z (M + 1) or/and $^1$H NMR |
|---|---|---|---|---|---|
| 1 <br> (structure shown) | UNC4357A | ++ | + | ++ | $^1$H NMR (DMSO-$D_6$, 400 MHz): 11.17 (d, J = 8.0 Hz, 1H), 10.53 (s, 1H), 9.05 (d, J = 4.0 Hz, 1H), 8.68 (s, 1H), 8.63 (d, J = 4.0 Hz, 1H), 8.35 (br, 1H), 8.22 (dd, $J_1$ = 8.0 Hz, $J_2$ = 4.0 Hz, 1H), 8.04-7.96 (m, 2H), 7.81 (d, J = 4.0 Hz, 1H), 7.78 (d, J = 8.0 Hz, 1H), 7.69 (d, J = 8.0 Hz, 1H), 7.44-7.43 (m, 1H), 7.28 (s, 1H), 7.15 (s, 1H), 7.03 (s, 1H), 6.89 (d, J = 4.0 Hz, 1H), 4.01-3.93 (m, 2H), 2.07-2.04 (m, 2H), 1.91-1.88 (m, 2H), 1.51-1.32 (m, 4H); MS m/z 529.30 [M + H]$^+$. |

TABLE 4-continued describes compounds could be prepared following procedures described in Example 4, using appropriate reagents.

| Structure | Compound_ID | Mer IC$_{50}$ | Axl IC$_{50}$ | Tryo3 IC$_{50}$ | Physical Data MS m/z (M + 1) or/and $^1$H NMR |
|---|---|---|---|---|---|
| 2 | UNC4360A | ++ | + | ++ | $^1$H NMR (DMSO-D$_6$, 400 MHz): 11.24 (s, 1H), 10.81 (s, 1H), 8.92 (m, 2H), 8.70 (s, 1H), 8.63 (d, J = 4.0 Hz, 1H), 8.25-8.23 (m, 1H), 8.12 (br, 1H), 8.04-7.96 (m, 2H), 7.77 (d, J = 8.0 Hz, 2H), 7.65 (d, J = 8.0 Hz, 2H), 7.45-7.42 (m, 1H), 4.01-3.93 (m, 2H), 2.07-2.04 (m, 2H), 1.91-1.88 (m, 2H), 1.51-1.30 (m, 4H); MS m/z 529.25 [M + H]$^+$. |
| 3 | UNC4361A | ++ | ++ | ++ | $^1$H NMR (DMSO-D$_6$, 400 MHz): 11.30 (d, J = 8.0 Hz, 1H), 11.06 (s, 1H), 9.30 (m, 2H), 9.09 (d, J = 4.0 Hz, 1H), 8.87 (d, J = 8.0 Hz, 1H), 8.84 (d, J = 8.0 Hz, 1H), 8.75 (s, 1H), 8.63 (d, d, J = 4.0 Hz, 1H), 8.35 (dd, d, J$_1$ = 4.0 Hz, J$_2$ = 4.0 Hz, 1H), 8.08-7.95 (m, 2H), 7.84 (d, J = 8.0 Hz, 1H), 7.79 (d, J = 8.0 Hz, 2H), 7.67 (d, J = 8.0 Hz, 2H), 7.45-7.42 (m, 1H), 4.01-3.93 (m, 2H), 2.08-2.05 (d, J = 8.0 Hz, 2H), 1.92-1.80 (d, J = 8.0 Hz, 2H), 1.52-1.44 (dd, J$_1$ = 20.0 Hz, J$_2$ = 8.0 Hz, 2H), 1.39-1.31 (dd, J$_1$ = 20.0 Hz, J$_2$ = 8.0 Hz, 2H); MS m/z 540.30 [M + H]$^+$. |
| 4 | UNC4362A | +++ | ++ | ++ | $^1$H NMR (DMSO-D$_6$, 400 MHz): 11.27 (s, 1H), 10.92 (d, J = 8.0 Hz, 1H), 9.49 (s, 1H), 9.43 (s, 1H), 9.26-9.16 (m, 2H), 8.61 (s, 1H), 8.40 (s, 1H), 8.03 (m, 2H), 7.83 (d, J = 8.0 Hz, 1H), 7.81 (d, J = 8.0 Hz, 1H), 7.72 (d, J = 8.0 Hz, 1H), 7.68 (d, J = 8.0 Hz, 1H), 7.46 (m, 2H), 4.07-4.02 (m, 2H), 2.08-1.98 (m, 2H), 1.93-1.87 (m, 2H), 1.50-1.32 (m, 4H);. MS m/z 541.30 [M + H]$^+$. |
| 5 | UNC4363A | +++ | + | ++ | $^1$H NMR (DMSO-D$_6$, 400 MHz): 11.30 (d, J = 8.0 Hz, 1H), 11.08 (d, J = 8.0 Hz, 1H), 9.23 (d, J = 4.0 Hz, 1H), 8.98 (d, J = 8.0 Hz, 2H), 8.76 (s, 1H), 8.64 (d, J = 4.0 Hz, 1H), 8.49 (d, J = 8.0 Hz, 2H), 8.04-7.96 (m, 2H), 7.88 (d, J = 8.0 Hz, 1H), 7.79 (d, J = 8.0 Hz, 2H), 7.68 (d, J = 8.0 Hz, 2H), 7.46-743 (m, 2H), 3.99-3.96 (m, 2H), 2.07 (d, J = 8.0 Hz, 2H), 1.91 (d, J = 8.0 Hz, 2H), 1.50-1.44 (m, 2H), 1.39-1.33 (m, 2H); MS m/z 540.30 [M + H]$^+$. |

TABLE 4-continued describes compounds could be prepared following procedures described in Example 4, using appropriate reagents.

| | Structure | Compound_ID | Mer IC$_{50}$ | Axl IC$_{50}$ | Tryo3 IC$_{50}$ | Physical Data MS m/z (M + 1) or/and $^1$H NMR |
|---|---|---|---|---|---|---|
| 6 | (structure) | UNC4507A | ++ | ++ | ++ | $^1$H NMR (CD$_3$OD, 400 MHz): 8.62 (d, J = 4.0 Hz, 1H), 8.48 (s, 1H), 8.02 (s, 1H), 7.93 (d, J = 8.0 Hz, 1H), 7.71 (d, J = 8.0 Hz, 1H), 7.66-7.60 (m, 4H), 7.56-7.51 (m, 2H), 7.40 (dd, J$_1$ = 8.0 Hz, J$_2$ = 4.0 Hz, 1H), 7.21 (t, J = 8.0 Hz, 1H), 6.31 (d, J = 8.0 Hz, 1H), 6.82 (m, 1H), 6.99 (dt, J = 8.0 Hz, 1H), 4.12-4.07 (m, 1H), 3.85 (s, 3H), 3.71-3.66 (m, 1H), 2.19 (d, J = 8.0 Hz, 2H), 2.04 (d, J = 8.0 Hz, 2H), 1.61-1.51 (m, 2H), 1.48-1.39 (m, 2H); MS m/z 584.3 [M + H]$^+$. |
| 7 | (structure) | UNC4392A | ++ | + | ++ | $^1$H NMR (CD$_3$OD, 400 MHz): 9.14 (d, J = 8.0 Hz, 1H), 8.87 (d, J = 8.0 Hz, 1H), 8.63 (d, J = 4.0 Hz, 1H), 8.49 (s, 1H), 8.28-8.20 (m, 1H), 8.00 (d, J = 8.0 Hz, 1H), 7.97 (d, J = 8.0 Hz, 2H), 7.79 (d, J = 8.0 Hz, 2H), 7.74 (d, J = 8.0 Hz, 2H), 7.45-7.42 (m, 2H), 4.12-4.07 (m, 1H), 3.72-3.65 (m, 1H), 2.18 (d, J = 8.0 Hz, 2H), 2.04 (d, J = 8.0 Hz, 2H), 1.61-1.55 (m, 2H), 1.48-1.30 (m, 2H); MS m/z 545.30 [M + H]$^+$. |
| 8 | (structure) | UNC4391A | ++ | ++ | ++ | $^1$H NMR (CD$_3$OD, 400 MHz): 8.70 (t, J = 8.0 Hz, 1H), 8.64 (d, J = 4.0 Hz, 1H), 8.38 (d, J = 8.0 Hz, 1H), 8.49 (d, J = 8.0 Hz, 1H), 7.83 (d, J = 8.0 Hz, 1H), 7.78 (d, J = 8.0 Hz, 1H), 7.77-7.72 (m, 2H), 7.51-7.46 (m, 1H), 7.46-7.41 (m, 2H), 4.14-4.07 (m, 1H), 3.69-3.67 (m, 1H), 2.18 (d, J = 8.0 Hz, 2H), 2.04 (d, J = 8.0 Hz, 2H), 1.61-1.53 (m, 2H), 1.50-1.40 (m, 2H); MS m/z 581.20 [M + 1]$^+$. |
| 9 | (structure) | UNC4364A | +++ | ++ | +++ | $^1$H NMR (DMSO-D$_6$, 400 MHz): 10.74 (s, 1H), 10.47 (s, 1H), 8.72 (s, 1H), 8.67 (d, J = 8.0 Hz, 1H), 8.01 (d, J = 8.0 Hz, 2H), 7.76 (d, J = 8.0 Hz, 2H), 7.94-7.89 (m, 3H), 7.63 (d, J = 8.0 Hz, 2H), 7.37-7.34 (m, 1H), 7.11 (s, 1H), 6.98 (s, 1H), 6.84 (s, 1H), 6.78 (s, 1H), 3.97-3.93 (m, 2H), 3.71-3.68 (m, 1H), 2.18 (d, J = 8.0 Hz, 2H), 1.90 (d, J = 8.0 Hz, 2H), 1.47-1.29 (m, 4H), 1.19 (d, J = 8.0 Hz, 6H); MS m/z 520.27 [M + H]$^+$. |

Example 5 trans-4-((2-((4-((4-(Propylamino)pyridin-2-yl)ethynyl)phenyl)amino)-5-(pyridin-2-yl)pyrimidin-4-yl)amino)cyclohexan-1-ol General Procedure E:

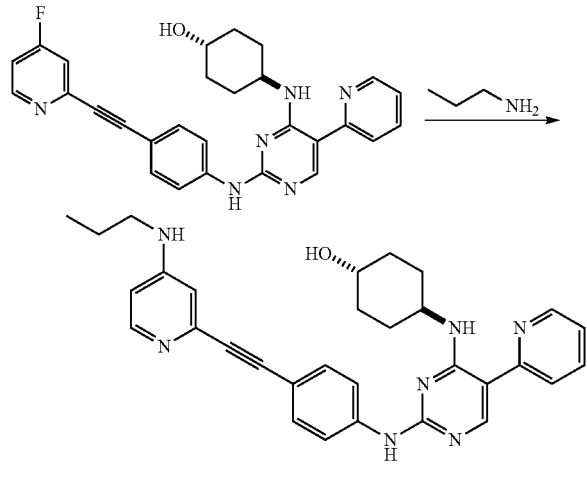

To a solution of trans-4-((2-((4-((4-fluoropyridin-2-yl)ethynyl)phenyl)amino)-5-(pyridin-2-yl)pyrimidin-4-yl)amino)cyclohexan-1-ol (24 mg, 0.05 mmol, 1.0 equivalent) and DIPEA (24 mg, 0.18 mmol) in $^i$PrOH (1.0 mL) was heated under microwave irradiation at 200° C. for 30 min. The resulting mixture was cooled to room temperature, filtrated through a pad of celite, and concentrated. The residue was purified through preparative HPLC to afford the title product as a white solid (12 mg, 36%) (UNC4390A). $^1$H NMR (CD$_3$OD, 400 MHz): 8.65 (d, J=4.0 Hz, 1H), 8.49 (s, 1H), 8.06 (d, J=8.0 Hz, 1H), 8.02-7.96 (m, 2H), 7.91 (d, J=8.0 Hz, 1H), 7.81-7.78 (m, 2H), 7.75-7.70 (m, 2H), 7.47-7.44 (m, 1H), 7.09 (d, J=4.0 Hz, 1H), 7.00 (d, J=4.0 Hz, 1H), 6.85 (dd, J$_1$=8.0 Hz, J$_2$=4.0 Hz, 1H), 6.80 (dd, J$_1$=8.0 Hz, J$_2$=4.0 Hz, 1H), 4.12-4.07 (m, 1H), 3.70-3.68 (m, 1H), 3.37-3.32 (td, J$_1$=8.0 Hz, J$_2$=4.0 Hz, 2H), 2.18 (d, J=8.0 Hz, 2H), 2.04 (d, J=8.0 Hz, 2H), 1.70-1.63 (m, 2H), 1.58-1.41 (m, 4H), 0.99 (t, J=8.0 Hz, 3H); MS m/z 534.29[M+1]$^+$.

TABLE 5 describes compounds could be prepared following procedures described in Example 5, using appropriate reagents.

| | Structure | Compound_ID | Mer IC$_{50}$ | Axl IC$_{50}$ | Tryo3 IC$_{50}$ | Physical Data MS m/z (M + 1) or/and $^1$H NMR |
|---|---|---|---|---|---|---|
| 1 | (structure) | UNC4394A | ++ | ++ | ++ | $^1$H NMR (CD$_3$OD, 400 MHz): 8.64 (d, J = 4.0 Hz, 1H), 8.54 (d, J = 4.0 Hz, 1H), 8.30 (s, 1H), 7.98-7.97 (m, 2H), 7.82 (d, J = 8.0 Hz, 2H), 7.79 (d, J = 8.0 Hz, 2H), 7.70 (d, J = 4.0 Hz, 1H), 7.46-7.42 (m, 2H), 5.10 (q, J = 8.0 Hz, 1H), 4.13-4.08 (m, 1H), 3.93-3.87 (m, 1H), 2.18 (d, J = 8.0 Hz, 2H), 2.07 (d, J = 8.0 Hz, 2H), 1.59-1.53 (m, 2H), 1.46 (d, J = 8.0 Hz, 6H), 1.32-1.27 (m, 4H); MS m/z 521.30 [M + H]$^+$. |
| 2 | (structure) | UNC4393A | + | + | + | $^1$H NMR (CD$_3$OD, 400 MHz): 8.64 (d, J = 4.0 Hz, 1H), 8.61 (d, J = 4.0 Hz, 1H), 8.50 (s, 1H), 7.97 (d, J = 4.0 Hz, 2H), 7.81 (d, J = 8.0 Hz, 2H), 7.76 (d, J = 8.0 Hz, 2H), 7.54 (d, J = 4.0 Hz, 1H), 7.48 (d, J = 8.0 Hz, 1H), 7.45-7.41 (m, 1H), 7.36 (dd, J$_1$ = 8.0 Hz, J$_2$ = 4.0 Hz, 1H), 7.02 (dd, J$_1$ = 8.0 Hz, J$_2$ = 4.0 Hz, 1H), 6.87 (s, 1H), 6.84 (d, J = 8.0 Hz, 1H), 4.13-4.06 (m, 1H), 3.71-3.68 (m, 1H), 2.18 (d, J = 8.0 Hz, 2H), 2.04 (d, J = 8.0 Hz, 2H), 1.61-1.52 (m, 2H), 1.49-1.38 (m, 4H); MS m/z 585.30 [M + H]$^+$. |

Example 6

Analysis of MerTK Inhibition in a Triple Negative Breast Cancer Cell Line (MDA-MB-231).

Figure 1B:
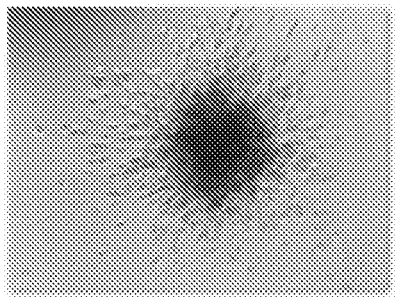
Figure 1C:
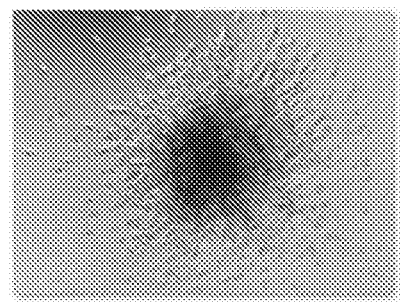
Figure 1D:
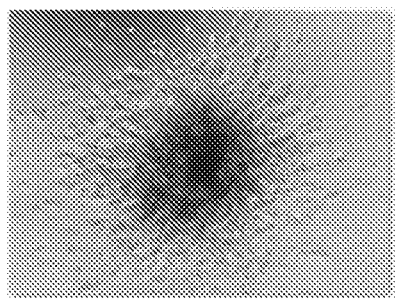
Figure 2A:
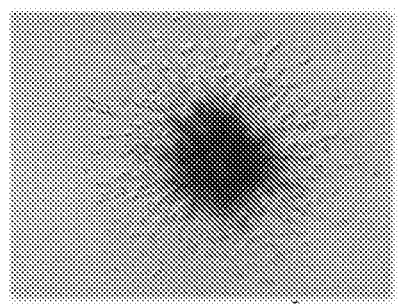
FIGS. 2A, 2B, 2C, and 2D show the growth of representative MDA-MB-231 spheroids after 24 hours in collagen culture after treatment with UNC2025. See Example 6.
Figure 2B:
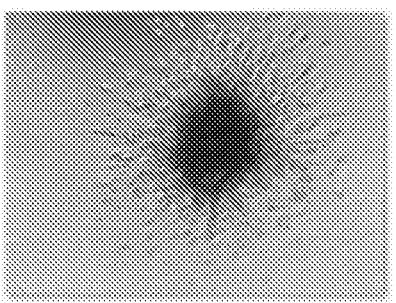
Figure 2C:
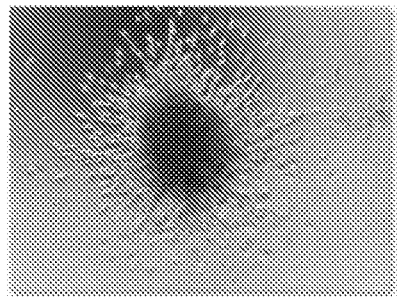
Figure 2D:
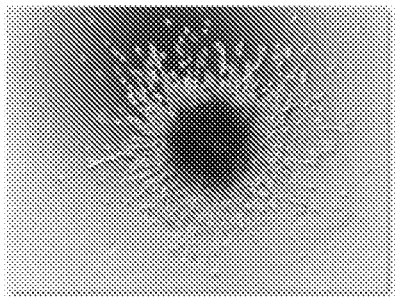
Figure 3A:
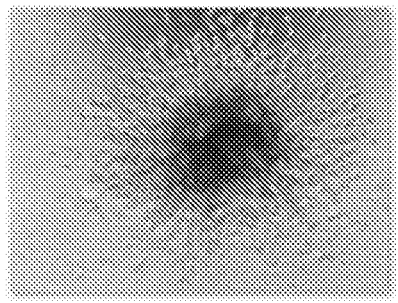
FIGS. 3A, 3B, 3C, and 3D show the growth of representative MDA-MB-231 spheroids after 24 hours in collagen culture after treatment with UNC2250. See Example 6.
Figure 3B:
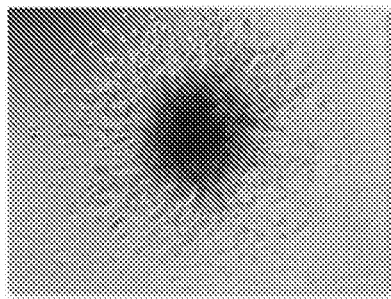
Figure 3C:
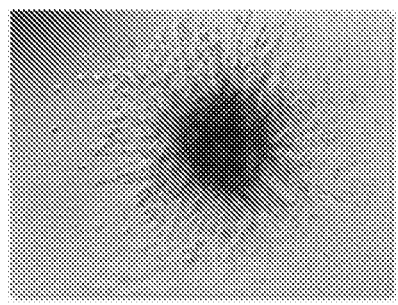
Figure 3D:
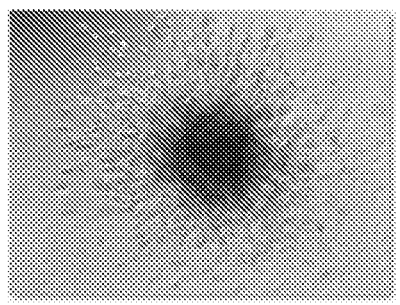
Figure 4A:
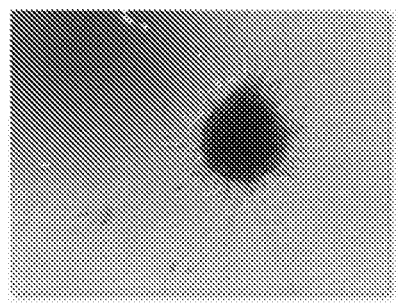
FIGS. 4A, 4B, 4C, and 4D show the growth of representative MDA-MB-231 spheroids after 24 hours in collagen culture after treatment with UNC4198. As discussed in Example 6, treatment of MDA-MB-231 (triple negative breast cancer) cells with the pan-TAM (Tyro3, Axl, MerTK) inhibitor UNC4198 resulted in decreased levels of invasion, in comparison to treatment with the inhibitors UNC1653 (FIG. 1), UNC2025 (FIG. 2), or UNC2250 (FIG. 3).
Figure 4B:
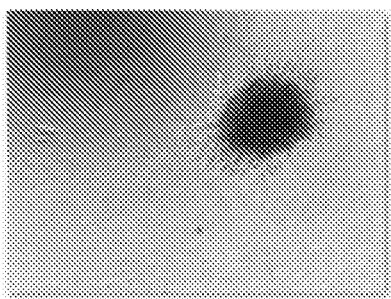
Figure 4C:
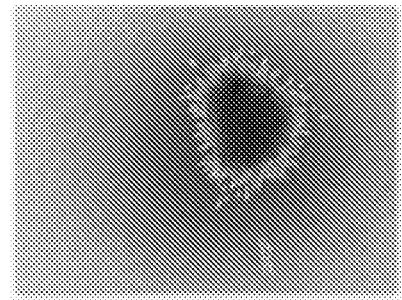
Figure 4D:
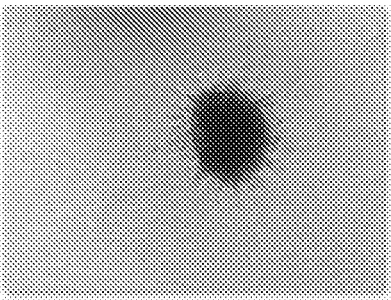

The invasion of triple negative highly aggressive breast adenocarcinoma cells (MDA-MB-231) cultured as multicellular tumor spheroids (MTSs) in a 3D collagen matrix was examined. Cells were treated with either UNC1653 (IC50s: MerTK=550 nM, Axl=7 µM, Tyro=15 µM, FLT3=220 nM), UNC2025 (IC50s: MerTK=0.74 nM, Axl=17 nM, Tyro3=25 nM, FLT3=0.84 nM), UNC2250 (IC50s: MerTK=1.7 nM, Axl=270 nM, Tyro3=100 nM, FLT3=7.9 nM), or UNC4198 (IC50s: MerTK=0.98 nM, Axl=5.5 nM, Tyro3=0.56 nM, FLT3=0.76 nM). As shown in FIG. 4, treatment of MDA-MB-231 cells with the pan-TAM (Tyro3, Axl, MerTK) inhibitor UNC4198 resulted in decreased levels of invasion, in comparison to treatment with the inhibitors UNC1653 (FIG. 1), UNC2025 (FIG. 2), or UNC2250 (FIG. 3).

That which is claimed is:

1. A compound of Formula I or II:

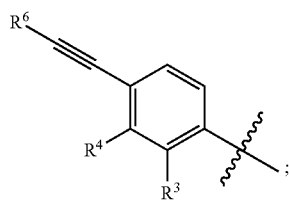

wherein:
X is —OH, —NH$_2$, —CH$_2$OH or —CH$_2$NH$_2$;
R$^1$ is substituted or unsubstituted aryl, substituted or unsubstituted heteroaryl, or substituted or unsubstituted cycloalkenyl, or substituted or unsubstituted heterocycloalkenyl;
R$^{1a}$ is substituted or unsubstituted alkyl, substituted or unsubstituted cycloalkyl, or substituted or unsubstituted aryl, substituted or unsubstituted heteroaryl, substituted or unsubstituted alkylaryl, substituted or unsubstituted alkylheteroaryl, or substituted or unsubstituted alkylcycloalkyl;
R$^2$ is

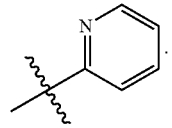 [SMILES: *c1ccccn1]

R$^3$ and R$^4$ are each independently H, halo, lower alkyl or lower alkoxyl; and
R$^6$ is substituted or unsubstituted heteroaryl, or a pharmaceutically acceptable salt thereof.

2. The compound of claim 1, wherein X is —OH.

3. The compound of claim 1, wherein R$^1$ is:

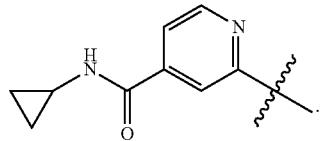 [SMILES: *c1cc(C(=O)NC2CC2)ccn1]

4. The compound of claim 1, wherein R$^6$ is

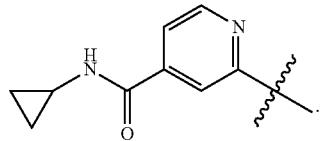 [SMILES: *c1cc(C(=O)NC2CC2)ccn1]

5. The compound of claim 1, wherein the compound is selected from the group consisting of:

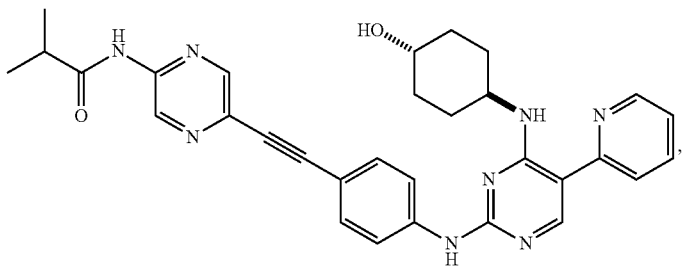

-continued
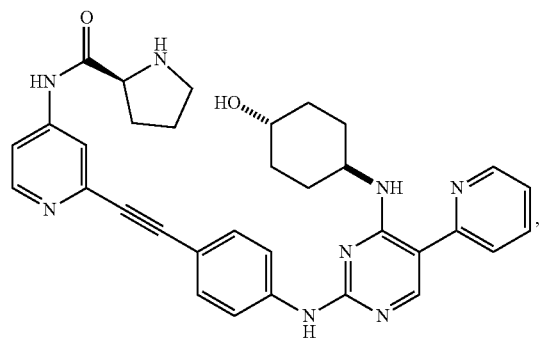
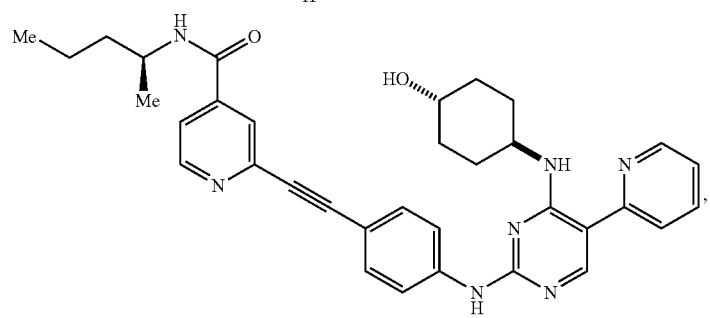
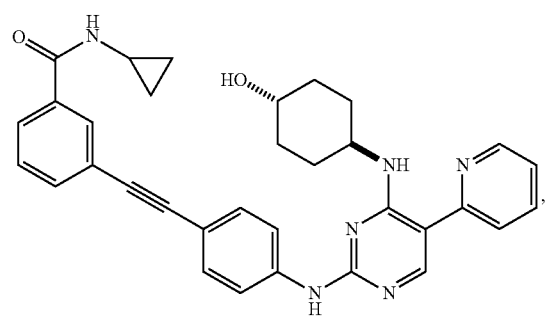
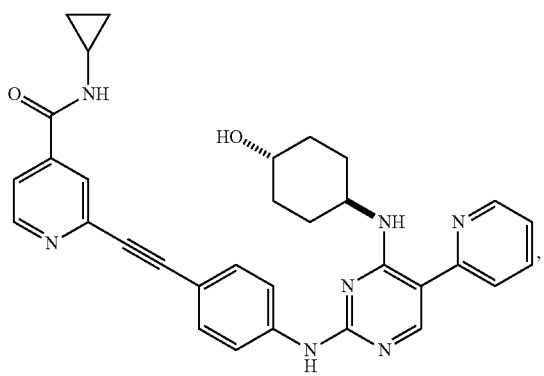
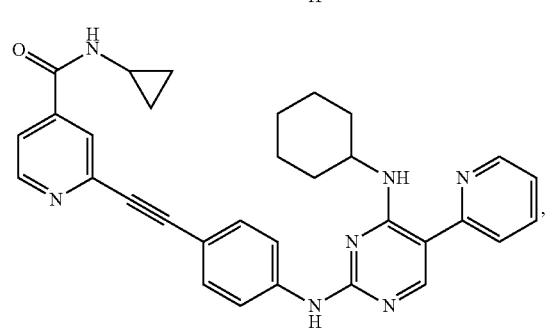
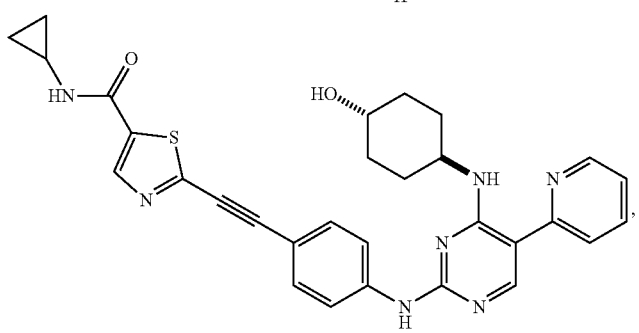
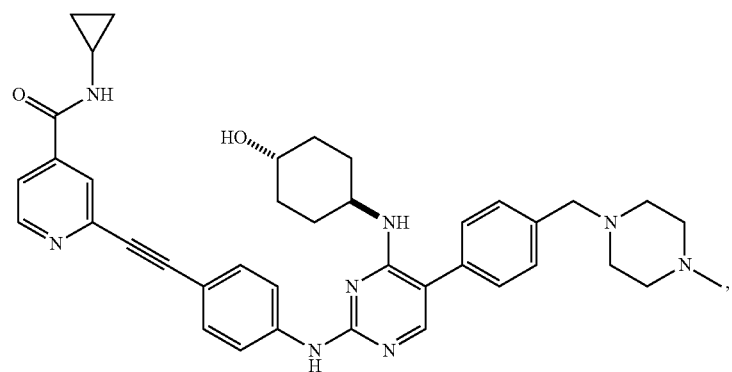

-continued
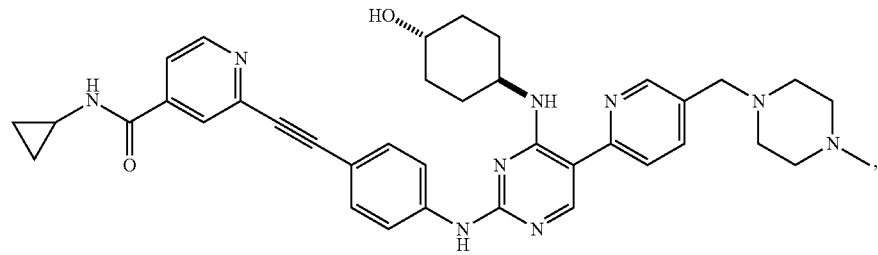
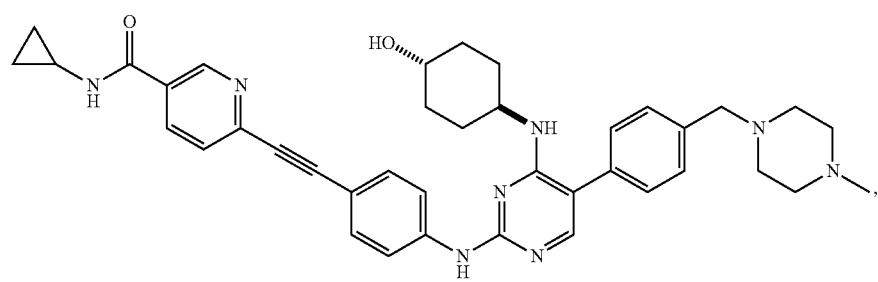
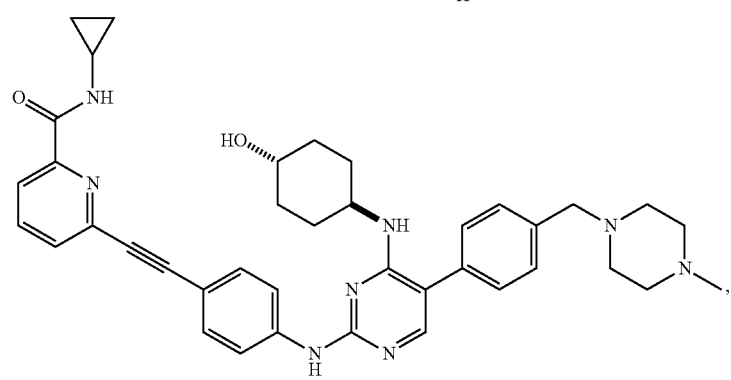
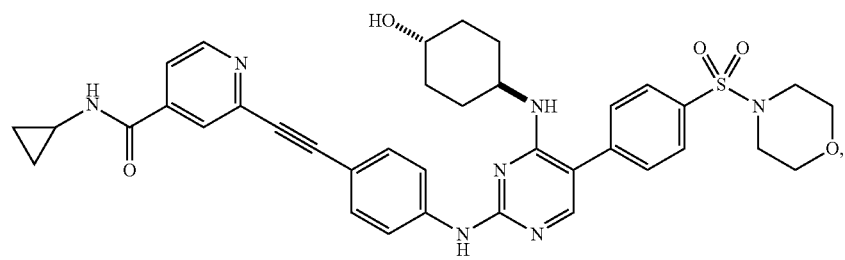
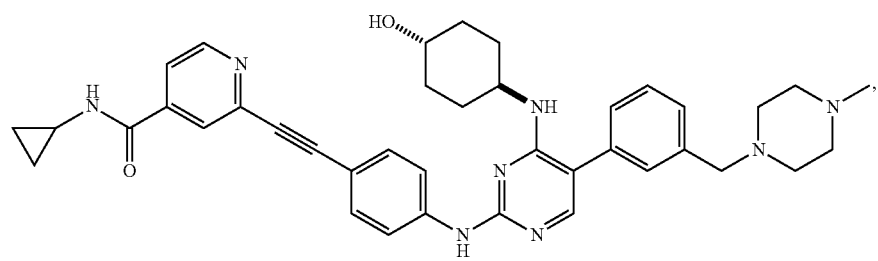
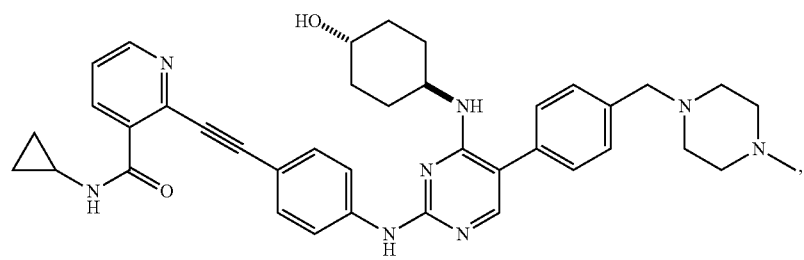

-continued
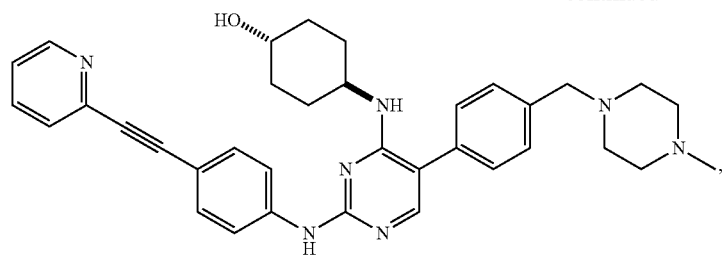
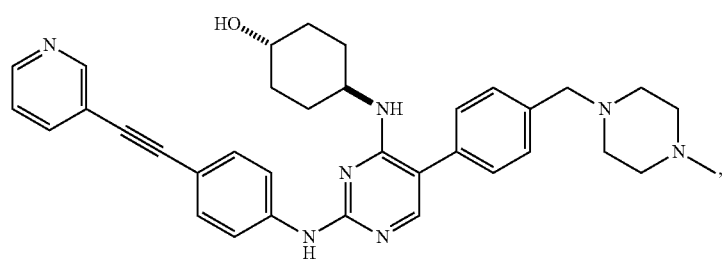
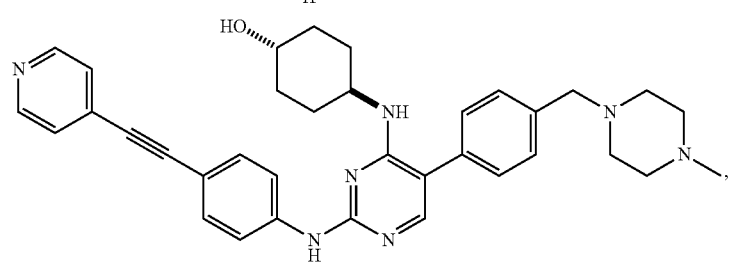
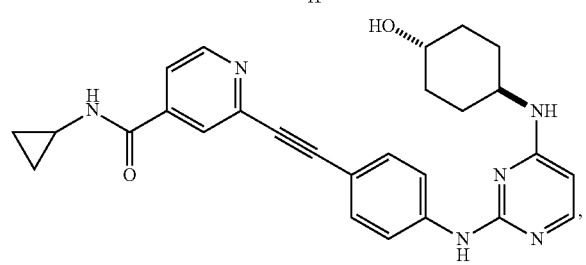
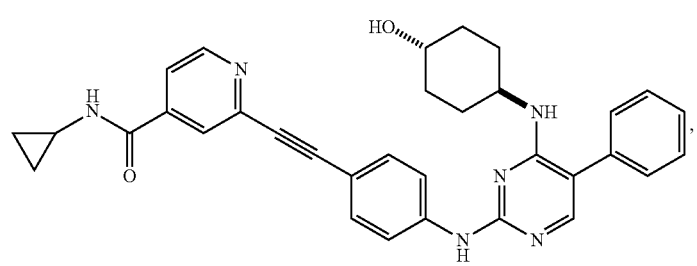
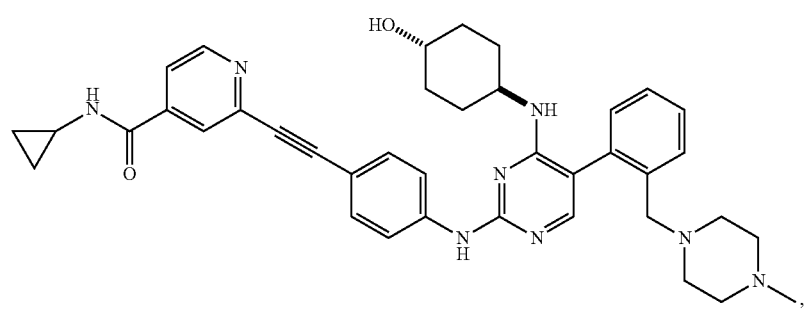

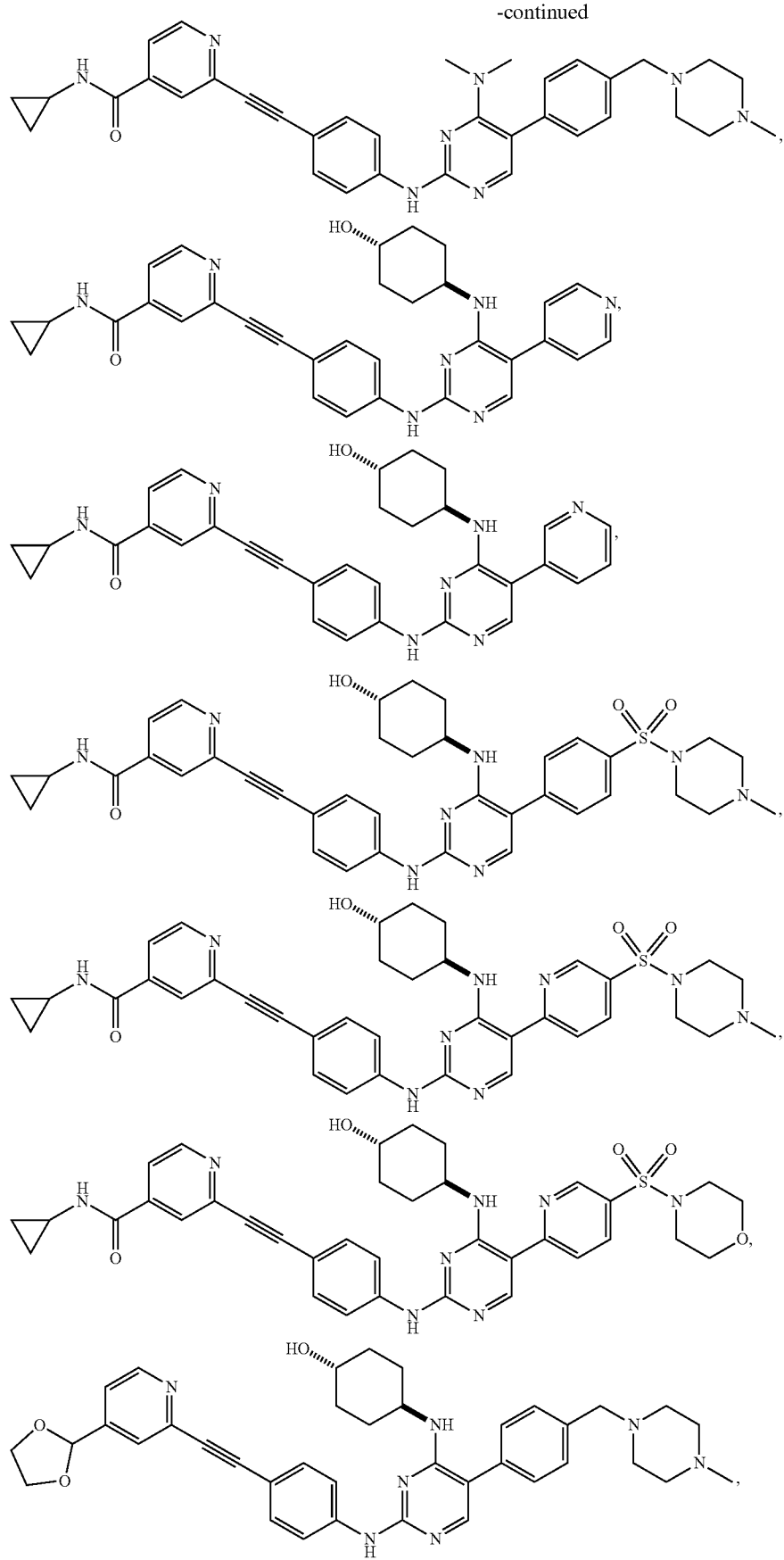

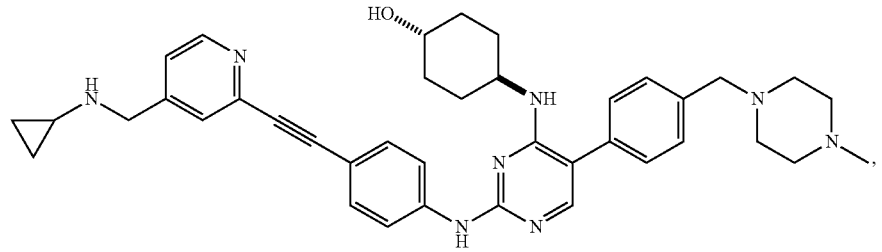
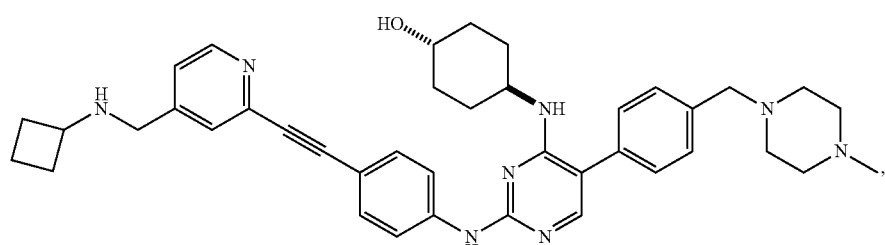
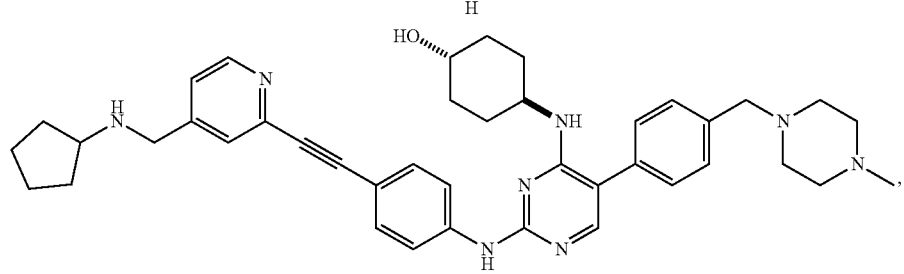
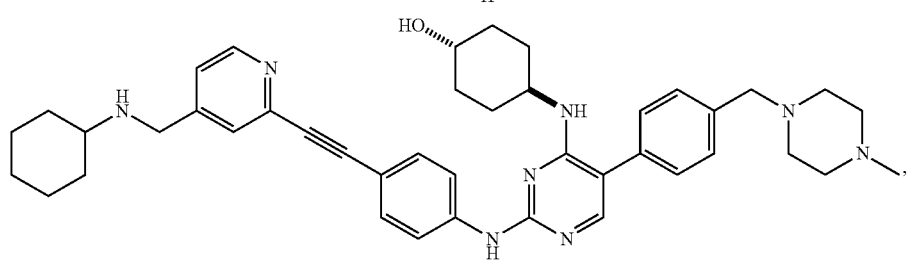
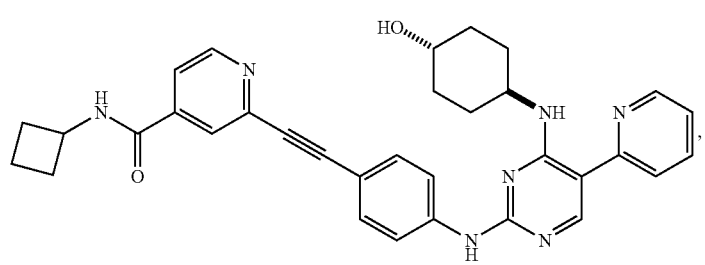
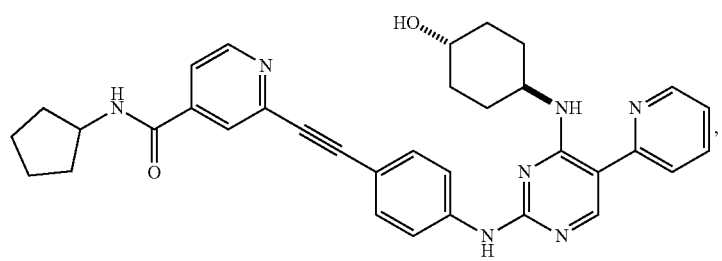

-continued
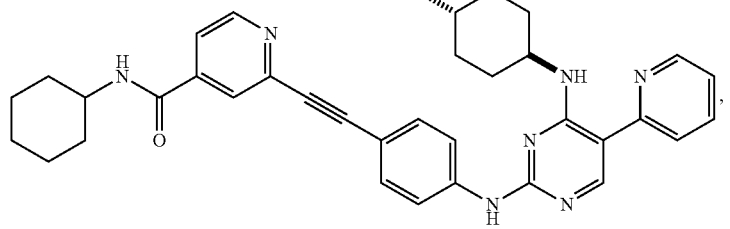
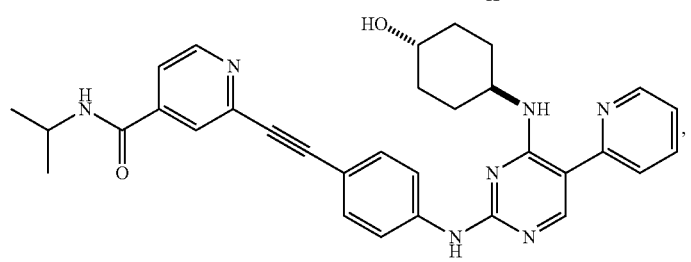
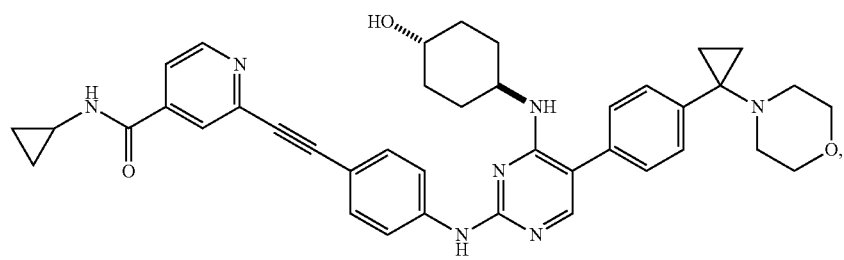
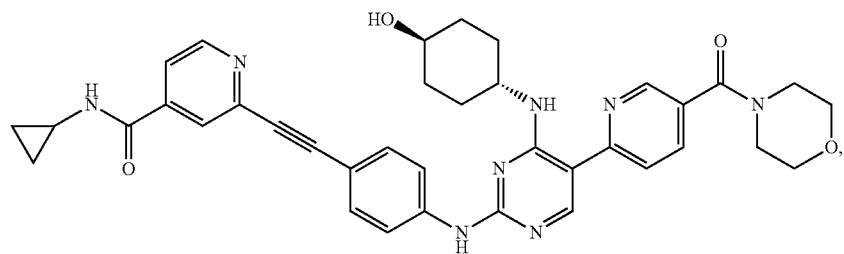
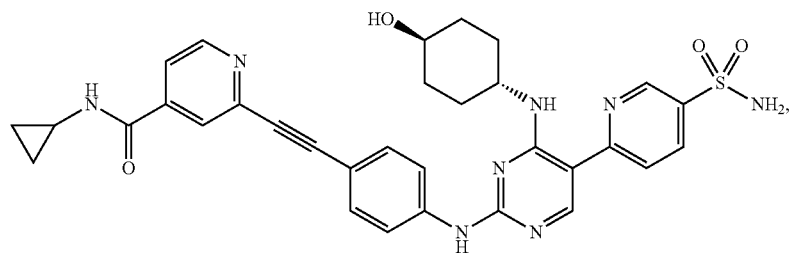
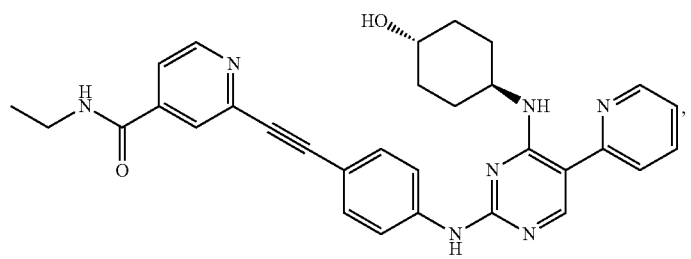

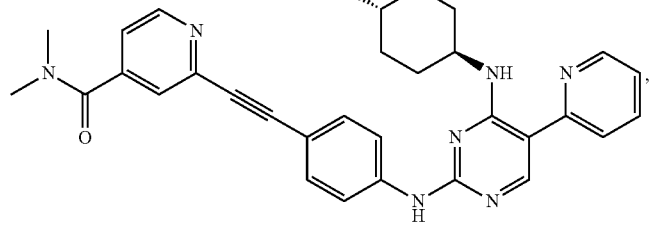
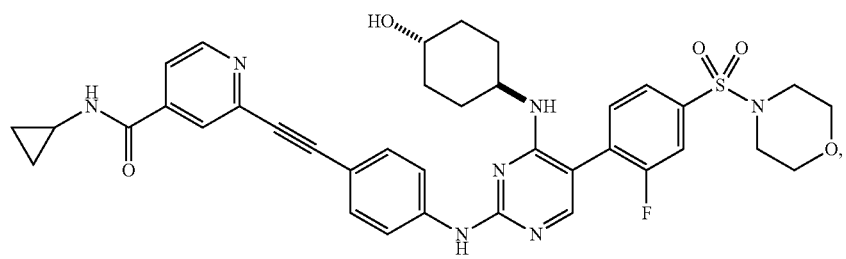
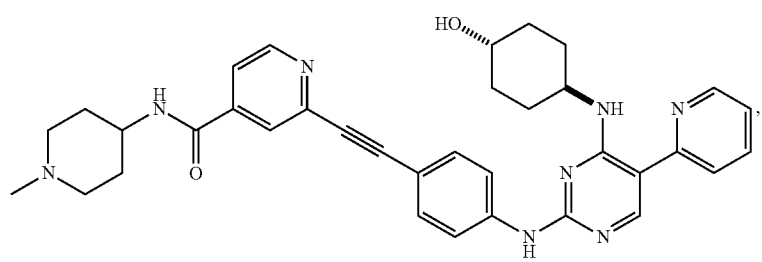
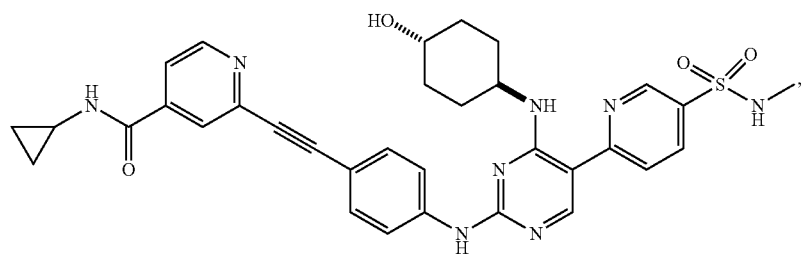
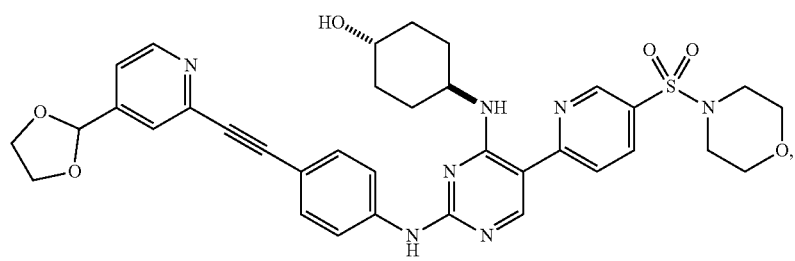
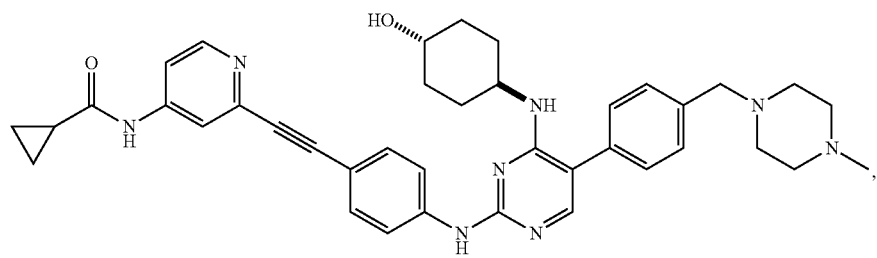

-continued
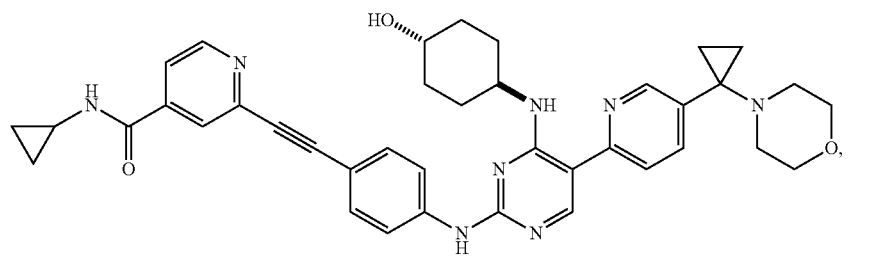
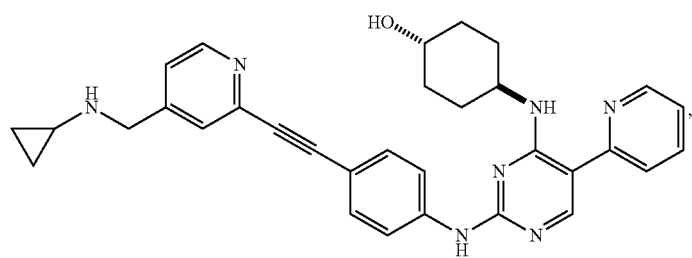
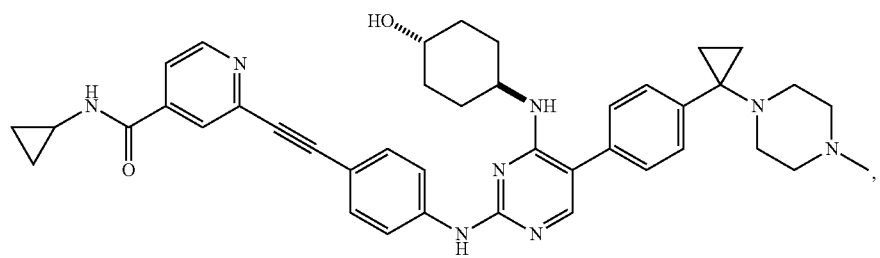
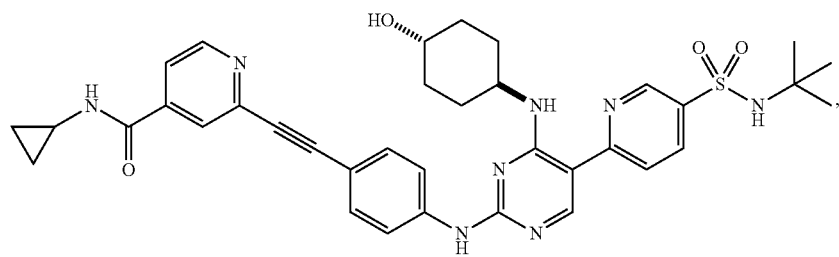
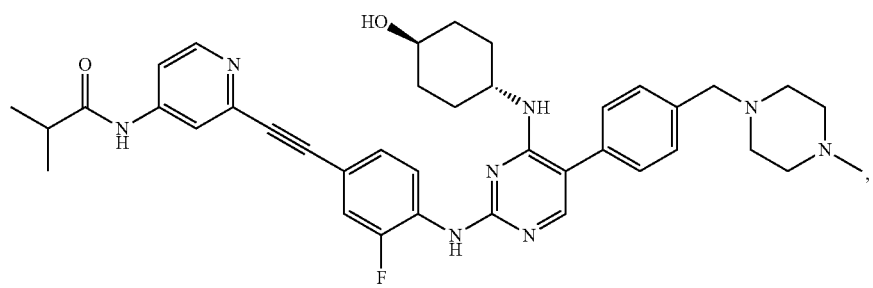
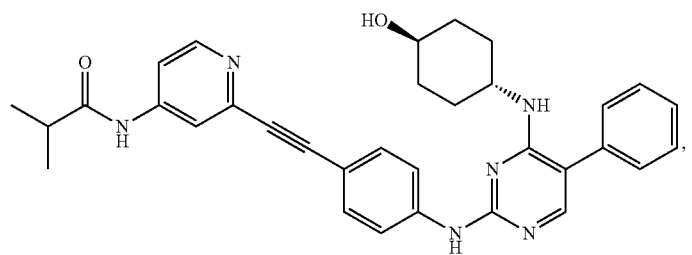

-continued
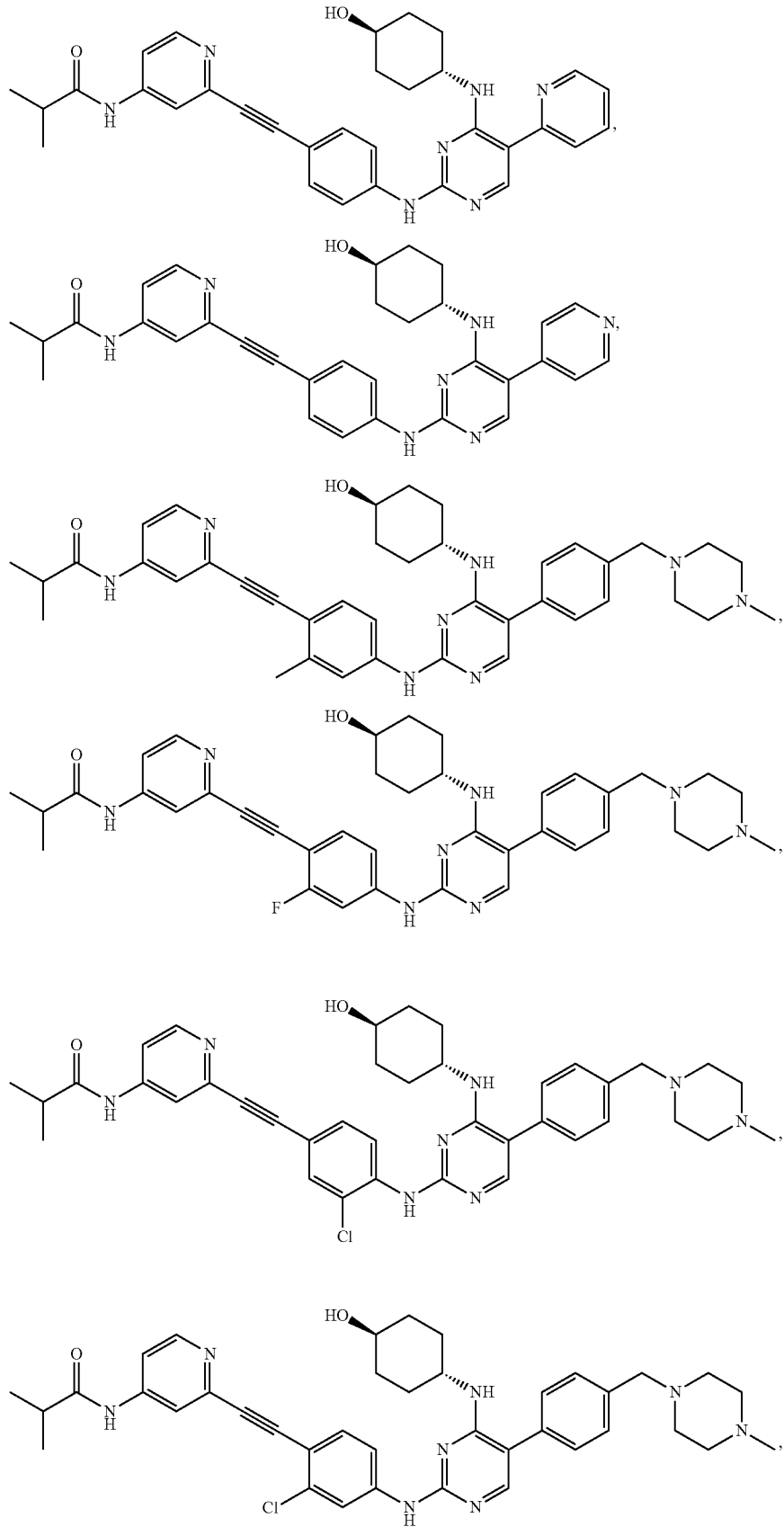

-continued
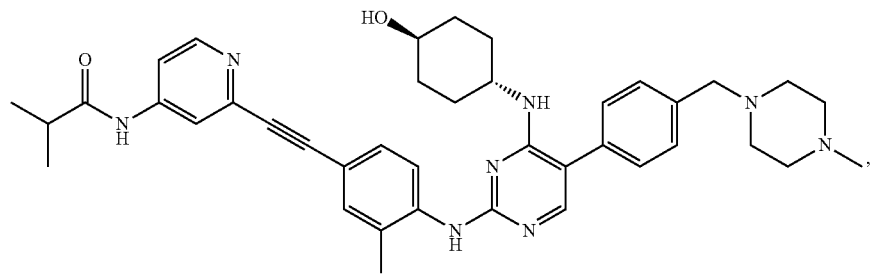
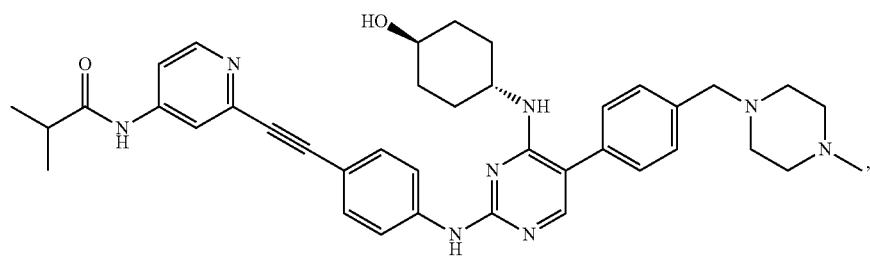
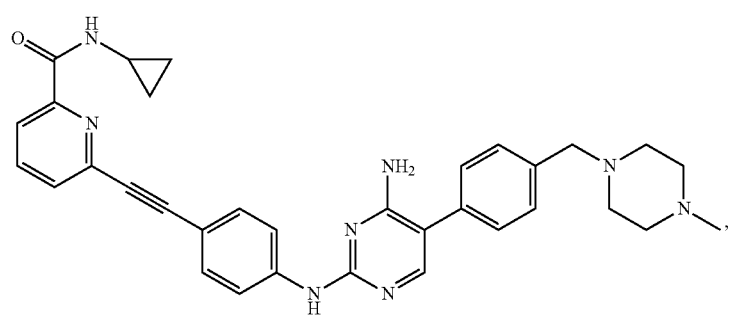
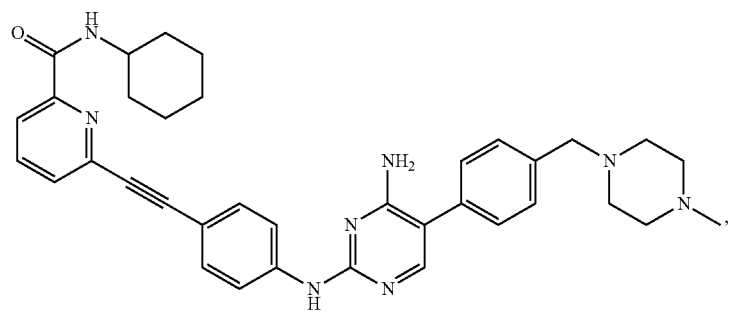
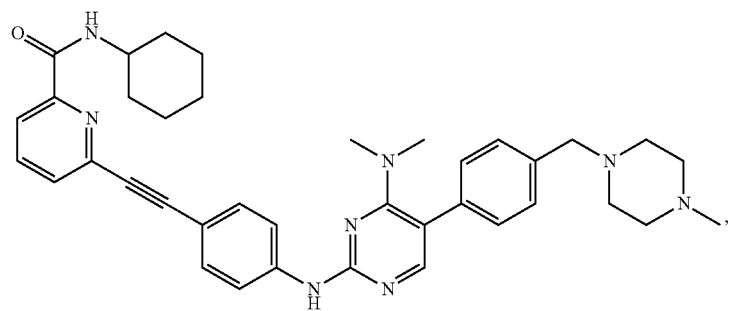

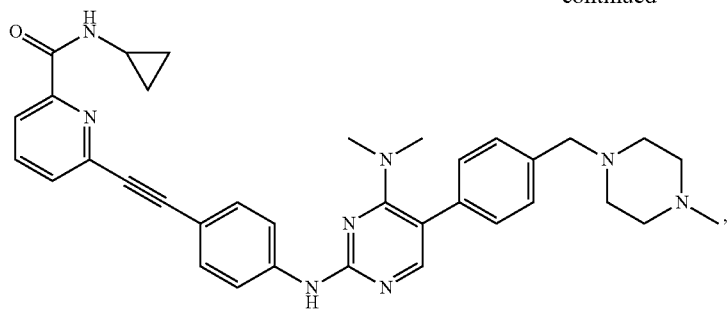
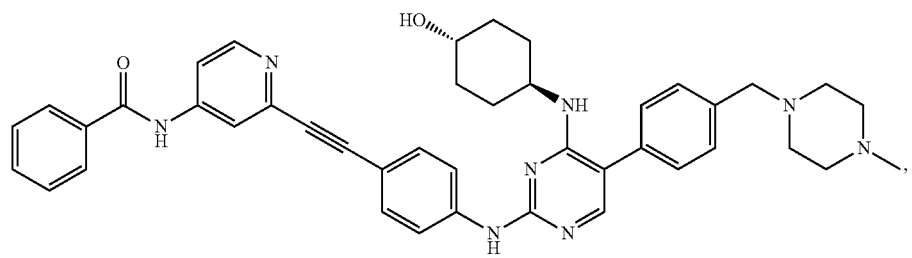
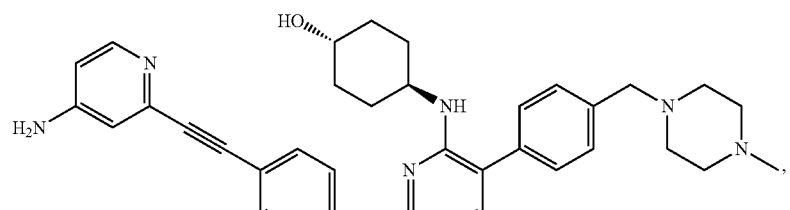
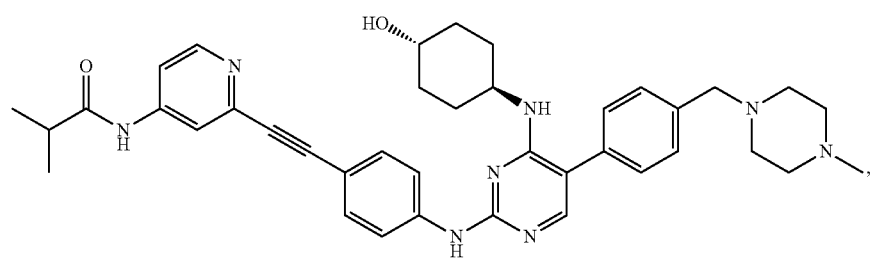
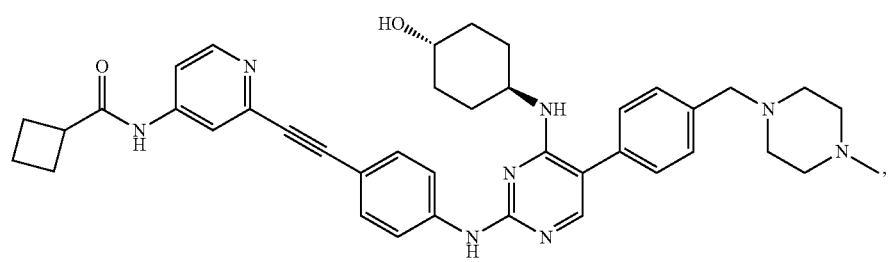
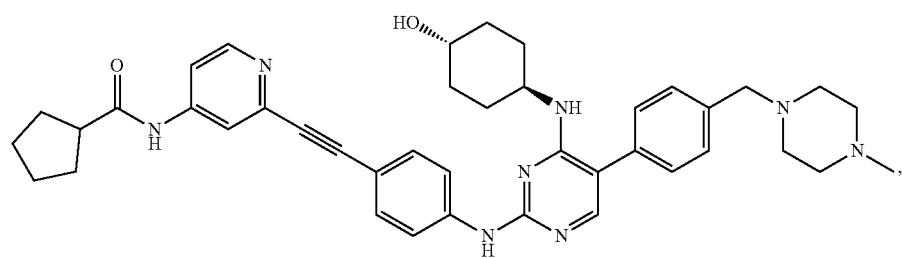

-continued
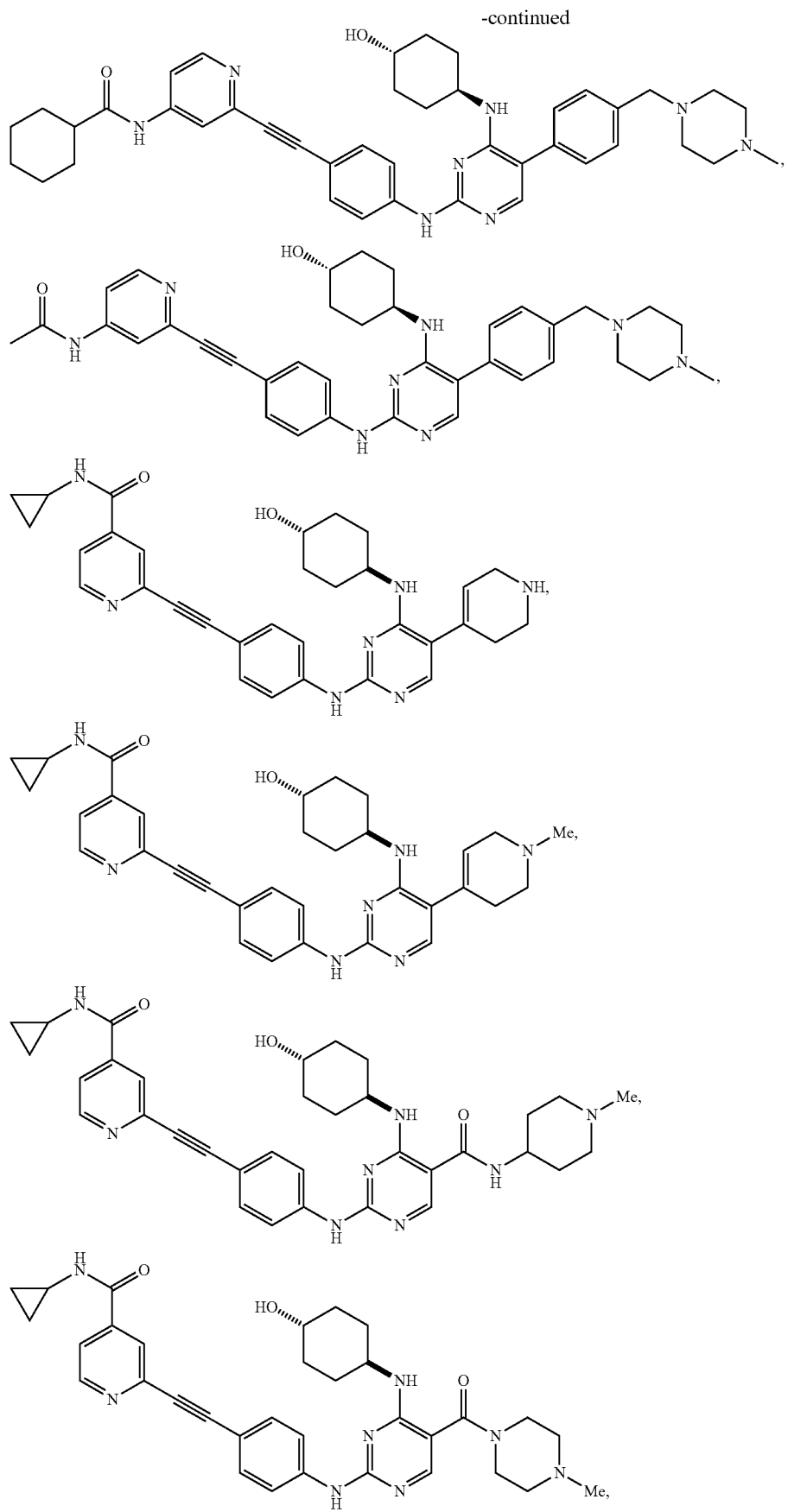

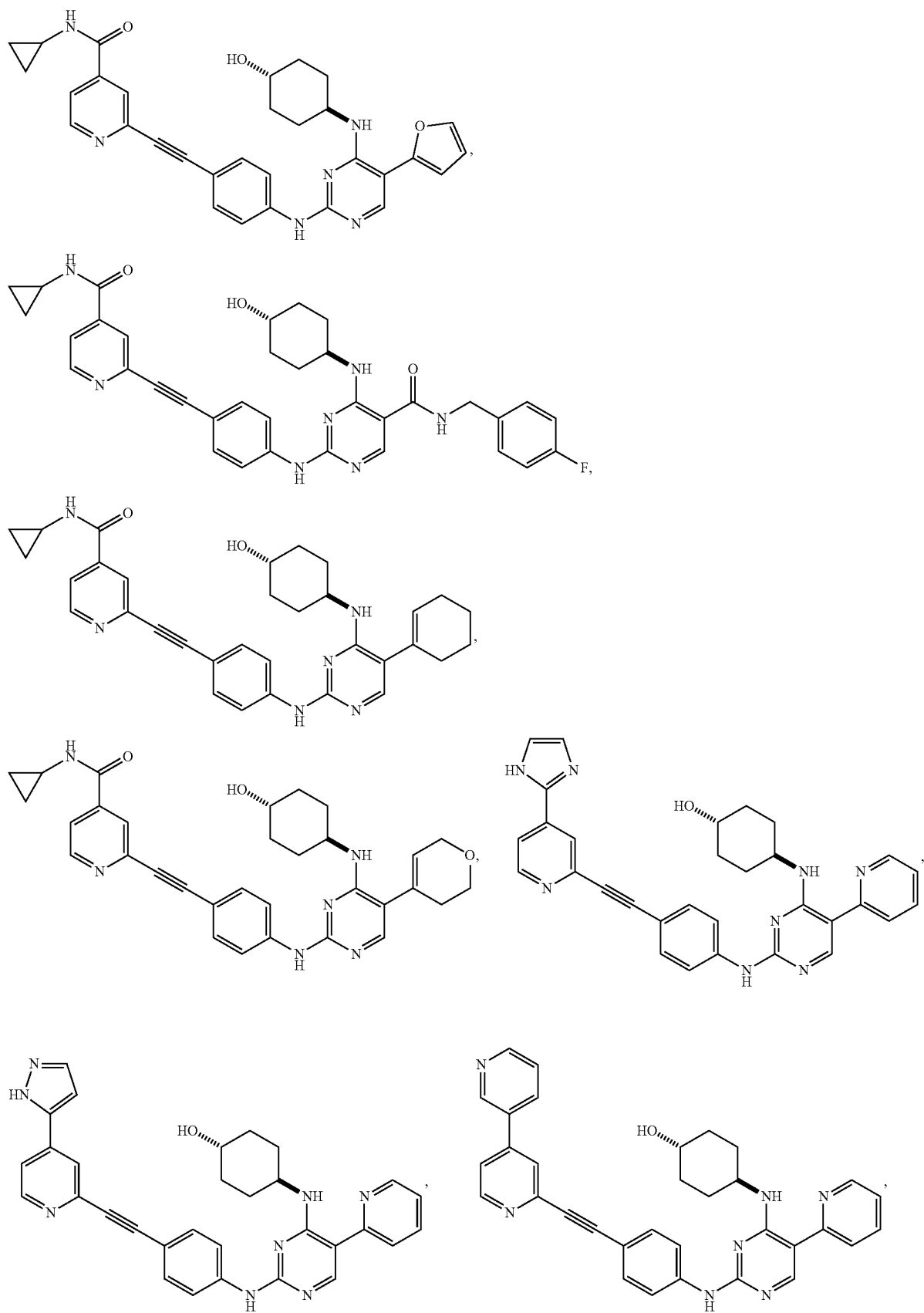

141
142
-continued
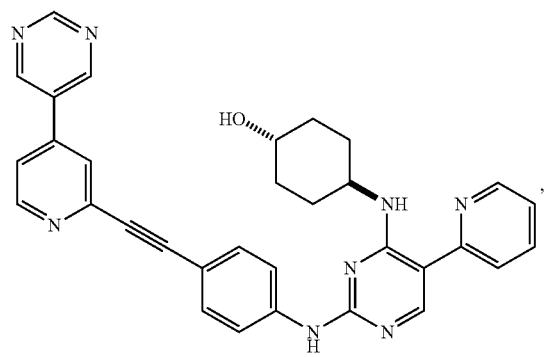
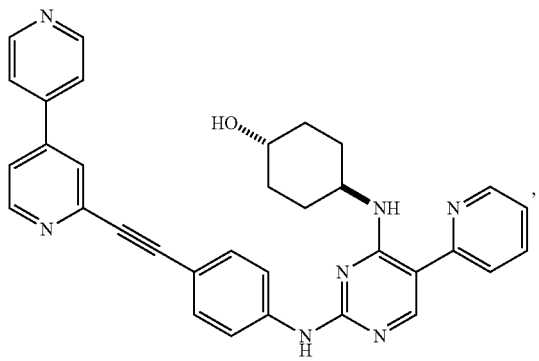
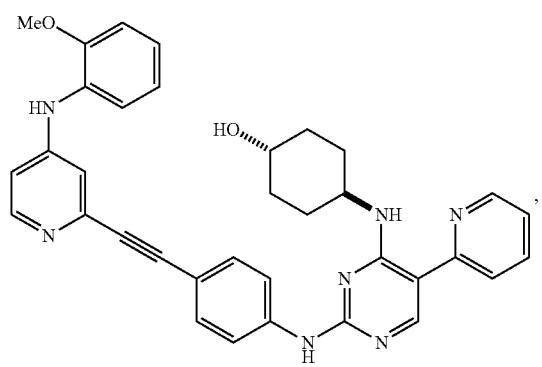
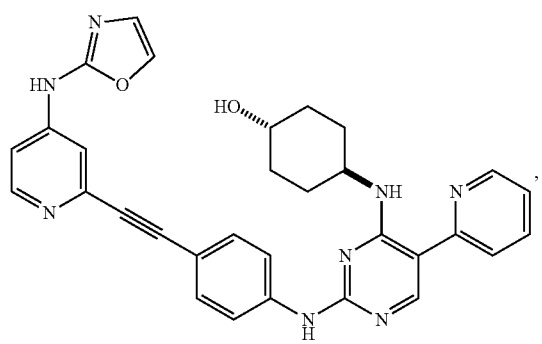
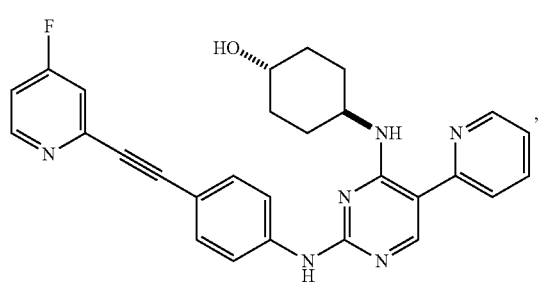
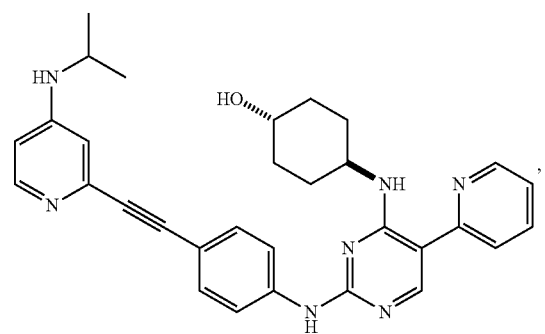
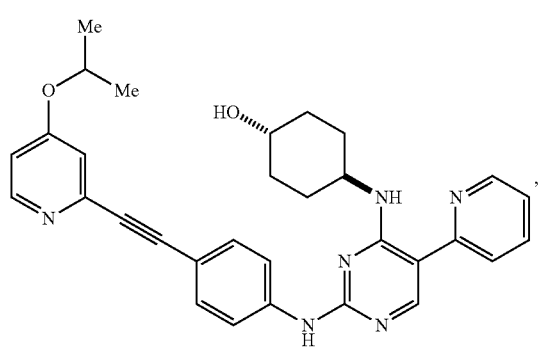
and
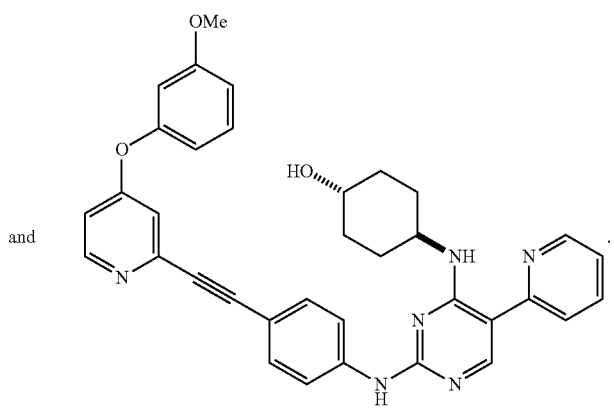

6. The compound of claim 1, wherein the compound is:

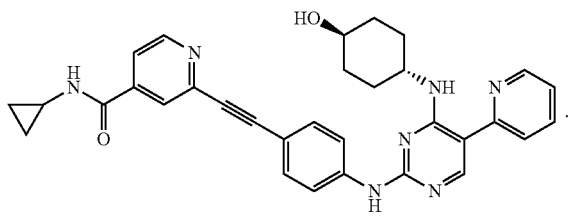 [SMILES: O=C(NC1CC1)c1ccnc(C#Cc2ccc(Nc3ncc(-c4ccccn4)c(N[C@H]4CC[C@H](O)CC4)n3)cc2)c1]

7. A compound of Formula I:

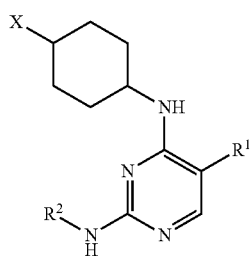

I wherein:

X is —OH, —NH$_2$, —CH$_2$OH or —CH$_2$NH$_2$,

R$^1$ is:

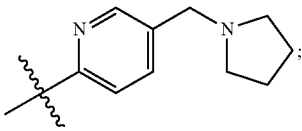 [SMILES: *c1ccc(CN2CCCC2)cn1]

R$^2$ is

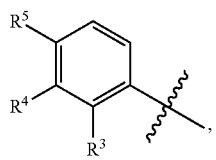 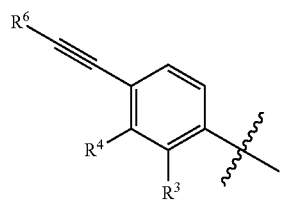

or substituted or unsubstituted heteroaryl,

R$^3$ and R$^4$ are each independently H, halo, lower alkyl or lower alkoxyl,

R$^5$ is H, halo, lower alkyl, lower alkoxyl, CN or SO$_2$Me, and

R$^6$ is substituted or unsubstituted heteroaryl, or a pharmaceutically acceptable salt thereof.

8. The compound of claim 7, wherein the compound is selected from the group consisting of:

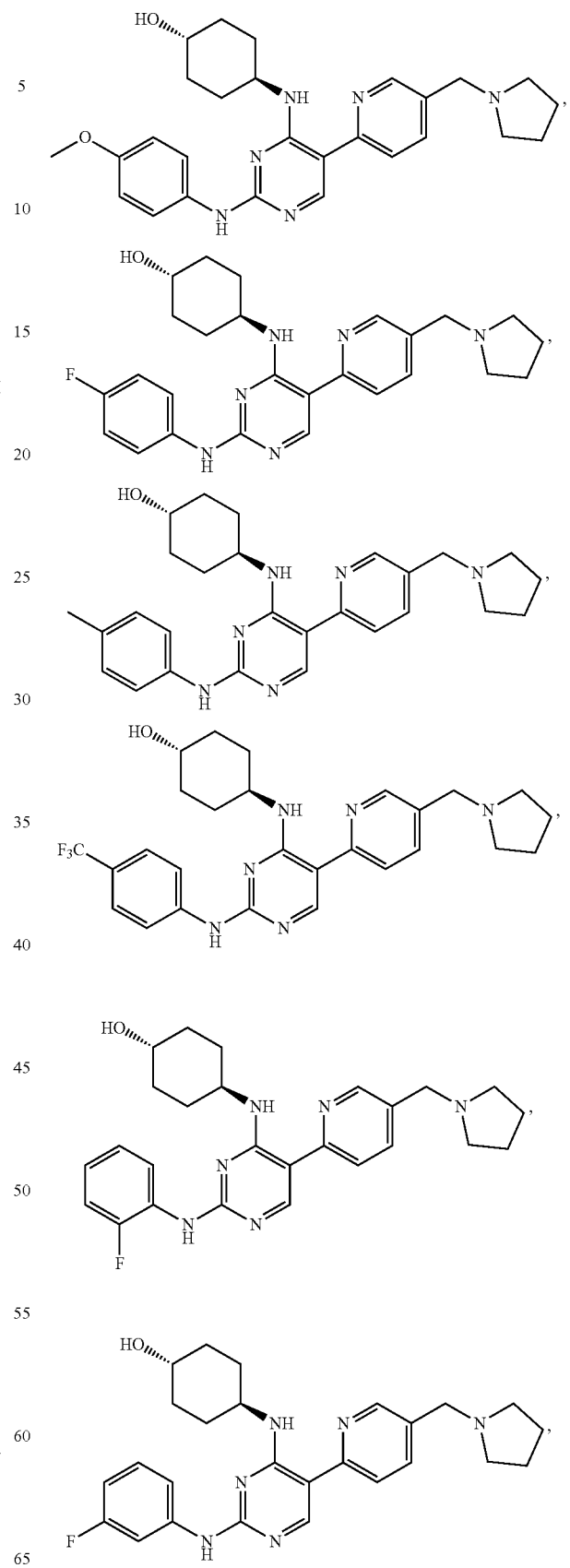

-continued

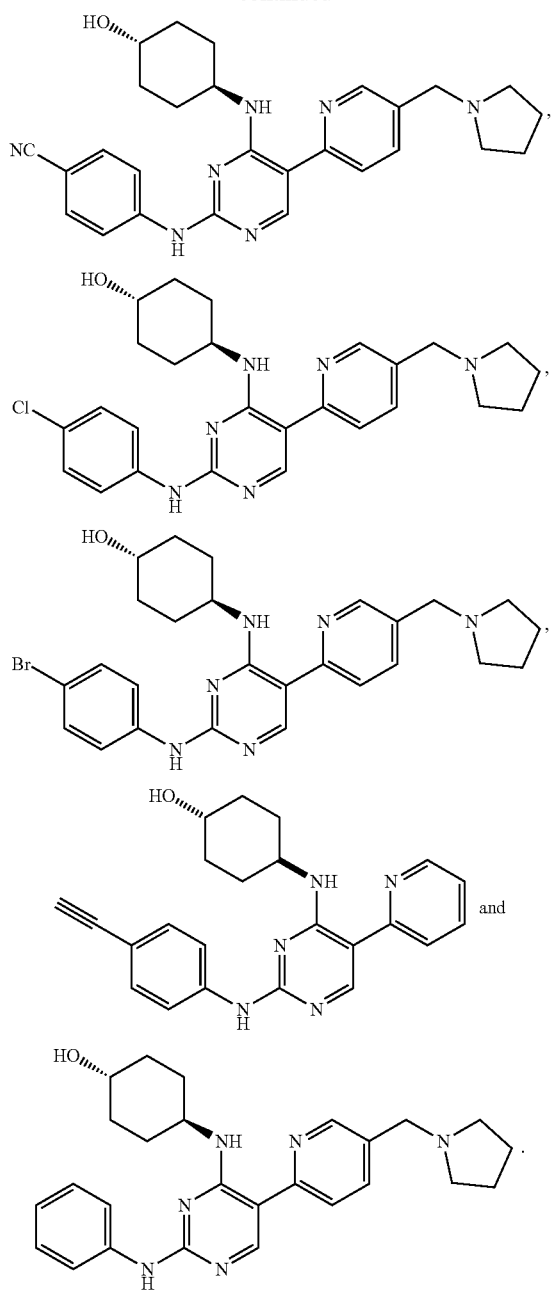

9. The compound of claim 7, wherein the compound is:

10. A compound of Formula V, or VII or:

V wherein:
X is —OH, —NH$_2$, —CH$_2$OH or —CH$_2$NH$_2$;
R$^1$ is H, substituted or unsubstituted aryl, substituted or unsubstituted heteroaryl, substituted or unsubstituted cycloalkenyl, or substituted or unsubstituted heterocycloalkenyl;
R$^{2a}$ and R$^{3a}$ are each independently H, halo, lower alkyl or lower alkoxyl; and
R$^{4a}$ is substituted or unsubstituted heteroaryl; or

VII wherein:
X is —OH, —NH$_2$, —CH$_2$OH or —CH$_2$NH$_2$;
R$^{1c}$ is substituted or unsubstituted alkyl, substituted or unsubstituted cycloalkyl, substituted or unsubstituted aryl, substituted or unsubstituted heteroaryl, substituted or unsubstituted alkylaryl, substituted or unsubstituted alkylheteroaryl, or substituted or unsubstituted alkylcycloalkyl;
R$^{2c}$ and R$^{3c}$ are each independently —H, halo, lower alkyl or lower alkoxyl; and
R$^{4c}$ is substituted or unsubstituted heteroaryl;
or a pharmaceutically acceptable salt thereof.

11. A composition comprising the compound of claim 1, in a pharmaceutically acceptable carrier.

12. A method of treating cancer in a subject in need thereof comprising administering an effective amount of the compound of claim 1.

13. The method of claim 12 further comprising administering to the subject a therapeutically effective amount of a Toll-like receptor (TLR) agonist.

14. A method of inhibiting an Axl and Mer kinase in a subject in need thereof comprising administering an effective amount of the compound of claim 1.

15. A method of treating a cancer in a subject comprising administering an effective amount of the compound of claim 1 in a combination or alternation schedule with an immune checkpoint inhibitor.

16. The method of claim 15, wherein the immune checkpoint inhibitor is a cytotoxic T-lymphocyte-associated protein 4 (CTLA4) inhibitor, a programmed cell death protein 1 (PD1) inhibitor, or a programmed death-ligand 1 (PDL-1) inhibitor.

17. The method of claim 12, wherein the cancer is colon cancer, prostate cancer, non-small cell lung cancer, breast cancer, or melanoma.

* * * * *